(12) United States Patent
Esler et al.

(10) Patent No.: US 11,254,660 B2
(45) Date of Patent: Feb. 22, 2022

(54) COMBINATIONS FOR TREATMENT OF NASH/NAFLD AND RELATED DISEASES

(71) Applicant: Pfizer Inc., New York, NY (US)

(72) Inventors: William Paul Esler, Clinton, CT (US); Trenton Thomas Ross, Brookline, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/553,818

(22) Filed: Aug. 28, 2019

(65) Prior Publication Data

US 2020/0071306 A1 Mar. 5, 2020

Related U.S. Application Data

(60) Provisional application No. 62/883,860, filed on Aug. 7, 2019, provisional application No. 62/726,172, filed on Aug. 31, 2018.

(51) Int. Cl.
*C07D 405/14* (2006.01)
*C07D 471/10* (2006.01)
*A61K 45/06* (2006.01)

(52) U.S. Cl.
CPC ......... *C07D 405/14* (2013.01); *C07D 471/10* (2013.01); *A61K 45/06* (2013.01); *C07B 2200/13* (2013.01)

(58) Field of Classification Search
CPC .............................. C07D 405/14; C07D 471/10
See application file for complete search history.

(56) References Cited

U.S. PATENT DOCUMENTS

2018/0051012 A1 2/2018 Boehm et al.

FOREIGN PATENT DOCUMENTS

WO 2012042433 4/2012

OTHER PUBLICATIONS

Blanco-Ania, Daniel, et al., "Privileged heterocycles: bioactivity and synthesis of 1,9-diazaspiro[5.5] undecane-containing compounds", Chemistry of Heterocyclic Compounds, Oct. 5, 2017, pp. 827-845, 53(8).
Bugianesi, Elisabetta, et al., Abstract Book NAFLD Summit 2018, EASL—The Home of Hepatology, Sep. 20-22, 2018, Geneva, Switzerland, 109 pages.
International Patent Application No. PCT/IB2019/057259, filed Aug. 28, 2019, International Search Report and Written Opinion, dated Jan. 9, 2020, 16 pages.
Lee, Jinhwa, et al., "New Trends in Medicinal Chemistry Approaches to Antiobesity Therapy", Current Topics in Medicinal Chemistry, Apr. 1, 2009, pp. 564-596, 9(6).

*Primary Examiner* — Samira J Jean-Louis
(74) *Attorney, Agent, or Firm* — Richard V. Zanzalari

(57) ABSTRACT

The combination of (S)-2-(5-((3-ethoxypyridin-2-yl)oxy)pyridin-3-yl)-N-(tetrahydrofuran-3-yl)pyrimidine-5-carboxamide or pharmaceutically acceptable salt thereof, and 4-(4-(1-Isopropyl-7-oxo-1,4,6,7-tetrahydrospiro[indazole-5,4'-piperidine]-1'-carbonyl)-6-methoxypyridin-2-yl)benzoic acid or pharmaceutically acceptable salt thereof, for treatment of diseases, including non-alcoholic steatohepatitis (NASH), in mammals are described herein.

25 Claims, 23 Drawing Sheets

FIG. 12
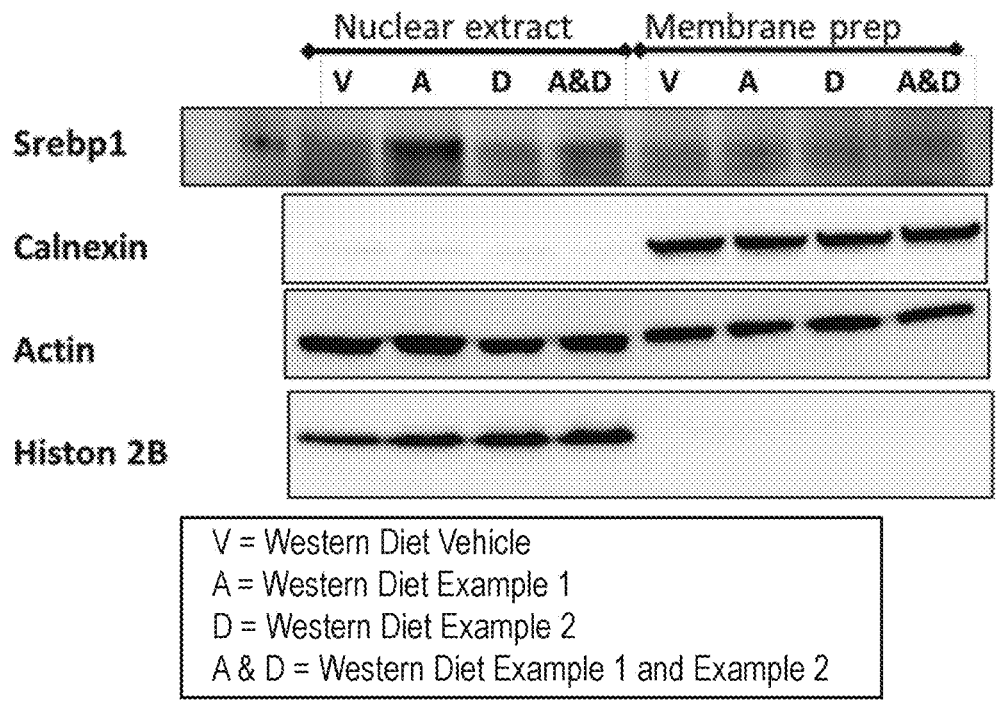
V = Western Diet Vehicle
A = Western Diet Example 1
D = Western Diet Example 2
A & D = Western Diet Example 1 and Example 2
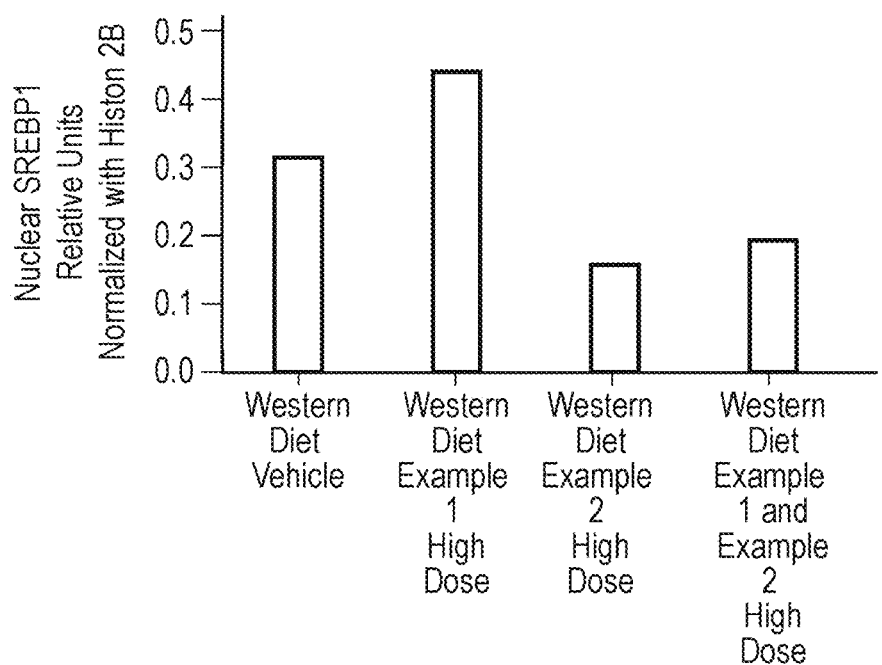

ACC1

FASN

COMBINATIONS FOR TREATMENT OF NASH/NAFLD AND RELATED DISEASES

FIELD OF THE INVENTION

The invention relates to new pharmaceutical compositions comprising (S)-2-(5-((3-ethoxypyridin-2-yl)oxy)pyridin-3-yl)-N-(tetrahydrofuran-3-yl)pyrimidine-5-carboxamide, or pharmaceutically acceptable salt thereof, and in the same or a separate composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid, or pharmaceutically acceptable salt thereof, for treatment of non-alcoholic fatty liver disease (NAFLD) and diseases related thereto, e.g., non-alcoholic steatohepatitis (NASH) and metabolic-related diseases.

BACKGROUND OF THE INVENTION

Nonalcoholic steatohepatitis (NASH) is a clinical and histological subset of non-alcoholic fatty liver disease (NAFLD, defined as presence of ≥5% hepatic steatosis) that is associated with increased all cause mortality, cirrhosis and end stage liver disease, increased cardiovascular mortality, and increased incidence of both liver related and non-liver related cancers (Sanyal et al, *Hepatology* 2015; 61(4):1392-1405). NAFLD is the hepatic manifestation of metabolic syndrome, and is a spectrum of hepatic conditions encompassing steatosis, NASH, fibrosis, cirrhosis and ultimately hepatocellular carcinoma. NAFLD and NASH are considered the primary fatty liver diseases as they account for the greatest proportion of individuals with elevated hepatic lipids. The severity of NAFLD/NASH is based on the presence of lipid, inflammatory cell infiltrate, hepatocyte ballooning, and the degree of fibrosis. At the present time, treatment options are limited to management of associated conditions (EASL-EASD-EASO Clinical Practice Guidelines, *J. Hepatol.* 2016; 64(6):1388-1402).

Alterations in lipid metabolism have been hypothesized to contribute to the molecular pathogenesis of NAFLD and NASH. Steatosis is a necessary but not sufficient component of the pathogenesis of NASH (Day C, and James O., *Hepatology.* 1998; 27(6):1463-6). Consistent with this, multiple studies have demonstrated that the severity of steatosis predicts the risk of concomitant steatohepatitis as well as the risk of progression to cirrhosis (Sorensen et al, *Lancet.* 1984; 2(8397): 241-4; Wanless I and Lentz J, *Hepatology* 1990; 12(5):1106-10; Reeves H, et al, *J. Hepatol.* 1996; 25(5): 677-83). Hepatic steatosis is a consequence of an imbalance in TG production/uptake into the liver and clearance/removal (Cohen J C, et al, *Science.* 2011; 332(6037):1519-1523). It is hypothesized that reducing steatosis, the metabolic driver underpinning the development of NAFLD/ NASH, will result in subsequent improvements in hepatic inflammation and fibrosis.

Acetyl-CoA Carboxylase (ACC) and diacylglycerol acyltransferase 2 (DGAT2) are two key enzymes regulating lipid metabolism. ACC catalyzes an essential and rate limiting step in the process of de novo lipogenesis (DNL) (Saggerson D, *Annu. Rev. Nutr.* 2008; 28:253-72.). Further, ACC also regulates mitochondrial beta-oxidation of fatty acids through allosteric regulation of the enzyme carnitine palmitoyltransferase 1 (CPT1) (Saggerson, 2008; Waite M, and Wakil S J. *J. Biol. Chem.* 1962; 237:2750-2757.). Emerging data also suggest that suppression of DNL through ACC inhibition may directly reduce inflammation by restraining the formation of the inflammatory interleukin-17 (IL-17) secreting T-cells of the T helper 17 lineage (Th17 cells) and favoring the development of anti-inflammatory FoxP3(+) regulatory T (Treg) cells (Berod L, et al. *Nat. Med.* 2014; 20(11): 1327-33).

Inhibition of ACC activity is hypothesized to be beneficial to patients with NASH by at least two independent mechanisms. As summarized above, humans with NAFLD show marked elevations in hepatic DNL and normalization of this increased flux through pharmacologic hepatic ACC inhibition is hypothesized to reduce steatosis. In addition, the effect of ACC inhibitors to increase fatty acid oxidation may also contribute to reduce liver fat content. Consistent with this, ACC inhibitors have been shown to inhibit DNL. See Griffith D A, et al. *J. Med. Chem.* 2014; 57(24):10512-10526; Kim C W, et al. *Cell Metab.* 2017; 26, 394-406; Stiede K, et al. *Hepatology.* 2017; 66(2):324-334; Lawitz E J, et al. *Clin Gastroenterol Hepatol.* 2018 (https://doi.org/10.1016/j.cgh.2018.04.042). In addition, inhibition of DNL in IL-17 secreting T-cells is expected to suppress hepatic inflammation by restraining the formation of the inflammatory Th17 cells (Berod et al., 2014), a pathway that may be important in NASH pathogenesis (Rau M, et al. *J. Immunol.* 2016; 196(1):97-105), and favoring the development of anti-inflammatory Treg cells. Further, ACC inhibition may reduce stellate cell activation and fibrosis (Ross et al., 2019).

Triglycerides or triacylglycerols (TG) represent a major form of energy storage in mammals. TG's are formed by the sequential esterification of glycerol with three fatty acids of varying chain lengths and degrees of saturation (Coleman, R. A., and Mashek, D. G. 2011. *Chem. Rev.* 111: 6359-6386). TG synthesized in the intestine or liver are packaged into chylomicrons or very low-density lipoprotein (VLDL), respectively, and exported to peripheral tissues where they are hydrolyzed to their constituent fatty acids and glycerol by lipoprotein lipase (LPL). The resultant non-esterified fatty acids (NEFA) can either be metabolized further to produce energy or reesterified and stored.

Under normal physiological conditions, the energy-dense TG remains sequestered in various adipose depots until there is a demand for its release, whereupon, it is hydrolyzed to glycerol and free fatty acids which are then released into the blood stream. This process is tightly regulated by the opposing actions of insulin and hormones such as catecholamines which promote the deposition and mobilization of TG stores under various physiological conditions. In the post-prandial setting, insulin acts to inhibit lipolysis, thereby, restraining the release of energy in the form of NEFA and ensuring the appropriate storage of dietary lipids in adipose depots. However, in patients with type 2 diabetes, the ability of insulin to suppress lipolysis is ameliorated and NEFA flux from adipocytes is inappropriately elevated. This, in turn, results in increased delivery of lipid to tissues such as muscle and liver. In the absence of energetic demand the TG and other lipid metabolites, such as diacylglycerol (DAG) can accumulate and cause a loss of insulin sensitivity (Erion, D. M., and Shulman, G. I. 2010. *Nat Med* 16: 400-402). Insulin resistance in muscle is characterized by reduced glucose uptake and glycogen storage, whilst in the liver, loss of insulin signaling gives rise to dysregulated glucose output and over-production of TG-rich VLDL, a hallmark of type 2 diabetes (Choi, S. H., and Ginsberg, H. N. 2011. *Trends Endocrinol. Metab.* 22: 353-363). Elevated secretion of TG-enriched VLDL, so called VLDL1 particles, is thought to stimulate the production of small, dense low-density lipoprotein (sdLDL), a proatherogenic subfraction of LDL that is associated with elevated risk of coronary heart disease (St-Pierre, A. C. et. al. 2005. *Arterioscler. Thromb. Vasc. Biol.* 25: 553-559).

In mammals, two diacylglycerol acyltransferases (DGAT) enzymes (DGAT1 and DGAT2) have been characterized. Although these enzymes catalyze the same enzymatic reaction, their respective amino acid sequences are unrelated and they occupy distinct gene families. Mice harboring a disruption in the gene encoding DGAT1 are resistant to diet-induced obesity and have elevated energy expenditure and activity (Smith, S. J. et. al., 2000. *Nat Genet* 25: 87-90). Dgat1−/− mice exhibit dysregulated postaborpative release of chylomicrons and accumulate lipid in the enterocytes (Buhman, K. K. et. al. 2002. *J. Biol. Chem.* 277: 25474-25479). The metabolically favorable phenotype observed in these mice is suggested to be driven by loss of DGAT1 expression in the intestine (Lee, B., et. al. 2010. *J. Lipid Res.* 51: 1770-1780). Importantly, despite a defect in lactation in female Dgat1−/− mice, these animals retain the capacity to synthesize TG suggesting the existence of additional DGAT enzymes. This observation and the isolation of a second DGAT from the fungus *Mortierella rammaniana* led to the identification and characterization of DGAT2 (Yen, C. L. et. al. 2008. *J. Lipid Res.* 49: 2283-2301).

DGAT2 is highly expressed in liver and adipose, and unlike DGAT1, exhibits exquisite substrate specificity for DAG (Yen, C. L., 2008). Deletion of the DGAT2 gene in rodents results in defective intrauterine growth, severe lipemia, impaired skin barrier function, and early post-natal death (Stone, S. J. et. al. 2004. *J. Biol. Chem.* 279: 11767-11776). Due to the lethality caused by loss of DGAT2, much of our understanding of the physiological role of DGAT2 derives from studies performed with antisense oligonucleotides (ASO) in rodent models of metabolic disease. In this setting, inhibition of hepatic DGAT2 resulted in improvements in plasma lipoprotein profile (decrease in total cholesterol and TG) and a reduction of hepatic lipid burden which was accompanied by improved insulin sensitivity and whole-body glucose control (Liu, Y. et. al. 2008. *Biochim. Biophys. Acta* 1781: 97-104; Choi, C. S. et. al. 2007. *J. Biol. Chem.* 282: 22678-22688; Yu, X. X. et. al. 2005. *Hepatology* 42: 362-371). Although the molecular mechanisms underlying these observations are not fully elucidated, it is clear that suppression of DGAT2 results in a down-regulation of the expression of multiple genes encoding proteins involved in lipogensis, including sterol regulatory element-binding proteins 1c (SREBP1c) and stearoyl CoA-desaturase 1 (SCD1) (Choi, 2007; Yu, 2005). In parallel, oxidative pathways are induced as evidenced by increased expression of genes such as carnitine palmitoyl transferase 1 (CPT1) (Choi, 2007). The net result of these changes is to decrease the levels of hepatic DAG and TG lipid which, in turn, leads to improved insulin responsiveness in the liver.

Furthermore, DGAT2 inhibition suppresses hepatic VLDL TG secretion and reduction in circulating cholesterol levels. Finally, plasma apolipoprotein B (APOB) levels were suppressed, possibly due to decreased supply of TG for lipidation of the newly synthesized APOB protein (Liu, 2008; Yu, 2005). The beneficial effects of DGAT2 inhibition on both glycemic control and plasma cholesterol profile suggest that this target might be valuable in the treatment of metabolic disease (Choi, 2007). In addition, the observation that suppression of DGAT2 activity results in reduced hepatic lipid accumulation suggests that inhibitors of this enzyme might have utility in the treatment of NASH.

In view of the above, there exists a need for medicaments, for example, oral medicaments, containing combination of (S)-2-(5-((3-ethoxypyridin-2-yl)oxy)pyridin-3-yl)-N-(tetrahydrofuran-3-yl)pyrimidine-5-carboxamide (DGAT2 inhibitor) or pharmaceutically acceptable salt thereof, and in the same or a separate composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid (ACCI inhibitor) or pharmaceutically acceptable salt thereof. The specific combinations described herein satisfy the existing need.

SUMMARY OF THE INVENTION

The invention is directed at a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with at least 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, each present in therapeutically effective amounts, in admixture with a pharmaceutically acceptable excipient.

The invention is also directed at a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, and 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, in admixture with a pharmaceutically acceptable excipient.

The invention is also directed at a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, said method includes administering to the patient in need of such treatment a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof.

The invention is also directed at a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with at least a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof.

The invention is also directed at a method for treating fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and with hepatocellular carcinoma in humans comprising the step of administering to a human in need of such treatment a therapeutically effective amount of a first and second compositions and optionally a third composition wherein
  i. the first composition comprises (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, and a pharmaceutically acceptable excipient;
  ii. the second composition comprises 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, and a pharmaceutically acceptable excipient; and
  iii. the third composition comprises a pharmaceutical agent selected from the group consisting of an anti-inflammatory agent, an anti-diabetic agent, an anti-fibrotic agent, an anti-steatiotic agent, a cholesterol/lipid modulating agent, and an anti-diabetic agent, and a pharmaceutically acceptable excipient.

The invention is also directed at a method for treating fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and with hepatocellular carcinoma in humans comprising the step of administering to a human in need of such treatment a therapeutically effective amount of two separate pharmaceutical compositions comprising
  i. a first composition that includes (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, present in a therapeutically effective amount, in admixture with a pharmaceutically acceptable excipient;
  ii. a second composition that includes 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, present in a therapeutically effective amount, in admixture with a pharmaceutically acceptable excipient; and optionally
  iii. a third composition comprising at least one additional pharmaceutical agent selected from the group consisting of a GLP-1R agonist, a KHK inhibitor, or an FXR agonist, and a pharmaceutically acceptable excipient.

The invention is also directed to A method of treating heart failure, congestive heart failure, coronary heart disease, peripheral vascular disease, renovascular disease, pulmonary hypertension, vasculitis, acute coronary syndromes and modification of cardiovascular risk comprising administering to a human in need of such treatment a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with at least a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof.

The invention is also directed to a method of treating obesity, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia, and maple syrup urine disease comprising administering to a human in need of such treatment a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with at least a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof.

The invention is also directed to a method of treating hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, lung adenocarcinoma comprising administering to a human in need of such treatment a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with at least a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof.

It is to be understood that both the foregoing general description and the following detailed description are exemplary and explanatory only and are not restrictive of the invention, as claimed.

BRIEF DESCRIPTION OF THE DRAWINGS

FIG. 12 summarizes the effect of administration of Compound A and Compound D as monotherapy and in combination on SREBP-1 nuclear localization in Western diet fed rats.

DETAILED DESCRIPTION OF THE INVENTION

Figure 1:
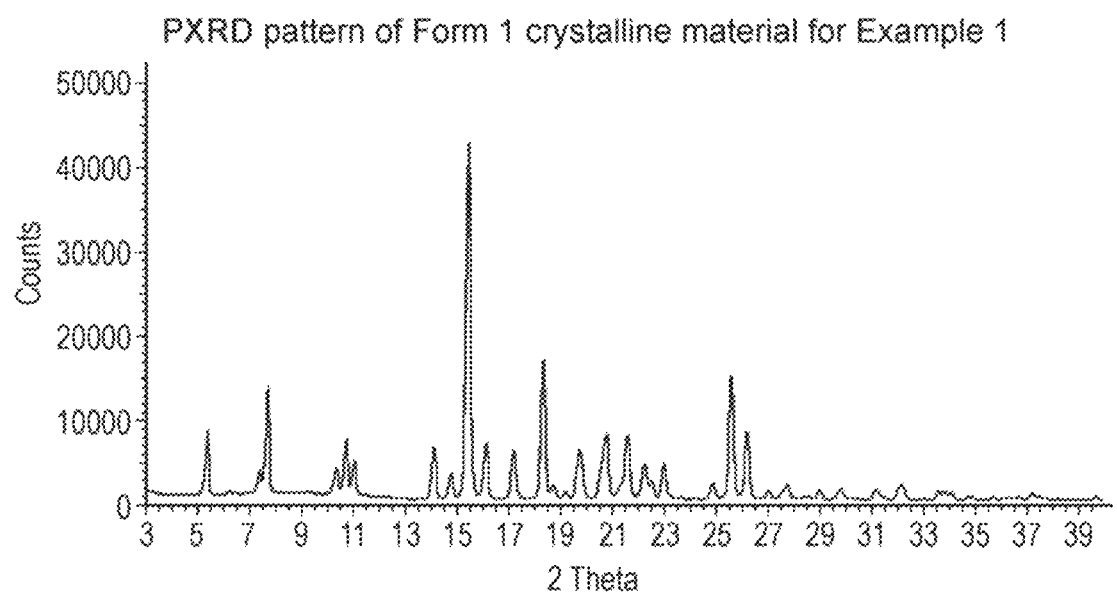
FIG. 1 is a characteristic x-ray powder diffraction pattern showing crystalline Form 1 of Example 1 of the DGAT2i Compound (Vertical Axis: Intensity (CPS); Horizontal Axis: Two theta (degrees)).

The invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

"Compounds" when used herein includes any pharmaceutically acceptable derivative or variation, including conformational isomers e, cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the compounds of the invention include but are not limited to those having a carboxyl moiety wherein the free hydrogen is replaced by ($C_1$-$C_4$)alkyl, ($C_2$-$C_7$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as 1-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

As used herein, an arrowhead, "╱" or wavy line, "⌇" denotes a point of attachment of a substituent to another group.

"Patient" refers to warm blooded animals such as, for example, guinea pigs, mice, rats, gerbils, cats, rabbits, dogs, cattle, goats, sheep, horses, monkeys, chimpanzees, and humans. A "mammal" is a patient.

By "pharmaceutically acceptable" is meant that the substance or composition must be compatible chemically and/or toxicologically, with the other ingredients comprising a formulation, and/or the mammal being treated therewith.

As used herein, the following terms have the general meaning for administration of pharmaceutical agents: QD means once daily and BID means twice daily.

As used herein, the expressions "reaction-inert solvent" and "inert solvent" refer to a solvent or a mixture thereof which does not interact with starting materials, reagents, intermediates or products in a manner which adversely affects the yield of the desired product.

As used herein, the term "selectivity" or "selective" refers to a greater effect of a compound in a first assay, compared to the effect of the same compound in a second assay. For example, in "gut selective" compounds, the first assay is for the half-life of the compound in the intestine and the second assay is for the half-life of the compound in the liver.

"Therapeutically effective amount" means an amount of 4-(4-(1-Isopropyl-7-oxo-1,4,6,7-tetrahydrospiro[indazole-5, 4'-piperidine]-1'-carbonyl)-6-methoxypyridin-2-yl)benzoic acid (Compound A) in combination with an amount of (S)-2-(5-((3-Ethoxypyridin-2-yl)oxy)pyridin-3-yl)-N-(tetrahydrofuran-3-yl)pyrimidine-5-carboxamide (Compound D), optionally, in combination with an amount of another compound(s), that treats the particular disease, condition, or disorder described herein. 4-(4-(1-Isopropyl-7-oxo-1,4,6,7-tetrahydrospiro[indazole-5,4'-piperidine]-1'-carbonyl)-6-methoxypyridin-2-yl)benzoic acid is a selective ACC inhibitor and was prepared as the free acid in Example 9 of U.S. Pat. No. 8,859,577, which is the U.S. national phase of International Application No. PCT/IB2011/054119, all of which are hereby incorporated herein by reference in their entireties for all purposes. Crystalline forms of the compound are described in International patent application no. PCT/IB2018/058966, published as WO 2019/102311 on 31 May 2019.

(S)-2-(5-((3-Ethoxypyridin-2-yl)oxy)pyridin-3-yl)-N-(tetrahydrofuran-3-yl)pyrimidine-5-carboxamide is a DGAT2 inhibitor and is Example 1 in US Published Patent Application US 2018-0051012A1 which is hereby incorporated herein by reference in its entirety for all purposes.

The term "treating", "treat" or "treatment" as used herein embraces preventative, i.e., prophylactic; palliative treatment, i.e., relieve, alleviate, or slow the progression of the patient's disease (or condition) or any tissue damage associated with the disease (or condition); and reversal where the patient's disease (or condition) is not only alleviated but any tissue damage associated with the disease (or condition) is placed in a better state then when treatment was initiated. This latter could occur, for example and not limitation, from any one or more of the following: demonstration of NASH resolution and/or from an improvement in the fibrosis score based on liver biopsy; lower incidence of progression to cirrhosis, hepatocellular carcinoma, and/or other liver related outcomes; a reduction or improvement of the level of serum or imaging based markers of nonalcoholic steatohepatitis activity; reduction or improvement of nonalcoholic steatohepatitis disease activity; or reduction in the medical consequences of nonalcoholic steatohepatitis.

It appears that the administration of an ACC inhibitor may have positive effects to lower hepatic TGs and potentially other beneficial effects on treatment of NASH. Increases in circulating TG levels has been reported to be a mechanistic consequence of hepatic ACC inhibition (Kim et al, 2017), though doses of ACC inhibitors that only partially inhibit DNL may not produce elevations in circulating TGs (Bergman et al., (2018) *J. of Hepatology*, Volume 68, S582). WO2016/112305 provides methods of treating, stabilizing or lessening the severity or progression of a non-alcoholic fatty liver disease using an ACC inhibitor alone or with one or more additional therapeutic agents.

It has been discovered that administration of 4-(4-(1-isopropyl-7-oxo-1,4,6,7-tetrahydrospiro[indazole-5,4'-piperidine]-1'-carbonyl)-6-methoxypyridin-2-yl)benzoic acid, optionally administered as a pharmaceutically acceptable salt, has a potential to result in elevations in circulating TGs (generally measured from plasma) in Western diet fed Sprague Dawley rats as was observed in human subjects.

The compounds of the invention may contain asymmetric or chiral centers, and, therefore, exist in different stereoisomeric forms. Unless specified otherwise, it is intended that all stereoisomeric forms of the compounds of the invention as well as mixtures thereof, including racemic mixtures, form part of the invention. In addition, the invention embraces all geometric and positional isomers. For example, if a compound of the invention incorporates a double bond or a fused ring, both the cis- and trans-forms, as well as mixtures, are embraced within the scope of the invention.

Chiral compounds of the invention (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Where the compounds of the invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the invention possess one or more stereogenic centers and no stereochemistry is given in the name or structure, it is understood that the name or structure is intended to encompass all forms of the compound, including the racemic form.

It is also possible that the intermediates and compounds of the invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations.

Valence tautomers include interconversions by reorganization of some of the bonding electrons.

Included within the scope of the claimed compounds invention are all stereoisomers, geometric isomers and tautomeric forms of the compounds of the invention, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The invention includes all pharmaceutically acceptable isotopically-labelled compounds of the invention wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I, $^{124}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Tomography (PET) studies for examining substrate receptor occupancy.

Isotopically-labelled compounds of the invention can generally be prepared by conventional techniques known to those skilled in the art or by processes analogous to those described in the accompanying Examples and Preparations using an appropriate isotopically-labelled reagents in place of the non-labelled reagent previously employed.

The compounds of the invention may be isolated and used per se, or when possible, in the form of its pharmaceutically acceptable salt. The term "salts" refers to inorganic and organic salts of a compound of the invention. These salts can be prepared in situ during the final isolation and purification of a compound, or by separately treating the compound with a suitable organic or inorganic acid or base and isolating the salt thus formed. The acids which are used to prepare the pharmaceutically acceptable acid addition salts of the aforementioned base compounds of this invention are those which form non-toxic acid addition salts, (i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, naphthylate, mesylate, glucoheptonate, lactobionate, laurylsulphonate, hexafluorophosphate, benzene sulfonate, tosylate, formate, trifluoroacetate, oxalate, besylate, palmitiate, pamoate, malonate, stearate, laurate, malate, borate, p-toluenesulfonate and pamoate (i.e., 1,1'-methylene-bis-(2-hydroxy-3-naphthoate)) salts.

The invention also relates to base addition salts of the compounds of the invention. The chemical bases that may be used as reagents to prepare pharmaceutically acceptable base salts of those compounds of the invention that are acidic in nature are those that form non-toxic base salts with such compounds. Such non-toxic base salts include, but are not limited to those derived from such pharmacologically acceptable cations such as alkali metal cations (e.g., lithium, potassium and sodium) and alkaline earth metal cations e, calcium and magnesium), ammonium or water-soluble amine addition salts such as N-methylglucamine-(meglumine), tetramethylammonium, tetraethylammonium, methylamine, dimethylamine, trimethylamine, triethylamine, ethylamine, and the lower alkanolammonium and other base salts of pharmaceutically acceptable organic amines. See e.g. Berge, et al. *J. Pharm. Sci.* 66, 1-19 (1977).

Certain compounds of the invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the invention followed by gradual or fast cooling. The presence of polymorphs may be determined by solid probe NMR spectroscopy, IR spectroscopy, differential scanning calorimetry, powder X-ray diffraction or such other techniques.

In one embodiment, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with at least 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, each present in therapeutically effective amounts, in admixture with a pharmaceutically acceptable excipient.

In a further embodiment, the composition further comprises at least one additional pharmaceutical agent selected from the group consisting of an anti-inflammatory agent, an anti-diabetic agent, and a cholesterol/lipid modulating agent.

In a further embodiment, the composition further comprises at least one additional pharmaceutical agent selected from the group consisting of [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid; 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid; or 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

In further embodiment, the pharmaceutical composition contains (S)-2-(5-((3-ethoxypyridin-2-yl)oxy)pyridin-3-yl)-N-(tetrahydrofuran-3-yl)pyrimidine-5-carboxamide as a crystalline solid of structure:

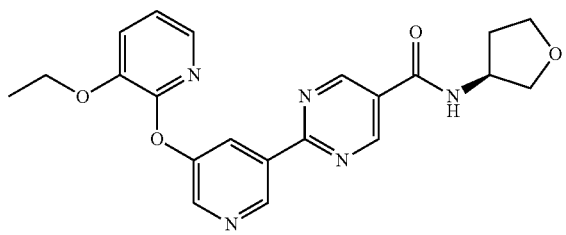 [SMILES: CCOc1cccnc1Oc1cncc(-c2ncc(C(=O)N[C@H]3CCOC3)cn2)c1]

or a pharmaceutically acceptable salt thereof.

In a further embodiment, the crystalline solid has a powder x-ray Diffraction pattern comprising 2-theta values of (CuKα radiation, wavelength of 1.54056 Å) 5.3±0.2, 7.7±0.2, and 15.4±0.2.

In a further embodiment, the crystalline solid has a powder x-ray diffraction pattern comprising 2-theta values of (CuKα radiation, wavelength of 1.54056 Å) 6.5±0.2, 9.3±0.2, and 13.6±0.2.

In a further embodiment, the pharmaceutical composition contains 4-(4-(1-Isopropyl-7-oxo-1,4,6,7-tetrahydrospiro [indazole-5,4'-piperidine]-1'-carbonyl)-6-methoxypyridin-2-yl)benzoic acid, or a pharmaceutically acceptable salt thereof, as a crystalline solid of structure:

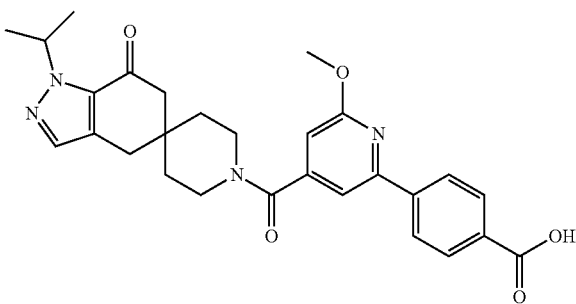 [SMILES: COc1cc(C(=O)N2CCC3(CC2)CC(=O)c2c(cnn2C(C)C)C3)cc(-c2ccc(C(=O)O)cc2)n1]

or a pharmaceutically acceptable salt thereof.

In a further embodiment, the crystalline solid is 2-amino-2-(hydroxymethyl)propane-1,3-diol salt of 4-(4-(1-isopropyl-7-oxo-1,4,6,7-tetrahydrospiro[indazole-5,4'-piperidine]-1'-carbonyl)-6-methoxypyridin-2-yl)benzoic acid.

In a further embodiment, the pharmaceutical composition further comprises at least one additional pharmaceutical agent selected from the group consisting of [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid; 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid; or 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

In another embodiment, the present invention is directed to a method of treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a patient in need of such treatment a therapeutically effective amount of S)-2-(5-((3-ethoxypyridin-2-yl)oxy)pyridin-3-yl)-N-(tetrahydrofuran-3-yl)pyrimidine-5-carboxamide, or a pharmaceutically acceptable salt thereof, in combination with at least a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid, or a pharmaceutically acceptable salt thereof.

In a further embodiment, the disease or condition is fatty liver. In another embodiment, the disease or condition is nonalcoholic fatty liver disease. In another embodiment, the disease or condition is nonalcoholic steatohepatitis. In another embodiment, the disease or condition is nonalcoholic steatohepatitis with liver fibrosis. In another embodiment, the disease or condition is nonalcoholic steatohepatitis with cirrhosis. In another embodiment, the disease or condition is nonalcoholic steatohepatitis with cirrhosis and with hepatocellular carcinoma. In another embodiment, the disease or condition is nonalcoholic steatohepatitis with cirrhosis and with a metabolic-related disease.

In a further embodiment, the method includes at least one other pharmaceutical agent, wherein the agent is selected from the group consisting of an acetyl-CoA carboxylase- (ACC) inhibitor, a diacylglycerol O-acyltransferase 1 (DGAT-1) inhibitor, monoacylglycerol O-acyltransferase inhibitors, a phosphodiesterase (PDE)-10 inhibitor, an AMPK activator, a sulfonylurea, a meglitinide, an α-amylase inhibitor, an α-glucoside hydrolase inhibitor, an α-glucosidase inhibitor, a PPARγ agonist, a PPAR α/γ agonist, a biguanide, a glucagon-like peptide 1 (GLP-1) modulator, liraglutide, albiglutide, exenatide, albiglutide, lixisenatide, dulaglutide, semaglutide, a protein tyrosine phosphatase-1B (PTP-1B) inhibitor, SIRT-1 activator, a dipeptidyl peptidase IV (DPP-IV) inhibitor, an insulin secreatagogue, a fatty acid oxidation inhibitor, an A2 antagonist, a c-jun amino-terminal kinase (JNK) inhibitor, glucokinase activators (GKa), insulin, an insulin mimetic, a glycogen phosphorylase inhibitor, a VPAC2 receptor agonist, SGLT2 inhibitors, a glucagon receptor modulator, GPR119 modulators, FGF21 derivatives or analogs, TGR5 receptor modulators, GPBAR1 receptor modulators, GPR40 agonists, GPR120 modulators, high affinity nicotinic acid receptor (HM74A) activators, SGLT1 inhibitors, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors, inhibitors or modulators of PDHK2 or PDHK4, inhibitors of MAP4K4, modulators of IL1 family including IL1beta, HMG-CoA reductase inhibitors, squalene synthetase inhibitors, fibrates, bile acid sequestrants, ACAT inhibitors, MTP inhibitors, lipooxygenase inhibitors, cholesterol absorption inhibitors, PCSK9 modulators, cholesteryl ester transfer protein inhibitors and modulators of RXRalpha.

In a further embodiment, the method includes at least one other pharmaceutical agent, wherein the agent is selected from the group consisting of cysteamine or a pharmaceutically acceptable salt thereof, cystamine or a pharmaceutically acceptable salt thereof, an anti-oxidant compound, lecithin, vitamin B complex, a bile salt preparations, an antagonists of Cannabinoid-1 (CB1) receptor, an inverse agonists of Cannabinoid-1 (CB1) receptor, a peroxisome proliferator-activated receptor) activity regulators, a benzothiazepine or benzothiepine compound, an RNA antisense construct to inhibit protein tyrosine phosphatase PTPRU, a heteroatom-linked substituted piperidine and derivatives thereof, an azacyclopentane derivative capable of inhibiting stearoyl-coenzyme alpha delta-9 desaturase, acylamide compound having secretagogue or inducer activity of adiponectin, a quaternary ammonium compound, Glatiramer acetate, pentraxin proteins, a HMG-CoA reductase inhibitor, n-acetyl cysteine, isoflavone compound, a macrolide antibiotic, a galectin inhibitor, an antibody, or any combination of thereof.

In a further embodiment, the method includes at least one other pharmaceutical agent, wherein the agent is selected from the group consisting of [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid; 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid; or 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

In another embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with at least a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof.

In a further embodiment, the method includes at least one other pharmaceutical agent, wherein the agent is selected from the group consisting of [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid; 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid; or 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

In another embodiment, the present invention is directed to a method for treating fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and with hepatocellular carcinoma in humans comprising the step of administering to a human in need of such treatment a therapeutically effective amount of two separate pharmaceutical compositions comprising
  i. a first composition that includes (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, present in a therapeutically effective amount, in admixture with a pharmaceutically acceptable excipient;
  ii. a second composition that includes 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, present in a therapeutically effective amount, in admixture with a pharmaceutically acceptable excipient; and optionally
  iii. a third composition comprising at least one additional pharmaceutical agent selected from the group consisting of an anti-inflammatory agent, an anti-diabetic agent, an anti-fibrotic agent, an anti-steatiotic agent, and a cholesterol/lipid modulating agent and an anti-diabetic agent, and a pharmaceutically acceptable excipient.

In a further embodiment, the said first composition and said second composition are administered simultaneously. In another embodiment, the composition comprises the first composition, the second composition, and the third composition.

In a further embodiment, the method includes a third composition wherein the at least one other pharmaceutical agent is selected from the group consisting of [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid; 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid; or 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

In another embodiment of the present invention, (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, is present in a pharmaceutical composition in a therapeutically effective amount, in admixture with a pharmaceutically acceptable excipient.

In another embodiment of the present invention, (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with at least 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, is present in a pharmaceutical composition in a therapeutically effective amount, in admixture with a pharmaceutically acceptable excipient.

In another embodiment of the present invention, the composition further includes at least one additional pharmaceutical agent selected from the group consisting of a GLP-1R agonist, a KHK inhibitor, an FXR agonist, an anti-inflammation agent, an anti-diabetic agent, an anti-fibrotic agent, an anti-steatiotic agent, and a cholesterol/lipid modulating agent.

In another embodiment, the method for treating a metabolic or metabolic-related disease, condition or disorder includes the step of administering to a patient a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof.

In another embodiment, the method for treating a condition selected from the group consisting of hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertriglyceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), non-alcoholic fatty liver disease (NAFLD), includes the administration of a therapeutically effective amount of Compound A, or a pharmaceutically acceptable salt thereof, and a therapeutically effective amount of Compound D, or a pharmaceutically acceptable salt thereof.

In a further embodiment, the method for treating a metabolic or metabolic-related disease, condition or disorder includes the step of administering to a patient in need of such treatment at least two separate pharmaceutical compositions comprising
  (i) a first composition that includes (S)-2-(5-((3-ethoxypyridin-2-yl)oxy)pyridin-3-yl)-N-(tetrahydrofuran-3-yl)pyrimidine-5-carboxamide, or a pharmaceutically acceptable salt thereof, present in a therapeutically effective amount, in admixture with a pharmaceutically acceptable excipient;
  (ii) a second composition that includes 4-(4-(1-Isopropyl-7-oxo-1,4,6,7-tetrahydrospiro[indazole-5,4'-piperidine]-1'-carbonyl)-6-methoxypyridin-2-yl)benzoic acid, or a pharmaceutically acceptable salt thereof, present in a therapeutically effective amount, in admixture with a pharmaceutically acceptable excipient; and optionally
  (iii) a third composition comprising at least one additional pharmaceutical agent selected from the group consisting of a GLP-1R agonist, a KHK inhibitor, an FXR agonist, an anti-inflammatory agent, an anti-diabetic agent, an anti-fibrotic agent, an anti-steatiotic agent, and a cholesterol/lipid modulating agent and an anti-diabetic agent, and a pharmaceutically acceptable excipient.

In yet a further embodiment, the method of the invention is performed when said first composition, said second composition, and said third composition are administered simultaneously.

In yet another embodiment, the method of the invention is performed when first composition, said second composition, and said third composition are administered sequentially and in any order.

In one embodiment, when three agents are administered, the first agent and the second agent are administered simultaneously and the third agent is administered sequentially. In another embodiment, the three separate agents are administered sequentially and in any order.

In one embodiment, when three agents are administered, the third agent comprises a GLP-1R agonist. The GLP-1R agonist 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid or a pharmaceutically salt thereof [such as its 2-amino-2-(hydroxymethyl)propane-1,3-diol salt, also known as its tris salt], as well as other GLP-1R agonists and the methods for making these compounds are described in U.S. Pat. No. 10,208,019, the disclosure of which is hereby incorporated by reference herein in its entirety for all purposes.

In certain embodiments the GLP-1R agonist is selected from the group consisting of liraglutide, albiglutide, exenatide, albiglutide, lixisenatide, dulaglutide, semaglutide, HM15211, LY3298176, Medi-0382, NN-9924, TTP-054, TTP-273, efpeglenatide, those described in WO2018109607, and DIAST-X2.

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier, et al. *Biodrugs*. 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll T, et al. *Diabetes*. 2001. 50; 609-613).

Hoist (*Physiol. Rev.* 2007, 87, 1409) and Meier (*Nat. Rev. Endocrinol.* 2012, 8, 728) describe that GLP-1 receptor agonists, such as GLP-1, liraglutide and exendin-4, have 3 major pharmacological activities to improve glycemic control in patients such as those with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

In another embodiment, when three agents are administered, the third agent comprises a KHK inhibitor.

In certain embodiments the KHK inhibitor is [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid or pharmaceutically acceptable salts thereof. [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid (including a crystalline free acid form thereof) is a ketohexokinase inhibitor and is described in Example 4 of U.S. Pat. No. 9,809,579, the disclosure of which is hereby incorporated herein by reference in its entirety for all purposes.

In certain embodiments, the KHK inhibitor is a crystalline free acid form of [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid.

Ketohexokinase (KHK) is the principal enzyme in fructose metabolism and catalyzes the conversion of fructose to fructose-1-phosphate (F1P). KHK is expressed as two alternative mRNA splice variants, denoted KHKa and KHKc, resulting from alternative splicing of the third exon. The affinity and capacity of KHKc for fructose phosphorylation is much greater than KHKa as evidenced by a much lower Km (Ishimoto, Lanaspa et al., *PNAS* 109, 4320-4325, 2012). While KHKa is ubiquitously expressed, the expression of KHKc is highest in the liver, kidney and intestines, the primary sites of fructose metabolism in the body (Diggle C P, et al. (2009) *J Histochem Cytochem* 57:763-774; Ishimoto, Lanaspa, et al., *PNAS* 109, 4320-4325, 2012). Additionally, loss of function mutations have been reported in humans and termed Essential Fructosuria (OMIM #229800), with no adverse effects except the appearance of fructose in the urine after ingestion of the sugar.

A more severe condition involved in fructose metabolism is Hereditary Fructose Intolerance (HFI, OMIM #229600) which is caused by defects in aldolase B (GENE: ALDOB) which is the enzyme responsible for breaking down F1P and is immediately downstream of the KHK step in the pathway (Bouteldja N, et. al, *J. Inherit. Metab. Dis.* 2010 April; 33(2):105-12; Tolan, D R, *Hum Mutat.* 1995; 6(3):210-8; http://www.omim.org/entry/229600). It is a rare disorder which affects an estimated 1 in 20,000 people, and mutations result in accumulation of F1P, depletion of ATP, and increase in uric acid, the combination of which causes hypoglycemia, hyperuricemia, and lactic acidosis, among other metabolic derangements. HFI impairs the body's ability to metabolize dietary fructose resulting in acute symptoms such as vomiting, severe hypoglycemia, diarrhea, and abdominal distress, leading to long term growth defects, liver and kidney damage and potentially death (Ali M et al, *J. Med. Genet.* 1998 May:35(5):353-65). Patients generally suffer through the first years of life prior to diagnosis, and the only course of treatment is avoiding fructose in the diet. This is made challenging by the presence of this macronutrient in a majority of food items. In addition to physical symptoms, many patients experience emotional and social isolation as a consequence of their unusual diet, and constantly struggle to adhere to strict dietary limitations (HFI-INFO Discussion Board, http://hfiinfo.proboards.com. Accessed 14 Dec. 2015). Even when they appear non-symptomatic, some patients develop NAFLD and kidney disease, which underscores the inadequacy of self-imposed dietary restriction as the only treatment option, and the high unmet medical need for this condition.

In hyperglycemic conditions, endogenous fructose production occurs through the polyol pathway, a pathway by which glucose is converted to fructose with sorbitol as an intermediate.

The activity of this pathway increases with hyperglycemia. In these studies, the authors demonstrated that the KHK null mice were protected from glucose induced weight gain, insulin resistance and hepatic steatosis suggesting that under hyperglycemic conditions, endogenously produced fructose may contribute to insulin resistance and hepatic steatosis (Lanaspa, M. A., et al., Nature Comm. 4, 2434, 2013). Therefore, the inhibition of KHK is anticipated to benefit many diseases where alterations of either or both of endogenous or ingested fructose are involved.

In another embodiment, when three agents are administered, the third agent comprises an FXR agonist. In certain embodiments the FXR agonist is selected from the group consisting of tropifexor (2-[((1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid) ("Tropifexor"); cilofexor (GS-9674); obeticholic acid; LY2562175; Met409; TERN-101; and EDP-305 and pharmaceutically acceptable salts thereof. The FXR agonist Tropifexor or a pharmaceutically acceptable salt thereof is described in, e.g., Example 1-1B of U.S. Pat. No. 9,150,568, the disclosure of which is hereby incorporated herein by reference in its entirety for all purposes. The chemical name of Tropifexor is 2-[((1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid.

The farnesoid X receptor (FXR) is a member of the nuclear hormone receptor superfamily and is primarily expressed in the liver, kidney and intestine (see, e.g., Seol et al. (1995) Mol. Endocrinol. 9:72-85 and Forman et al. (1995) Cell 81:687-693). It functions as a heterodimer with the retinoid X receptor (RXR) and binds to response elements in the promoters of target genes to regulate gene transcription. The FXR-RXR heterodimer binds with highest affinity to an inverted repeat-1 (IR-1) response element, in which consensus receptor-binding hexamers are separated by one nucleotide. FXR is part of an interrelated process, in that FXR is activated by bile acids (the end product of cholesterol metabolism) (see, e.g., Makishima et al. (1999) Science 284: 1362-1365, Parks et al. (1999) Science 284: 1365-1368, Wang et al. (1999) Mol. Cell. 3:543-553), which serve to inhibit cholesterol catabolism. See also, Urizar et al. (2000) J. Biol. Chem. 275:39313-39317.

FXR is a key regulator of cholesterol homeostasis, triglyceride synthesis and lipogenesis. (Crawley, Expert Opinion Ther. Patents (2010), 20(8): 1047-1057). In addition to the treatment of dyslipidemia, multiple indications for FXR have been described, including treatment of liver disease, diabetes, vitamin D-related diseases, drug-induced side effects and hepatitis. (Crawley, supra). While advances have been made in the development of novel FXR agonists, significant room for improvement remains.

In certain other embodiments, when three agent are administered, the third agent comprises an SGLT2 inhibitor, metformin, incretin analogs, an incretin receptor modulator, a DPP-4 inhibitor, or a PPAR agonist.

In certain other embodiments, when three agents are administered, the third agent is an antidiabetic agent selected from metformin, sitagliptin, or ertugliflozin.

In certain other embodiments, when three agents are administered, the third agent is an anti-heart failure agent selected from an ACE inhibitor, an angiotensin receptor blocker, a calcium channel blocker or a vasodilator.

The present invention further comprises kits that are suitable for use in performing the methods of treatment described above. In one embodiment, the kit contains a first dosage form comprising one or more of the agents (compounds) or a pharmaceutically acceptable salt thereof of the present invention and a container for the dosage, in quantities sufficient to carry out the methods of the present invention.

In another embodiment, the kit contains a first dosage form comprising one of the agents (compounds) or a pharmaceutically acceptable salt thereof of the present invention and a container for the first dosage, and a second dosage form comprising another agent (compound) or a pharmaceutically acceptable salt thereof of the present invention and a container for the second dosage form, wherein both dosage forms are in quantities sufficient to carry out the methods of the present invention.

In another embodiment, the kit contains a first dosage form comprising one of the agents (compounds) or a pharmaceutically acceptable salt thereof of the present invention and a container for the first dosage, a second dosage form comprising another agent (compound) or a pharmaceutically acceptable salt thereof of the present invention and a container for the second dosage forms, and a third dosage form comprising another agent (compound) or a pharmaceutically acceptable salt thereof of the present invention and a container for the third dosage form, wherein all three dosage forms are in quantities sufficient to carry out the methods of the present invention.

In certain embodiments of the present invention, there is provided a kit that comprises a first dosage form comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof a container for the first dosage form, and a second dosage form comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and a container for the second dosage form, wherein both dosage forms are in quantities sufficient to carry out the methods of the present invention.

In another embodiment of the present invention, there is provided a kit that comprises a first dosage form comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof a container for the first dosage, a second dosage form comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and a container for the second dosage forms and a third dosage form comprising another agent (compound) or a pharmaceutically acceptable salt thereof and a container for the third dosage form, wherein all three dosage forms are in quantities sufficient to carry out the methods of the present invention.

In some embodiments, the dosage form(s) of the kit can be administered simultaneously or chronologically staggered, that is at different time points and with equal or different time intervals for any of the dosage forms of the kit.

In any of the above-mentioned kits there may be provided a means for separately retaining each dosage form, such as a container, divided bottle, or divided foil packet. An example of such a kit is the familiar blister pack used for the packaging of tablets, capsules and the like. Such a kit is particularly suitable for administering different dosage forms, for example, oral and parenteral, for administering separate agents (compounds) at different dosage intervals, or for titrating the separate agent (compound) against one another. To assist compliance, the kit may comprises directions for administration and may be provided with a so-called memory aid.

The present invention also contemplates various other kits known to be utilized for the packaging, dispensing and administration of the agents (compounds) of the present invention. In a further embodiment, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, an HMG-CoA reductase inhibitor, and a pharmaceutically acceptable excipient.

In certain embodiments, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, an HMG-CoA reductase inhibitor selected from the group consisting of pravastatin, pitavastatin, lovastatin, atorvastatin, simvastatin, fluvastatin, itavastatin, nisvastatin, nisbastatin, rosuvastatin, atavastatin, and visastatin, and a pharmaceutically acceptable excipient.

In certain embodiments, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, atorvastatin, and a pharmaceutically acceptable excipient.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and an HMG-CoA reductase inhibitor. In certain embodiments, the HMG-CoA reductase inhibitor is atorvastatin.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and an HMG-CoA reductase inhibitor. In certain embodiments, the HMG-CoA reductase inhibitor is atorvastatin.

In a further embodiment, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, a fibrate agent, and a pharmaceutically acceptable excipient.

In a certain embodiments, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, a fibrate agent selected from the group consisting of gemfibrozil, fenofibrate, and clofibrate, and a pharmaceutically acceptable excipient.

In a certain embodiments, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, fenofibrate, and a pharmaceutically acceptable excipient.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and a fibrate agent. In certain embodiments, the fibrate agent is fenofibrate.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and fibrate agent. In certain embodiments, the fibrate agent is fenofibrate.

In a further embodiment, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, a bile acid sequestrant, and a pharmaceutically acceptable excipient.

In certain embodiments, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, a bile acid sequestrant selected from the group consisting of questran, colestipol, and colesevelam, and a pharmaceutically acceptable excipient.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and a bile acid sequestrant.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and a bile acid sequestrant.

In a further embodiment, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, a cholesterol absorption inhibitor, and a pharmaceutically acceptable excipient. In certain embodiments, the cholesterol absorption inhibitor is ezetimibe.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and a cholesterol absorption inhibitor.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and a cholesterol absorption inhibitor.

In a further embodiment, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, a nicotinic acid agent, and a pharmaceutically acceptable excipient.

In certain embodiments, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, a nicotinic acid agent selected from the group consisting of niacin, niacor, and slo-niacin, and a pharmaceutically acceptable excipient.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and a nicotinic acid agent.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and nicotinic acid agent.

In a further embodiment, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, a PCSK9 modulator, and a pharmaceutically acceptable excipient.

In certain embodiments, the present invention is directed to a pharmaceutical composition comprising 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, a PCSK9 modulator selected from the group consisting of alirocumab and evolucumab, and a pharmaceutically acceptable excipient.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and a PCSK9 modulator.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof and a PCSK9 modulator.

In any of the preceding embodiments, the 4-(4-(1-Isopropyl-7-oxo-1,4,6,7-tetrahydrospiro[indazole-5,4'-piperidine]-1'-carbonyl)-6-methoxypyridin-2-yl)benzoic acid is a crystalline solid. In certain embodiments, the crystalline solid is 2-amino-2-(hydroxymethyl)propane-1,3-diol salt of 4-(4-(1-isopropyl-7-oxo-1,4,6,7-tetrahydrospiro[indazole-5,4'-piperidine]-1'-carbonyl)-6-methoxypyridin-2-yl)benzoic acid.

In a further embodiment, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, an HMG-CoA reductase inhibitor, and a pharmaceutically acceptable excipient.

In certain embodiments, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, an HMG-CoA reductase inhibitor selected from the group consisting of pravastatin, pitavastatin, lovastatin, atorvastatin, simvastatin, fluvastatin, itavastatin, nisvastatin, nisbastatin, rosuvastatin, atavastatin, and visastatin, and a pharmaceutically acceptable excipient.

In certain embodiments, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, atorvastatin, and a pharmaceutically acceptable excipient.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof and an HMG-CoA reductase inhibitor. In certain embodiments, the HMG-CoA reductase inhibitor is atorvastatin.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of (S)-2-(5-((3-ethoxypyridin-2-yl)oxy) pyridin-3-yl)-N-(tetrahydrofuran-3-yl)pyrimidine-5-carboxamide or a pharmaceutically acceptable salt thereof and an HMG-CoA reductase inhibitor. In certain embodiments, the HMG-CoA reductase inhibitor is atorvastatin.

In a further embodiment, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, a fibrate agent, and a pharmaceutically acceptable excipient.

In a certain embodiments, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, a fibrate agent selected from the group consisting of gemfibrozil, fenofibrate, and clofibrate, and a pharmaceutically acceptable excipient.

In a certain embodiments, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, fenofibrate, and a pharmaceutically acceptable excipient.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of (S)-2-(5-((3-ethoxypyridin-2-yl)oxy)pyridin-3-yl)-N-(tetrahydrofuran-3- yl)pyrimidine-5-carboxamide or a pharmaceutically acceptable salt thereof and a fibrate agent. In certain embodiments, the fibrate agent is fenofibrate.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof and a fibrate agent. In certain embodiments, the fibrate agent is fenofibrate.

In a further embodiment, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, a bile acid sequestrant, and a pharmaceutically acceptable excipient.

In certain embodiments, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, a bile acid sequestrant selected from the group consisting of questran, colestipol, and colesevelam, and a pharmaceutically acceptable excipient.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof and a bile acid sequestrant.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof and a bile acid sequestrant.

In a further embodiment, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, a cholesterol absorption inhibitor, and a pharmaceutically acceptable excipient. In certain embodiments, the cholesterol absorption inhibitor is ezetimibe.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof and a cholesterol absorption inhibitor.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof and a cholesterol absorption inhibitor.

In a further embodiment, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, a nicotinic acid agent, and a pharmaceutically acceptable excipient.

In certain embodiments, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, a nicotinic acid agent selected from the group consisting of niacin, niacor, and slo-niacin, and a pharmaceutically acceptable excipient.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof and a nicotinic acid agent.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof and a nicotinic acid agent.

In a further embodiment, the present invention is directed to a pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, a PCSK9 modulator, and a pharmaceutically acceptable excipient.

In certain embodiments, the present invention is directed to a pharmaceutical composition comprising (S)-2-(5-((3-ethoxypyridin-2-yl)oxy)pyridin-3-yl)-N-(tetrahydrofuran-3- yl)pyrimidine-5-carboxamide or a pharmaceutically acceptable salt thereof, a PCSK9 modulator selected from the group consisting of alirocumab and evolucumab, and a pharmaceutically acceptable excipient.

In a further embodiment, the present invention is directed to a method for treating a disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, the method comprising administering to a human in need of such treatment a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof and a PCSK9 modulator.

In a further embodiment, the present invention is directed to a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a patient in need of such reduction a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof and a PCSK9 modulator.

In any of the preceding embodiments, the (S)-2-(5-((3-ethoxypyridin-2-yl)oxy)pyridin-3-yl)-N-(tetrahydrofuran-3-yl)pyrimidine-5-carboxamide is a crystalline solid. In certain embodiments, the crystalline solid has a powder x-ray Diffraction pattern comprising 2-theta values of (CuKα radiation, wavelength of 1.54056 Å) 5.3±0.2, 7.7±0.2, and 15.4±0.2. In certain other embodiments, the crystalline solid has a powder x-ray diffraction pattern comprising 2-theta values of (CuKα radiation, wavelength of 1.54056 Å) 6.5±0.2, 9.3±0.2, and 13.6±0.2.

Compounds of the invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database)). A preparation of (S)-2-(5-((3-ethoxypyridin-2-yl)oxy)pyridin-3-yl)-N-(tetrahydrofuran-3-yl)pyrimidine-5-carboxamide is presented in Example 1 of US 2018-0051012A1, hereby incorporated herein by reference in its entireties for all purposes. A preparation of 4-(4-(1-Isopropyl-7-oxo-1,4,6,7-tetrahydrospiro[indazole-5,4'-piperidine]-1'-carbonyl)-6-methoxypyridin-2-yl)benzoic acid is in Example 9 of U.S. Pat. No. 8,859,577, hereby incorporated herein by reference in its entireties for all purposes. Preparation of [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid (including a crystalline free acid form thereof) is described in Example 4 of U.S. Pat. No. 9,809,579. Preparation of GLP-1R agonists are described in U.S. Pat. No. 10,208,019.

Combination Agents

The compounds of the invention can be administered separately or together as separate agents or in a fixed-dose combination or in combination with one or more additional therapeutic agents. By "administered in combination" or "combination therapy" it is meant that Compound A and Compound D are administered together as the only two therapeutic agents or in combination with one or more additional therapeutic agents administered concurrently to the mammal being treated. When administered in combination, each component may be administered at the same time or sequentially in any order at different points in time. Thus, each component may be administered separately but sufficiently closely in time so as to provide the desired therapeutic effect. Thus, the methods of treatment described herein include use of combination agents to administer three or more agents in combination.

The combination agents are administered to a mammal in a therapeutically effective amount. By "therapeutically effective amount" it is meant an amount of the compounds of the invention that, when administered alone or in combination with an additional therapeutic agent to a mammal, is effective to treat the desired disease/condition e.g., NASH.

Preferred agents for the treatment of non-alcoholic steatohepatitis (NASH) and/or non-alcoholic fatty liver disease (NAFLD) (i.e., anti-NASH and anti-NAFLD agents) are an acetyl-CoA carboxylase (ACC) inhibitor, a ketohexokinase (KHK) inhibitor, a GLP-1 receptor agonist, an FXR agonist, a CB1 antagonist, an ASK1 inhibitor, an inhibitor of CCR2 and/or CCR5, a PNPLA3 inhibitor, a hydroxysteroid 17-β dehydrogenase (HSD17B13) inhibitor, a DGAT1 inhibitor, an FGF21 analog, an FGF19 analog, an SGLT2 inhibitor, a PPAR agonist, an AMPK activator, an SCD1 inhibitor or an MPO inhibitor. A commonly assigned patent application PCT/IB2017/057577 filed Dec. 1, 2017. is directed to GLP-1 receptor agonists. Most preferred are a FXR agonist, an apoptosis signal-regulating kinase 1 (ASK1) inhibitor, a PPAR agonist, a GLP-1 receptor agonist, a SGLT inhibitor, a an ACC inhibitor and a KHK inhibitor.

Given the NASH/NAFLD activity of the compounds of this invention, they may be co-administered with other agents for the treatment of non-alcoholic steatohepatitis (NASH) and/or non-alcoholic fatty liver disease (NAFLD) and associated disease/conditions, such as Orlistat, TZDs and other insulin-sensitizing agents, FGF21 analogs, Metformin, Omega-3-acid ethyl esters (e.g. Lovaza), Fibrates, HMG CoA-reductase Inhibitors, Ezetimibe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 inhibitors (including dapagliflozin, canagliflozin, empagliflozin, tofogliflozin, ertugliflozin, ASP-1941, THR1474, TS-071, ISIS388626 and LX4211 as well as those in WO2010023594), Phentermine, Topiramate, GLP-1 receptor agonists, GIP receptor agonists, dual GLP-1 receptor/glucagon receptor agonists (i.e., OPK88003, MED10382, JNJ-64565111, NN9277, BI 456906), dual GLP-1 receptor/GIP receptor agonists (i.e., Tirzepatide (LY3298176), NN9423), Angiotensin-receptor blockers an acetyl-CoA carboxylase (ACC) inhibitor, a BCKDK inhibitor, a ketohexokinase (KHK) inhibitor, ASK1 inhibitors, branched-chain alpha keto acid dehydrogenase kinase inhibitors (BCBK inhibitors), inhibitors of CCR2 and/or CCR5, PNPLA3 inhibitors, DGAT1 inhibitors, an FGF21 analog, FGF19 analogs, PPAR agonists, FXR agonists, AMPK activators, SCD1 inhibitors or MPO inhibitors.

Exemplary ACC inhibitors include 4-(4-[(1-isopropyl-7-oxo-1,4,6,7-tetrahydro-1'H-spiro[indazole-5,4'-piperidin]-1'-yl)carbonyl]-6-methoxypyridin-2-yl)benzoic acid; and firsocostat (GS-0976) and pharmaceutically acceptable salts thereof.

Exemplary DGAT2 inhibitors include (S)-2-(5-((3-ethoxypyridin-2-yl)oxy)pyridin-3-yl)-N-(tetrahydrofuran-3-yl)pyrimidine-5-carboxamide;
2-(5-((3-ethoxy-5-fluoropyridin-2-yl)oxy)pyridin-3-yl)-N-((3R,4S)-4-fluoropiperidin-3-yl)pyrimidine-5-carboxamide;
2-(5-((3-ethoxy-5-fluoropyridin-2-yl)oxy)pyridin-3-yl)-N-((3S,5S)-5-fluoropiperidin-3-yl)pyrimidine-5-carboxamide;
2-(5-((3-ethoxypyridin-2-yl)oxy)pyridin-3-yl)-N-((3R,4S)-4-fluoropiperidin-3-yl)pyrimidine-5-carboxamide;
2-(5-((3-ethoxypyridin-2-yl)oxy)pyridin-3-yl)-N-((3R,4R)-4-fluoropiperidin-3-yl)pyrimidine-5-carboxamide;
2-(5-((3-ethoxy-5-fluoropyridin-2-yl)oxy)pyridin-3-yl)-N-((3R,4R)-4-fluoropiperidin-3-yl)pyrimidine-5-carboxamide; and
2-(5-((3-ethoxypyridin-2-yl)oxy)pyridin-3-yl)-N-((3S,5S)-5-fluoropiperidin-3-yl)pyrimidine-5-carboxamide.

Examples of suitable anti-diabetic agents include (e.g. insulins, metformin, DPPIV inhibitors, GLP-1 receptor agonists, analogues and mimetics, SGLT1 and SGLT2 inhibitors). Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., Drug Discovery Today, 12(9/10): 373-381 (2007)), SIRT-1 activator (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), Ertugliflozin, ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4) 359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCα, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, 3 adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, the combination of naltrexone with buprorion and the like.

Preferred anti-obesity agents for use in the combinations of the invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as pegylated $PYY_{3-36}$ e.g., those described in US Publication 2006/0178501), opioid antagonists (e.g., naltrexone), the combination of naltrexone with buprorion, oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3), phentermine and topiramate (trade name: Qsymia), and sibutramine. Preferably, compounds of the invention and combination therapies are administered in conjunction with exercise and a sensible diet.

The compounds of the invention may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-CoA reductase inhibitors (e.g., pravastatin, pitavastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin); squalene synthetase inhibitors; fibrates (e.g., gemfibrozil, fenofibrate, clofibrate); bile acid sequestrants (such as questran, colestipol, colesevelam); ACAT inhibitors; MTP inhibitors; lipooxygenase inhibitors; cholesterol absorption inhibitors (e.g., ezetimibe); nicotinic acid agents (e.g., niacin, niacor, slo-niacin); omega-3 fatty acids; and cholesteryl ester transfer protein inhibitors. Other atherosclerotic agents include PCSK9 modulators (e.g., alirocumab and evolocumab).

In another embodiment, the compounds of the invention may be co-administered with agents for the treatment of non-alcoholic steatohepatitis (NASH) and/or non-alcoholic fatty liver disease (NAFLD), such as Orlistat, TZDs and other insulin sensitizing agents, FGF21 analogs, Metformin, Omega-3-acid ethyl esters (e.g. Lovaza), Fibrates, HMG CoA-reductase Inhibitors, Ezitimbe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buprorion, SGLT2 Inhibitors, Phentermine, Topiramate, Incretin (GLP and GIP) analogs and Angiotensin-receptor blockers.

In another embodiment, the additional pharmaceutical agent is selected from the group consisting of cysteamine or a pharmaceutically acceptable salt thereof, cystamine or a pharmaceutically acceptable salt thereof, an anti-oxidant compound, lecithin, vitamin B complex, a bile salt preparations, an antagonists of Cannabinoid-1 (CB1) receptor, an inverse agonists of Cannabinoid-1 (CB1) receptor, a peroxisome proliferator-activated receptor) activity regulators, a benzothiazepine or benzothiepine compound, an RNA antisense construct to inhibit protein tyrosine phosphatase PTPRU, a heteroatom-linked substituted piperidine and derivatives thereof, an azacyclopentane derivative capable of inhibiting stearoyl-coenzyme alpha delta-9 desaturase, acylamide compound having secretagogue or inducer activity of adiponectin, a quaternary ammonium compound, Glatiramer acetate, pentraxin proteins, a HMG-CoA reductase inhibitor, n-acetyl cysteine, isoflavone compound, a macrolide antibiotic, a galectin inhibitor, an antibody, or any combination of thereof.

Additional therapeutic agents include anti-coagulant or coagulation inhibitory agents, anti-platelet or platelet inhibitory agents, thrombin inhibitors, thrombolytic or fibrinolytic agents, anti-arrhythmic agents, anti-hypertensive agents, calcium channel blockers (L-type and T-type), cardiac glycosides, diruetics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, epinephrine, nitroglycerin, nitroprusside etc.

Combination agents useful for treating vasculitis are included, for example, azathioprine, cyclophosphamide, mycophenolate, mofetil, rituximab etc.

In another embodiment, the invention provides a combination wherein the third agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the invention include heparins (e.g., unfractioned and low molecular weight heparins such as enoxaparin and dalteparin).

In another preferred embodiment the third agent is at least one agent selected from warfarin, dabigatran, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

A preferred third agent is at least one anti-platelet agent. Especially preferred anti-platelet agents are aspirin and clopidogrel.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicylic acid or ASA) and COX-2 inhibitors such as CELEBREX or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, dabigatran, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrhythmic agents include: Class I agents (such as propafenone); Class II agents (such as metoprolol, atenolol, carvedilol and propranolol); Class III agents (such as sotalol, dofetilide, amiodarone, azimilide and ibutilide); Class IV agents (such as diltiazem and verapamil); $K^+$ channel openers such as $I_{Ach}$ inhibitors, and $I_{Kur}$ inhibitors (e.g., compounds such as those disclosed in WO01/40231).

The compounds of the present invention they may be co-administered with anti-heart failure agents such as ACE inhibitors (e.g. captopril, enalapril, fosinopril, Lisinopril, perindopril, quinapril, Ramipril, trandolapril), Angiotensin II receptor blockers (e.g., Candesartan, Losartan, Valsartan), Angiotensin-receptor neprilysin inhibitors (sacubitril/valsartan), $I_f$ channel blocker Ivabradine, Beta-Adrenergic blocking agents (e.g., bisoprolol, metoprolol succinate, carvedilol), Aldosterone antagonists (e.g., spironolactone, eplerenone), hydralazine and isosorbide dinitrate, diuretics (e.g., furosemide, bumetanide, torsemide, chlorothiazide, amiloride, hydrochlorothiazide, Indapamide, Metolazone, Triamterene), or digoxin.

The compounds of the invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, indapamide, metozolone, musolimine, bumetanide, triamterene, amiloride, spironolactone); renin inhibitors; ACE inhibitors (e.g., captopril, zofenopril, fosinopril, enalapril, ceranopril, cilazopril, delapril, pentopril, perindopril, quinapril, ramipril, trandolapril, lisinopril); AT-1 receptor antagonists (e.g., losartan, irbesartan, valsartan); Angiotensin-receptor neprilysin inhibitors (sacubitril/valsartan); Beta-Adrenergic blocking agents (e.g., bisoprolol, metoprolol succinate, carvedilol); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mibefradil.

Examples of suitable cardiac glycosides include digitalis and ouabain.

In one embodiment, the compounds of the invention may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, the compounds of the invention may be co-administered with a loop diuretic. In still another embodiment, the loop diuretic is selected from furosemide and torsemide. In still another embodiment, the compounds of the invention may be co-administered with furosemide. In still another embodiment, the compounds of the invention may be co-administered with torsemide which may optionally be a controlled or modified release form of torsemide.

In another embodiment, the compounds of the invention may be co-administered with a thiazide-type diuretic. In still another embodiment, the thiazide-type diuretic is selected from the group consisting of chlorothiazide and hydrochlorothiazide. In still another embodiment, the compounds of the invention may be co-administered with chlorothiazide. In still another embodiment, the compounds of the invention may be co-administered with hydrochlorothiazide.

In another embodiment, the compounds of the invention may be co-administered with a phthalimidine-type diuretic. In still another embodiment, the phthalimidine-type diuretic is chlorthalidone. Examples of suitable mineralocorticoid receptor antagonists include spironolactone and eplerenone. Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

Particularly when provided as a single dosage unit, the potential exists for a chemical interaction between the combined active ingredients. For this reason, when a first therapeutic agent and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that effects a sustained release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In combination therapy treatment, both the compounds of this invention and the other drug therapies are administered to mammals (e.g., humans, male or female) by conventional methods.

The dosage of each therapeutic agent, e.g., Compound A, Compound D, and any additional therapeutic agent, is generally dependent upon a number of factors including the health of the subject being treated, the extent of treatment desired, the nature and kind of concurrent therapy, if any, and the frequency of treatment and the nature of the effect desired. In general, the dosage range of each therapeutic agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of treatment of the invention, a compound of the invention or a combination of a compound of the invention and at least one additional pharmaceutical agent (referred to herein as a "combination") is administered to a subject in need of such treatment, preferably in the form of a pharmaceutical composition. In the combination aspect of the invention, the compound of the invention and at least one other pharmaceutical agent (e.g., another anti-obesity agent,) may be administered either separately or in a pharmaceutical composition comprising both. It is generally preferred that such administration be oral.

When a combination of a compound of the invention and at least one other pharmaceutical agent are administered together, such administration may be sequential in time or simultaneous. Simultaneous administration of drug combinations is generally preferred. For sequential administration, a compound of the invention and the additional pharmaceutical agent may be administered in any order. It is generally preferred that such administration be oral. It is especially preferred that such administration be oral and simultaneous. When a compound of the invention and the additional pharmaceutical agent are administered sequentially, the administration of each may be by the same or by different methods.

According to the methods of the invention, a compound of the invention or a combination is preferably administered in the form of a pharmaceutical composition. Accordingly, a compound of the invention or a combination can be administered to a patient separately or together in any conventional oral, rectal, transdermal, parenteral (e.g., intravenous, intramuscular or subcutaneous), intracisternal, intravaginal, intraperitoneal, topical (e.g., powder, ointment, cream, spray or lotion), buccal or nasal dosage form (e.g., spray, drops or inhalant).

The compounds of the invention or combinations can be administered alone but will generally be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md. 20.sup.th ed. 2000.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol®. brand caprylic/capric acid ester with glycerine or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multi-particulate preparations (granules). In such solid dosage forms, a compound of the invention or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-sol™), polyacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or (i) one or more lubricants (e.g., talc, calcium stearate, magnesium stearate, stearic acid, polyoxyl stearate, cetanol, talc, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the invention and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-di-sol™, Explotab™, starch and sodium lauryl sulphate. When present a disintegrant will usually comprise less than 10% of the formulation or less than 5%, for example about 3%. A preferred lubricant is magnesium stearate. When present a lubricant will usually comprise less than 5% of the formulation or less than 3%, for example about 1%.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of the invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyole™ (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyceride, from Gattefosse), Captex™ 500P (glyceryl triacetate i.e. triacetin, from Abitec), Capmul™ MCM (medium chain mono- and diglycerides, from Abitec), Migyol™ 812 (caprylic/capric triglyceride, from Condea, Cranford N.J.), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium chain (about $C_8$ to $C_{10}$) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of the invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the invention or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of the invention or combinations include ointments, creams, lotions, powders and sprays. The drugs are admixed with a pharmaceutically acceptable excipient, diluent or carrier, and any preservatives, buffers, or propellants that may be required.

When compounds are poorly soluble in water, e.g., less than about 1 µg/mL, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Water-soluble polymers suitable for use with the invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel$^{(R0-102)}$ (15.8%), sodium starch (7%), sodium lauryl sulfate (2%) and magnesium stearate (1%).

The HPMCAS polymers are available in low, medium and high grades as Aqoa$^{(R)-LF}$, Aqoat$^{(R)-MF}$ and Aqoat$^{(R)-HF}$ respectively from Shin-Etsu Chemical Co., LTD, Tokyo, Japan. The higher MF and HF grades are generally preferred.

The following paragraphs describe exemplary formulations, dosages, etc. useful for non-human animals. The administration of Compound A, or a pharmaceutically acceptable salt thereof, in combination with Compound D, or a pharmaceutically acceptable salt thereof, as the two agents or in combinations with another agent can be effected orally or non-orally.

An amount of Compound A, or a pharmaceutically acceptable salt thereof, with Compound D, or a pharmaceutically acceptable salt thereof, together or in combination with an another agent is administered such that an effective dose is received. Generally, a daily dose that is administered orally to an animal is between about 0.01 and about 1,000 mg/kg of body weight, e.g., between about 0.01 and about 300 mg/kg or between about 0.01 and about 100 mg/kg or between about 0.01 and about 50 mg/kg of body weight, or between about 0.01 and about 25 mg/kg, or about 0.01 and about 10 mg/kg or about 0.01 and about 5 mg/kg. A daily dose of Compound A that is administered may be 2 mg, 3 mg, 5 mg, 10 mg, 15 mg, 20 mg, 25 mg, 30 mg or 50 mg. The daily dose may be divided into multiple doses, such as a BID/Q12 hour dosing interval. For example, in certain instances the daily dose of Compound A may be administered as 15 mg q12 hours. A daily dose of Compound D that is administered may be 50 mg, 100 mg, 200 mg or 300 mg The daily dose may be divided into multiple doses, such as a BID/Q12 hour dosing interval. For example, in certain instances the daily dose of Compound D may be administered as 300 mg q12 hours.

Conveniently, a compound of the invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the invention (or combination) per ton of feed.

For parenteral administration in animals, the compounds of the invention (or combination) may be prepared in the form of a paste or a pellet and administered as an implant, usually under the skin of the head or ear of the animal in which increase in lean meat deposition and improvement in lean meat to fat ratio is sought.

Paste Formulations may be prepared by dispersing the drug in a pharmaceutically acceptable oil such as peanut oil, sesame oil, corn oil or the like.

Pellets containing a therapeutically effective amount of Compound A, or a pharmaceutically acceptable salt thereof, in combination with Compound D, or a pharmaceutically acceptable salt thereof, pharmaceutical composition, or combination may be prepared by admixing Compound A, or a pharmaceutically acceptable salt thereof, with Compound D, or a pharmaceutically acceptable salt thereof, with a diluent such as carbowax, carnuba wax, and the like, and a lubricant, such as magnesium or calcium stearate, may be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the invention yields leaner animals that command higher sale prices from the meat industry.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England) and Tyger Scientific (Princeton, N.J.). Certain common abbreviations and acronyms have been employed which may include: AcOH (acetic acid), DBU (1,8-diazabicyclo[5.4.0]undec-7-ene), CDI (1,1'-carbonyldiimidazole), DCM (dichloromethane), DEA (diethylamine), DIPEA (N,N-diisopropylethylamine), DMAP (4-dimethylaminopyridine), DMF (N,N'-dimethylformamide), DMSO (dimethylsulfoxide), EDCI (N-(3-dimethylaminopropyl)-N'-ethylcarbodiimide), $Et_2O$ (diethyl ether), EtOAc (ethyl acetate), EtOH (ethanol), G or g (gram), HATU (2-(1H-7-azabenzotriazol-1-yl)-1,1,3,3-tetramethyl uronium hexafluorophosphate methanaminium), HBTU (O-benzotriazol-1-yl-N,N,N'N'-tetramethyluronium hexafluoro phosphate), HOBT (1-hydroxybenzotriazole), H or h (hour), IPA (isopropyl alcohol), KHMDS (potassium hexamethyldisilazane), MeOH (methanol), L or l (liter), mL (milliliter) MTBE (tert-butyl methyl ether), mg (milligram), $NaBH(OAc)_3$ (sodium triacetoxyborohydride), NaHMDS (sodium hexamethyldisilazane), NMP (N-methylpyrrolidone), RH (relative humidity), RT or rt (room temperature which is the same as ambient temperature (about 20 to 25° C.)), SEM ([2-(Trimethylsilyl)ethoxy]methyl), TEA (triethylamine), TFA (trifluoroacetic acid), THF (tetrahydrofuran), and $T_3P$ (propane phosphonic acid anhydride).

$^1H$ Nuclear magnetic resonance (NMR) spectra were in all cases consistent with the proposed structures. Characteristic chemical shifts (δ) are given in parts-per-million (ppm) relative to the residual proton signal in the deuterated solvent ($CHCl_3$ at 7.27 ppm; $CD_2HOD$ at 3.31 ppm) and are reported using conventional abbreviations for designation of major peaks: e.g. s, singlet; d, doublet; t, triplet; q, quartet; m, multiplet; br, broad.

ssNMR means solid-state NMR.

PXRD means Powder X-ray Diffraction.

The term "substantially the same" when used to describe X-ray powder diffraction patterns is mean to include patterns in which peaks are within a standard deviation of +/−0.20 2Θ.

As used herein, the term "substantially pure" with reference to a particular crystalline form means that the crystalline form includes less than 10%, preferably less than 5%, preferably less than 3%, preferably less than 1% by weight of any other physical form of Compound A or Compound D.

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wis. or DriSolv™ products from EMD Chemicals, Gibbstown, N.J.) were employed. Commercial solvents and reagents were used without further purification. When indicated, reactions were heated by microwave irradiation using Biotage Initiator or Personal Chemistry Emrys Optimizer microwaves. Reaction progress was monitored using thin layer chromatography (TLC), liquid chromatography-mass spectrometry (LCMS), high performance liquid chromatography (HPLC), and/or gas chromatography-mass spectrometry (GCMS) analyses. TLC was performed on pre-coated silica gel plates with a fluorescence indicator (254 nm excitation wavelength) and visualized under UV light and/or with $I_2$, $KMnO_4$, $CoCl_2$, phosphomolybdic acid, and/or ceric ammonium molybdate stains. LCMS data were acquired on an Agilent 1100 Series instrument with a Leap Technologies autosampler, Gemini C18 columns, MeCN/water gradients, and either TFA, formic acid, or ammonium hydroxide modifiers. The column eluent was analyzed using Waters ZQ mass spectrometer scanning in both positive and negative ion modes from 100 to 1200 Da. Other similar instruments were also used. HPLC data were acquired on an Agilent 1100 Series instrument using Gemini or XBridge C18 columns, MeCN/water gradients, and either TFA or ammonium hydroxide modifiers. GCMS data were acquired using a Hewlett Packard 6890 oven with an HP 6890 injector, HP-1 column (12 m×0.2 mm×0.33 μm), and helium carrier gas. The sample was analyzed on an HP 5973 mass selective detector scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were performed by chiral supercritical fluid chromatography (SFC) using Berger or Thar instruments; ChiralPAK-AD, -AS, -IC, Chiralcel-OD, or -OJ columns; and $CO_2$ mixtures with MeOH, EtOH, iPrOH, or MeCN, alone or modified using TFA or $iPrNH_2$. UV detection was used to trigger fraction collection.

Mass spectrometry data are reported from LCMS analyses. Mass spectrometry (MS) was performed via atmospheric pressure chemical ionization (APCI), electrospray Ionization (ESI), electron impact ionization (EI) or electron scatter (ES) ionization sources. Proton nuclear magnetic spectroscopy ($^1H$ NMR) chemical shifts are given in parts per million downfield from tetramethylsilane and were recorded on 300, 400, 500, or 600 MHz Varian spectrometers. Chemical shifts are expressed in parts per million (ppm, b) referenced to the deuterated solvent residual peaks. The peak shapes are described as follows: s, singlet; d, doublet; t, triplet; q, quartet; quin, quintet; m, multiplet; br s, broad singlet; app, apparent. Analytical SFC data were acquired on a Berger analytical instrument as described above. Optical rotation data were acquired on a PerkinElmer model 343 polarimeter using a 1 dm cell. Silica gel chromatography was performed primarily using a medium pressure Biotage or ISCO systems using columns pre-packaged by various commercial vendors including Biotage and ISCO. Microanalyses were performed by Quantitative Technologies Inc. and were within 0.4% of the calculated values.

Unless otherwise noted, chemical reactions were performed at room temperature (about 23 degrees Celsius).

The compounds and intermediates described below were named using the naming convention provided with ChemBioDraw Ultra, Version 12.0 (CambridgeSoft Corp., Cambridge, Mass.). The naming convention provided with ChemBioDraw Ultra, Version 12.0 are well known by those skilled in the art and it is believed that the naming convention provided with ChemBioDraw Ultra, Version 12.0 generally comports with the IUPAC (International Union for Pure and Applied Chemistry) recommendations on Nomenclature of Organic Chemistry and the CAS Index rules. Unless noted otherwise, all reactants were obtained commercially without further purifications or were prepared using methods known in the literature.

The terms "concentrated", "evaporated", and "concentrated in vacuo" refer to the removal of solvent at reduced pressure on a rotary evaporator with a bath temperature less than 60° C. The abbreviation "min" and "h" stand for "minutes" and "hours" respectively. The term "TLC" refers to thin layer chromatography, "room temperature or ambient temperature" means a temperature between 18 to 25° C., "GCMS" refers to gas chromatography-mass spectrometry, "LCMS" refers to liquid chromatography-mass spectrometry, "UPLC" refers to ultra performance liquid chromatography and "HPLC" refers to high pressure liquid chromatography, "SFC" refers to supercritical fluid chromatography.

Hydrogenation may be performed in a Parr Shaker under pressurized hydrogen gas, or in Thales-nano H-Cube flow hydrogenation apparatus at full hydrogen and a flow rate between 1-2 mL/min at specified temperature.

HPLC, UPLC, LCMS, GCMS, and SFC retention times were measured using the methods noted in the procedures.

PREPARATION OF INTERMEDIATES AND EXAMPLES

Example 1 (DGAT2i Compound/Compound D): (S)-2-(5-((3-ethoxypyridin-2-yl)oxy)pyridin-3-yl)-N-(tetrahydrofuran-3-yl)pyrimidine-5-carboxamide

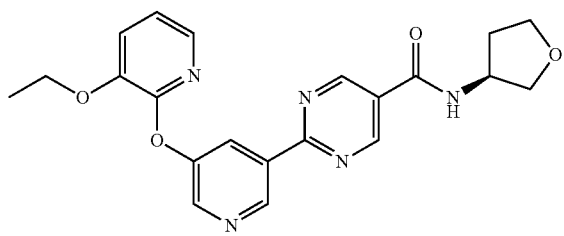 [SMILES: CCOc1cccnc1Oc1cncc(-c2ncc(C(=O)N[C@H]3CCOC3)cn2)c1]

Step 1: 3-Ethoxypyridine

Cesium carbonate (12 mol, 1.5 equiv) and ethyl iodide (9.7 mol, 1.2 equiv) were added to a solution of 3-hydroxypyrdine (8.10 mol, 1.0 equiv) in acetone (12 L) at 15° C. The reaction mixture was stirred at room temperature for 24 hours. The reaction mixture was filtered and the organic layer was concentrated to give crude product. Ethyl acetate (20 L) was added and washed with water (3×5 L). The organic layer was dried over sodium sulfate, filtered and concentrated to give 3-ethoxypyridine (620 g, 62%) as an oil. $^1$H NMR (400 MHz, CDCl$_3$) b 1.44 (t, 3H), 4.07 (q, 2H), 7.15-7.23 (m, 2H), 8.20 (dd, 1H), 8.30 (d, 1H).

Step 2: 3-Ethoxypyridine-1-oxide m-Chloroperoxybenzoic acid (6.5 mol, 1.3 equiv) was added to a solution of 3-ethoxypyridine (5.0 mol, 1.0 equiv) in dichloromethane (12 L) at 10° C. The reaction mixture was stirred at room temperature for 24 hours. Sodium thiosulfate (4 kg, in 5 L of water) was added. The reaction mixture was stirred at 15° C. for 2 hours. Another portion of sodium thiosulfate (1.5 kg, in 5 L of water) was added. The reaction mixture was stirred at 15° C. for 1 hour. The mixture was extracted with dichloromethane (16×10 L). The combined organic layers were concentrated to give crude product. The crude product was purified by silica gel column chromatography (dichloromethane:methanol; 100:1-10:1) to give the title compound (680 g, 97%) as brown oil. This was further purified by trituration with petroleum ether (4 L) at room temperature for 24 hours to give 3-ethoxypyridine-1-oxide (580 g, 83%) as yellow solid. $^1$H NMR (400 MHz, CDCl$_3$) b 1.41 (t, 3H), 4.02 (q, 2H), 6.84 (dd, 1H), 7.12 (dd, 1H), 7.85 (d, 1H), 7.91-7.95 (m, 1H).

Step 3: 2-((5-Bromopyridin-3-yl)oxy)-3-ethoxypyridine

This reaction was carried out in five parallel batches. Diisopropylethylamine (2.69 mol, 3.7 equiv) and bromotripyrrolidinophosphonium hexafluorophosphate (0.93 mol, 1.3 equiv) were added to a stirred solution of 3-ethoxypyridine-1-oxide (0.72 mol, 1.0 equiv) and 3-bromo-5-hydroxypyridine (0.72 mol, 1.0 equiv) in tetrahydrofuran (2500 mL) at room temperature. The reaction mixture was stirred at room temperature for 2 days then the separate batches were combined to a single batch. The resulting suspension was concentrated to dryness and dissolved in dichloromethane (25 L). The organic layer was washed with 1N sodium hydroxide (15 L), water (3×20 L), and brine (20 L). The organic layer was dried over sodium sulfate, filtered and concentrated to give an oil. The crude oil was purified by silica gel column chromatography (petroleum ether:ethyl acetate; 10:1-1:1) to give crude product as brown solid. This solid was triturated with methyl tert-butyl ether:petroleum ether (1:10; 11 L) to afford 2-((5-bromopyridin-3-yl)oxy)-3-ethoxypyridine (730 g, 69%) as off yellow solid. $^1$H NMR (400 MHz, CDCl$_3$) b 1.49 (t, 3H), 4.16 (q, 2H), 7.04 (dd, 1H), 7.25 (dd, 1H), 7.68-7.73 (m, 2H), 8.44 (d, 1H), 8.49 (d, 1H). MS (ES+) 297.1 (M+H).

Step 4: Ethyl 2-(5-((3-ethoxypyridin-2-yl)oxy)pyridin-3-yl)pyrimidine-5-carboxylate A solution of 2-((5-bromopyridin-3-yl)oxy)-3-ethoxypyridine (300 mmol, 1.0 equiv) in tetrahydrofuran (1.3 L) was degassed with nitrogen for 30 minutes. Turbo Grignard (390 mmol, 1.3 equiv, 1.3 M in tetrahydrofuran) was added at room temperature at a rate to maintain the internal temperature below 30° C. The reaction mixture was allowed to cool to room temperature and stirred for 3 hours. The reaction was cooled to 10° C. and zinc chloride (390 mmol, 1.3 equiv, 1.9 M in 2-methyltetrahydrofuran) was added at a rate to maintain the temperature below 15° C. The resulting suspension was warmed to room temperature until all the precipitate was dissolved and then cooled back to 10° C. Ethyl 2-chloropyrimidine-5-carboxylate (360 mmol, 1.2 equiv) and dichloro[bis(2-(diphenylphosphino)phenyl) ether]palladium(II) (6.00 mmol, 0.02 equiv) were added as solids. The resulting suspension was degassed with nitrogen for 30 minutes then heated to 50° C. for 16 hours. The reaction was worked up under aqueous conditions then treated sequentially with ethylenediaminetetraacetic acid disodium salt, thiosilica, and charcoal to remove metal impurities. The crude compound was recrystallized from methanol (450 mL) to yield ethyl 2-(5-((3-ethoxypyridin-2-yl)oxy)pyridin-3-yl)pyrimidine-5-carboxylate (77 g, 70%) as a pale, yellow solid. $^1$H NMR (400 MHz, CDCl$_3$) b 1.44 (t, 3H), 1.50 (t, 3H), 4.19 (q, 2H), 4.46 (q, 2H), 7.00-7.04 (m, 1H), 7.25 (s, 1H), 7.71 (d, 1H), 8.59 (s, 1H), 8.66 (d, 1H), 9.32 (s, 2H), 9.55 (s, 1H).

Step 5: 2-(5-((3-ethoxypyridin-2-yl)oxy)pyridin-3-yl)pyrimidine-5-carboxylic acid (Intermediate 1)

Sodium hydroxide (307 mmol, 1.5 equiv, 4M aqueous) and methanol (50 mL) were added to a suspension of 2-(5-((3-ethoxypyridin-2-yl)oxy)pyridin-3-yl)pyrimidine-5-carboxylate (205 mmol, 1.0 equiv) in tetrahydrofuran (300 mL). The resulting solution was stirred at room temperature for 3 hours. The reaction mixture was diluted with water (400 mL) and extracted with 2:1 diethyl ether:heptanes (2×300 mL). The aqueous layer was acidified to pH of 4 with 4M hydrochloric acid. The resulting suspension was stirred at room temperature for 1 hour. The solid was filtered, washed with water, and dried to yield 2-(5-((3-ethoxypyridin-2-yl)oxy)pyridin-3-yl)pyrimidine-5-carboxylic acid (69 g, 100%) as a pale, yellow solid. $^1$H NMR (400 MHz, DMSO-d$_6$) δ1.37 (t, 3H), 4.18 (q, 2H), 7.19 (dd, 1H), 7.58 (dd, 1H), 7.70 (dd, 1H), 8.35-8.40 (m, 1H), 8.66 (d, 1H), 9.33 (s, 2H), 9.41 (d, 1H), 13.9 (br. s, 1H).

Step 6: (S)-2-(5-((3-ethoxypyridin-2-yl)oxy)pyridin-3-yl)-N-(tetrahydrofuran-3-yl)pyrimidine-5-carboxamide (Example 1 (DGAT2i Compound))

Oxalyl chloride (13.8 mL, 160 mmol, 1.2 equiv) and dimethylformamide (0.510 mL, 6.65 mmol, 0.05 equiv) were added to a suspension of 2-(5-((3-ethoxypyridin-2-yl)oxy)pyridin-3-yl)pyrimidine-5-carboxylic acid (45.0 g, 133 mmol, 1.0 equiv) in dichloromethane (500 mL). The suspension was stirred for 2 hours when a solution was achieved. The reaction mixture was concentrated to yield crude acid chloride as a red solid. A solution of (S)-tetrahydrofuran-3-amine (12.2 g, 140 mmol, 1.05 equiv) and diisopropylethylamine (51.0 mL, 293 mmol, 2.2 equiv) in tetrahydrofuran (100 mL) was added dropwise to a solution of the crude acid chloride in dichloromethane (200 mL) at 0° C. The reaction was allowed to warm to room temperature and stirred for 16 hours. Water (1.0 L) and ethyl acetate (600 mL) were added and the organic layer was separated, washed with saturated sodium bicarbonate, dried over magnesium sulfate, and filtered. The filtrate was treated with activated charcoal (20 g) was stirred at 65° C. for 20 minutes. The suspension was filtered warm and filtrate was concentrated to a pale, yellow solid which was recrystallized from methanol in ethyl acetate (1:4, 1 L) to yield (S)-2-(5-((3-ethoxypyridin-2-yl)oxy)pyridin-3-yl)-N-(tetrahydrofuran-3-yl)pyrimidine-5-carboxamide (43.5 g, 81%) as a colorless solid. The title compound was combined with previous batches (108.7 g, 266.8 mmol) prepared in the same manner and slurried with ethyl acetate (1.0 L) at 80° C. for 4 hours. The suspension was allowed to cool to room temperature and stirred for 4 days. The solid was filtered, washed with ethyl acetate (3×200 mL) and dried under high vacuum at 50° C. for 24 hours to yield (S)-2-(5-((3-ethoxypyridin-2-yl)oxy)pyridin-3-yl)-N-(tetrahydrofuran-3-yl)pyrimidine-5-carboxamide (100.5 g, 92%) as a colorless solid. $^1$H NMR (300 MHz, DMSO-d$_6$) δ 1.38 (t, 3H), 1.89-1.98 (m, 1H), 2.15-2.26 (m, 1H), 3.65 (dd, 1H), 3.70-3.78 (m, 1H), 3.85-3.92 (m, 2H), 4.18 (q, 2H), 4.46-4.55 (m, 1H), 7.18 (dd, 1H), 7.58 (dd, 1H), 7.69 (dd, 1H), 8.37 (dd, 1H), 8.64 (d, 1H), 8.95 (d, 1H), 9.28 (s, 2H), 9.39 (d, 1H). MS (ES+) 408.4 (M+H). Melting point 177.5° C. Elemental analysis for $C_{21}H_{21}N_5O_4$: calculated C, 61.91; H, 5.20; N, 17.19; found C, 61.86; H, 5.18; N, 17.30.

The solid form from this procedure was characterized by Powder X-ray diffraction (PXRD) analysis and assigned as Form 1 of Compound D.

Alternative Step 6 for Preparation of (S)-2-(5-((3-ethoxypyridin-2-yl)oxy)pyridin-3-yl)-N-(tetrahydrofuran-3-yl)pyrimidine-5-carboxamide (Example 1 (Compound D))

A 100 mL reactor was charged with acetonitrile (35 mL), 2-(5-((3-ethoxypyridin-2-yl)oxy)pyridin-3-yl)pyrimidine-5-carboxylic acid (5.0 g, 15 mmol) and (S)-tetrahydrofuran-3-amine hydrochloride (2.2 g, 18 mmol, 1.2 equiv). Diisopropylethylamine (18 mL, 103 mmol, 7.0 equiv) was charged while maintaining the temperature at 20° C. to 30° C. A solution of propane phosphonic acid anhydride (T3P) in acetonitrile (21 mL, 30 mmol, 2.0 equiv) was charged at a rate that maintained the temperature below 45° C. The reactor was heated to 40±5° C. for 1 hour then sampled for reaction completion. The reaction was cooled to 20° C. to 25° C. and tetrahydrofuran (25 mL) was added. A solution of sodium bicarbonate (0.5M, 40 mL) was charged and the mixture was stirred for 1 hour. The pH was checked and measured at 8.5. Ethyl acetate (40 mL) was added and the mixture stirred for 15 minutes. The mixture was settled and the phases split. The aqueous layer was transferred to a separatory funnel and back extracted with ethyl acetate (100 mL). The organic phases were combined and washed with water (40 mL). The organic layer was transferred to a 100 mL reactor in portions and concentrated under vacuum to a low volume. Methyl ethyl ketone (100 mL) was added and the mixture was concentrated to a final volume of approximately 60 mL. Vacuum was removed and the slurry was heated to reflux and held until the solids were washed down the reactor walls. The slurry was cooled to 15° C. over 2 hours and granulated overnight. The solids were isolated by filtration, washing the reactor and cake twice with methyl ethyl ketone (10 mL each). The solids were dried in a vacuum oven at 50° C. to yield 4.86 g (81%) of the desired product. The solid form from this procedure was characterized by PXRD analysis and assigned as Form 2 of Compound D.

Conversion of the Form 2 to the Form 1 of Compound D

To a 100 mL reactor was charged Form 2 of (S)-2-(5-((3-ethoxypyridin-2-yl)oxy)pyridin-3-yl)-N-(tetrahydrofuran-3- yl)pyrimidine-5-carboxamide (Example 1) (10.0 g, 24.6 mmol, 1.00 equiv.), Methyl ethyl ketone (8.8 mL/g, 88.0 mL) and water (1.2 mL/g, 12.0 mL). The reactor was heated to 50° C. over 30 minutes. A complete solution appeared at approximately 44° C. The reactor was cooled to 40° C. over 30 minutes then seed Form 1 of (S)-2-(5-((3-ethoxypyridin-2-yl)oxy)pyridin-3-yl)-N-(tetrahydrofuran-3-yl)pyrimidine-5-carboxamide (Example 1 of Compound D) (0.050 g, 0.123 mmol, 0.0050 equiv.) was charged. After seeding, the hazy slurry was stirred for 1 hour before cooling to 5° C. over 2 hours and then stirred at 5° C. for 12 hours. An in process control sample was pulled and characterized by PXRD analysis to confirm the solids were Form 1 of Compound D. The slurry was filtered, and the reactor and cake was washed with 0° C. methyl ethyl ketone (2.5 mL/g, 25 mL). The solids were dried in a vacuum oven at 50° C. to yield 8.15 g (81.5%) of the desired product. PXRD patterns of the desired product were consistent with Form 1 of Compound D.

Powder X-Ray Diffraction:

Powder X-ray diffraction analysis was conducted using a Bruker AXS D8 Advance diffractometer equipped with a Cu radiation source (Kα-average wavelength of 1.54056 Å), equipped with a twin primary utilizing a gobel mirror. Diffracted radiation was detected by a PSD-Lynx Eye detector. Both primary and secondary equipped with 2.5 soller slits. The X-ray tube voltage and amperage were set at 40 kV and 40 mA respectively. Data was collected in the Theta-Theta goniometer in a locked couple scan from 3.0 to 40.0 degrees 2-Theta with 1000 steps using a scan speed of 6 seconds per step. Samples were prepared by placement in a silicon low background sample holder (C79298A3244B261). Data were collected using Bruker DIFFRAC Plus software. Analysis performed by EVA diffract plus software.

The PXRD data file was not processed prior to peak searching. Using the peak search algorithm in the EVA software, peaks were selected with a threshold value of 5 and a width value of 0.2. The output of automated assignments was visually checked to ensure validity and adjustments manually made if necessary. Peaks with relative intensity of ≥3% were generally chosen. The peaks which were not resolved or were consistent with noise were also discarded. A typical error associated with the peak position from PXRD stated in USP is within +/−0.2° (USP-941).

TABLE 1

Key PXRD peaks to characterize crystalline material
Example 1 (Compound D)

| Form 1 of Example 1 | Form 2 of Example 1 |
|---|---|
| Angle 2Θ (°) | Angle 2Θ (°) |
| 5.3, 7.7, 15.4 | 6.5, 9.3, 13.6 |

FIG. 1 is a characteristic x-ray powder diffraction pattern showing crystalline form 1 of Example 1 (Compound D) (Vertical Axis: Intensity (CPS); Horizontal Axis: Two theta (degrees)).

Figure 2:
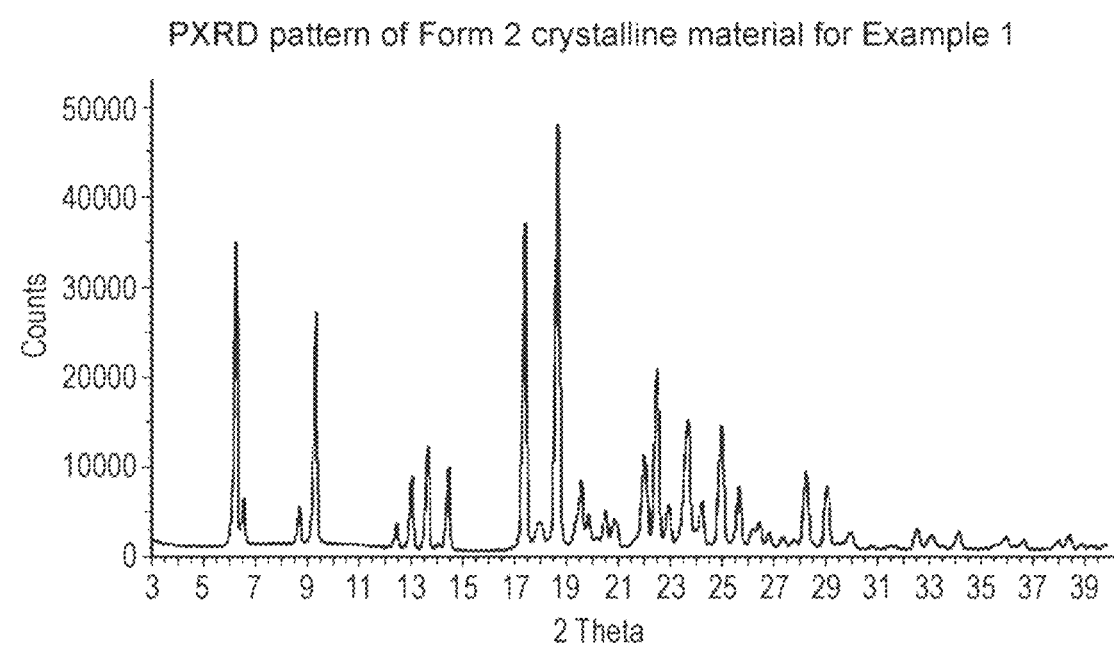
FIG. 2 is a characteristic x-ray powder diffraction pattern showing crystalline Form 2 of Example 1 of the DGAT2i Compound (Vertical Axis: Intensity (CPS); Horizontal Axis: Two theta (degrees)).

FIG. 2 is a characteristic x-ray powder diffraction pattern showing crystalline Form 2 of Example 1 (Compound D) (Vertical Axis: Intensity (CPS); Horizontal Axis: Two theta (degrees)).

Example 2: Preparation of 4-(4-(1-isopropyl-7-oxo-1,4,6,7-tetrahydrospiro[indazole-5,4'-piperidine]-1'-carbonyl)-6-methoxypyridin-2-yl)benzoic acid, Compound A (ACCi Compound)

In the preparation of Compound A, it is noted that some of the preparation methods described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, Protective Groups in Organic Synthesis, John Wiley & Sons, New York, 1991. Furthermore, this invention is not limited to specific synthetic methods provided herein that may vary.

Intermediate A1: 1-Isopropyl-4,6-dihydrospiro[indazole-5,4'-piperidin]-7(1H)-one, Hydrochloride Salt

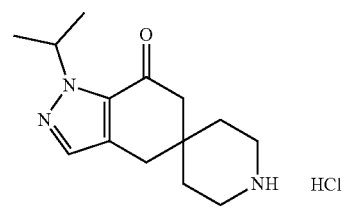 [SMILES: CC(C)n1ncc2c1C(=O)CC1(CCNCC1)C2 ; Cl]

Step 1. tert-Butyl 9-oxo-3-azaspiro[5.5]undec-7-ene-3-carboxylate

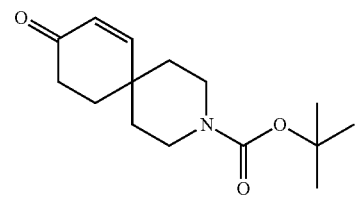 [SMILES: CC(C)(C)OC(=O)N1CCC2(C=CC(=O)CC2)CC1]

A dry reactor was charged with tert-butyl 4-formylpiperidine-1-carboxylate (108 Kg), cyclohexane (1080 L) and pyrrolidine (64.8 Kg) at 25-30° C. The mixture was stirred 5-10 min, and was then heated to reflux for 12-16 h, while collecting water using a Dean-Stark trap. The reaction mixture was then cooled to 50-60° C., at which temperature vacuum was applied to distill excess pyrrolidine and cyclohexane. The reaction mixture was then cooled to 25-30° C., and cyclohexane (648 L) was charged, followed by methyl vinyl ketone (49.63 Kg). The mixture was stirred for 12-16 h, then filtered and the filtrate was charged into a clean and dry reactor. The solution was cooled to 10-15° C., then a solution of acetic acid (54.75 Kg) in water (54 L) was slowly added, maintaining the temperature below 15° C. At the end of the addition, the mixture was warmed up to 25-30° C. and stirred for 12-16 h. The layers were separated and the aqueous was extracted with ethyl acetate (324 L). Combined organic layers were washed with a solution of sodium bicarbonate (32.34 Kg) in water (324 L), then dried over sodium sulfate. The solids were washed with ethyl acetate (54 L), and combined filtrates were concentrated under reduced pressure at below 40° C. n-Heptane (216 L) was charged into the reactor and distillation was pursued under reduced pressure and at below 40° C. until dryness. The mixture was cooled to 25-30° C. and n-heptane (216 L) was charged in the reactor. The mixture was stirred for 1-2 h after formation of solids. The solids were then filtered, washed with n-heptane (54 L) and dried at 40-50° C. for 10-12 h to generate the desired material (90.1 Kg, 67% yield).

Step 2. (E)-tert-Butyl 10-((dimethylamino)methylene)-9-oxo-3-azaspiro[5.5]undec-7-ene-3-carboxylate

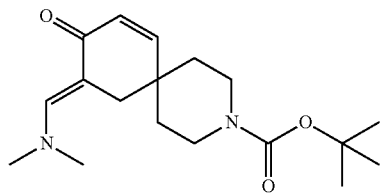 [SMILES: CN(C)/C=C1\CC2(C=CC1=O)CCN(C(=O)OC(C)(C)C)CC2]

A clean and dry reactor was charged with tert-butyl 9-oxo-3-azaspiro[5.5]undec-7-ene-3-carboxylate (50 Kg), N,N-dimethylformamide (500 L) and N,N-dimethylformamide dimethyl acetal (135 Kg) at 25-30° C. under nitrogen atmosphere. The reaction mixture was stirred 5-10 min then heated to 120-130° C. for 20 h. the mixture was then cooled to 50-60° C., and the solvent was distilled under high vacuum at below 60° C. Mix-xylenes (200 L) was charged at below 45° C. and the solvent was distilled under high vacuum at below 60° C. This operation was repeated with another lot of mix-xylenes (200 L). Toluene (200 L) was then charged into the reactor and the solvent was distilled under high vacuum at below 60° C. This operation was repeated with a second lot of toluene (200 L). Methyl tert-butyl ether (100 L) was then charged at below 30° C. and the solvent was distill under high vacuum at below 40° C. The mixture was cooled down to 15-20° C. and methyl tert-butyl ether (100 L) was charged at below 20° C. The mixture was stirred for 20-30 min and the solids were filtered, washed with methyl tert-butyl ether (50 L) and dried without vacuum at 50-55° C. for 10 h to provide the desired compound (52.1 Kg, 87% yield). $^1$H NMR (400 MHz, CDCl$_3$) δ ppm 7.48 (s, 1H), 6.57 (d, J=9.97 Hz, 1H), 5.99 (d, J=10.16 Hz, 1H), 3.32-3.51 (m, 4H), 3.06 (s, 6H), 2.72 (s, 2H), 1.57-1.66 (m, 2H), 1.41-1.53 (m, 11H).

Step 3. tert-Butyl 1-isopropyl-1,4-dihydrospiro[indazole-5,4'-piperidine]-1'-carboxylate

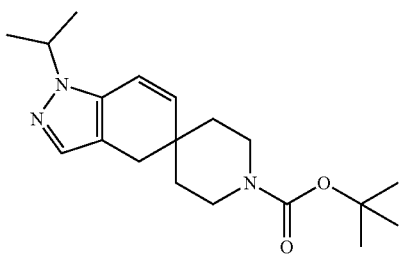 [SMILES: CC(C)n1ncc2c1C=CC1(CCN(C(=O)OC(C)(C)C)CC1)C2]

A clean and dry reactor was charged with (E)-tert-butyl 10-((dimethylamino)methylene)-9-oxo-3-azaspiro[5.5]undec-7-ene-3-carboxylate (80 Kg), toluene (704 L) and trimethylamine (16 L) at 25-30° C. The reaction mixture was warmed up to 70-80° C., and a solution of isopropyl hydrazine hydrochloride salt in methanol (1.25 equiv., 141 Kg total) was added over 4-5 h. The reaction mixture was then stirred for 8-10 h at 70-80° C., prior cooling to 15-25° C. A solution of citric acid (48 Kg) in water (480 L) was then slowly added, maintaining internal temperature below 25° C. Ethyl acetate (208 L) was added and the mixture was stirred for 10 min. Layers were separated and the organic layer was successively washed with a solution of citric acid (48 Kg) in water (480 L), then with only water (320 L). Combined aqueous layers were extracted with ethyl acetate (320 L). Combined organic layers were then dried over sodium sulfate (8 Kg) and the solvents were evaporated to dryness under reduce pressure and at below 40° C. Dichloromethane (240 L) was charged into the reactor and the mixture was stirred at 25-30° C. until clear. Activated carbon (1.84 Kg), magnesium silicate (1.84 Kg) and silica gel (32 Kg, 100-200 mesh) were successively charged at 25-30° C. and the heterogeneous mixture was stirred for 1 h. The slurry was then filter on a Hyflow bed, prepared by mixing Hyflow supercell (8 Kg) and dichloromethane (40 L). The cake was washed with dichloromethane (three times 120 L). The combined filtrates were charged back in the reactor and the solvent was evaporated under reduced pressure at below 40° C. n-Heptane (160 L) was then charged and distilled under reduced pressure at below 40° C. n-Heptane (200 L) was charged in the reactor and the mixture was cooled down to 0-5° C. After stirring for 12-15 h, the solids were filtered at 0-5° C., washed with chilled (0-5° C.) n-heptane (160 L) and dried under vacuum at 40-50° C. to provide the title compound (82.4 Kg, 75%). $^1$H NMR (400 MHz, CDCl$_3$) δ ppm 7.25 (s, 1H), 6.42 (dd, J=10.05, 0.49 Hz, 1H) 5.84 (d, J=9.95 Hz, 1H), 4.42-4.52 (m, 1H), 3.36-3.53 (m, 4H), 2.62 (s, 2H) 1.56-1.68 (m, 2H) 1.45-1.55 (m, 17H).

Step 4. 1-Isopropyl-4,6-dihydrospiro[indazole-5,4'-piperidin]-7(1H)-one, Hydrochloride Salt

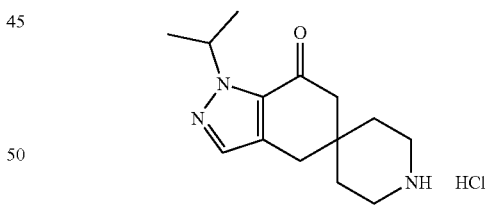

A clean and dry reactor was charged with tert-butyl 1-isopropyl-1,4-dihydrospiro[indazole-5,4'-piperidine]-1'-carboxylate (60 Kg) and methanol (600 L) at 25-30° C. N-Bromosuccinimide (32.4 Kg) was added in 5 portions over 30-40 min at 25-30° C. and stirring was continued for 30-60 min. A solution of sodium thiosulfate pentahydrate (5.4 Kg) in water (102 L) was slowly added, maintaining internal temperature below 30° C. The mixture was stirred for 20-30 min then the solvent was evaporated under reduced pressure at below 45° C. The residue was cooled down to 25-30° C. and 2-methyltetrahydrofuan (420 L) was charged in the reactor, along with water (90 L). The mixture was stirred for 15-20 min, then the layers were separated, the aqueous layer was further extracted with 2-methyltetrahydrofuran (120 L). Combined organic extracts were treated for 15-20 min at 25-30° C. with a solution of sodium hydroxide (4.8 Kg) in water (120 L). Layers were separated and the organic layer was washed with water (120 L), followed by a solution of sodium chloride (12 Kg) in water (120 L) and then dried over sodium sulfate (6 Kg). After filtration, the cake was washed with 2-methyltetrahydrofuran (30 L) and combined filtrate were charged back into the reactor. The solvent was completely distilled at below 45° C. under reduced pressure and the residue was solubilized in tetrahydrofuran (201 L). In another clean and dry reactor was charged potassium tert-butoxide (60.6 Kg) and tetrahydrofuran (360 L) at 25-30° C. To that mixture was slowly added the solution of the residue in tetrahydrofuran maintaining a temperature below 30° C. The reaction mixture was then warmed up to 60-65° C. and kept at this temperature for 1-2 h. Upon completion, the mixture was cooled to 0-10° C., and slowly quenched with a solution of hydrochloric acid (1 N, 196 L), maintaining internal temperature below 10° C. The reaction mixture was allowed to warm up to 25-30° C., and ethyl acetate (798 L) was charged. After stirring for 15-20 min, the layers were separated, and the aqueous layer was further extracted with ethyl acetate (160 L). Combined organic layers were washed with water (160 L), dried over sodium sulfate (8 Kg), filtered, and the cake was washed with ethyl acetate (300 L). The solvents were entirely distilled under reduced pressure at below 45° C., and ethyl acetate (540 L) was charged into the reactor at 25-30° C., followed by methanol (156 L). The mixture was cooled to 0-5° C., at which point acetyl chloride (79.8 Kg) was slowly added, maintaining the temperature in the specified range. The mixture was then allowed to warm up to 20-25° C. and was kept at this temperature for 4-5 h with stirring. The resulting slurry was filtered and the solids were washed with ethyl acetate (120 L), then dried at 40-45° C. for 8-10 h to furnish the desired crude product (33.5 Kg, 65%).

A final purification step was performed by solubilizing this crude solid (56.8 Kg) in methanol (454.4 L) in a clean a dried reactor at 25-30° C. The solution was stirred for 30-45 min, then passed through a 0.2 micron cartridge filter into a clean and dry reactor at 25-30° C. Methanol was distilled under reduced pressure at below 50° C. until ~1 vol solvent remains. The reaction mixture was cooled to 25-30° C. and fresh acetonitrile (113.6 L) was charged through a 0.2 micron cartridge filter. The solvents were distilled under reduced pressure at below 50° C. until ~1 vol solvent remains. The reaction mixture was cooled to 25-30° C. and fresh acetonitrile (190 L) was charged into the reactor through a 0.2 micron cartridge filter. The mixture was warmed up to 65-70° C. and stirred for 45 min, then cooled down to 25-30° C. and stirred for 1 h. the resulting slurry was filtered, and the cake was washed with chilled (15° C.) acetonitrile (56.8 L). The solids were dried under reduced pressure at 40-50° C. for 8 h to afford Intermediate A1 (36.4 Kg, 64%). $^1$H NMR (400 MHz, CD$_3$OD) δ ppm 7.43 (s, 1H), 5.32-5.42 (m, 1H), 3.15-3.25 (m, 4H), 2.89 (s, 2H), 2.64 (s, 2H), 1.69-1.90 (m, 4H), 1.37-1.45 (m, 6H); ESI [M+H]$^+$=248.

Intermediate A2: 2-(4-(tert-Butoxycarbonyl)phenyl)-6-methoxyisonicotinic Acid

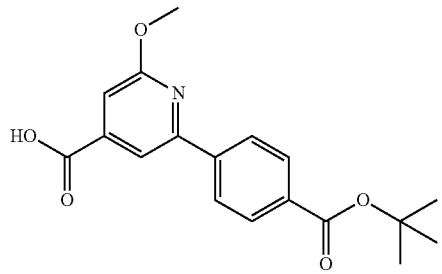 [SMILES: COc1cc(C(=O)O)cc(-c2ccc(C(=O)OC(C)(C)C)cc2)n1]

A clean and dried reactor was charged with 2,6-dichloroisonicotinic acid (30 Kg) and methanol (120 L) at 20-25° C. The slurry was stirred for 5 min then heated up to 65° C. (reflux). A solution of sodium methoxide in methanol (30%, 87.2 Kg) was then slowly charged over at least 4 h via addition funnel. The funnel was rinsed with methanol (15 L), and stirring was pursued at 65° C. for at least 15 h. the mixture was then cooled down to 45° C. and distilled under reduced pressure until a residual volume of ~90 L. A solution of potassium bicarbonate (28.2 Kg) and potassium carbonate (21.6 Kg) in water (180 L) was then charged into the reactor at 40-45° C. The reactor containing the aqueous solution was rinsed with water (21 L) and the wash was charged into the reaction mixture. The mixture was distilled under reduced pressure at below 80° C. until a residual volume of ~240 L, then cooled down to 20-25° C.

Another clean and dry reactor was charged with tert-butyl 4-(4,4,5,5-tetramethyl-1,3,2-dioxoborolan-2-yl) benzoate (52.3 Kg) and dioxane (340 Kg), and stirred at 2-25° C. until complete dissolution. The content of the former reactor was then heated at 40° C. to ensure complete solubility and transferred into this new reactor. The reaction mixture was cooled down to 20-25° C., and a deoxygenation step was performed via vacuum/nitrogen cycles. The mixture was further cooled down to 0-10° C. and palladium acetate (0.65 Kg) was charged into the reactor followed by triphenylphosphine (2.46 Kg) under nitrogen flow. The mixture was warmed up to 20-25° C. and another deoxygenation step was performed via vacuum/nitrogen cycles. The mixture was then heated to 80° C. and maintained at this temperature for at least 18 h. the mixture was cooled down to 20-25° C., then methyl tert-butyl ether (133.2 Kg) and water (30 L) were successively charged into the reactor. The layers were separated, and the aqueous was diluted with water (110 L), then extracted with methyl tert-butyl ether (110 L). Combined organic extracts were washed with a solution of citric acid (52 Kg) in water (84 L), and the layers were separated. The aqueous layer was further extracted with methyl tert-butyl ether (88.8 Kg) and organic layers were combined, then washed three times with a third of a solution of sodium chloride (43 Kg) in water (80 L). After final layer separation, the organic layer was filtered through pall filter containing a charcoal cartridge, and the cake was washed with methyl tert-butyl ether (11.2 Kg). The filtrate was distilled under reduced pressure at below 50° C. down to ~90 L, and was then successively co-distilled with heptane (120 L), at below 50° C. and down to ~120 L. the mixture was then cooled down to 20-25° C. over 1 h, then stirred at this temperature for another 1 h. The slurry was filtered and the cake was washed three times with heptane (3×18 L), then three times with acetonitrile (3×18 L). The resulting wet solid was dried under vacuum and nitrogen flow at below 45° C. for at least 15 h to afford Intermediate A2 (44.6 Kg, 87% yield). $^1$H NMR (400 MHz, CDCl$_3$) b ppm 8.13 (s, 2H), 8.09 (s, 2H), 7.97 (d, J=1.17 Hz, 1H), 7.34 (d, J=0.98 Hz, 1H), 4.08 (s, 3H), 1.61 (s, 9H); ESI [M+H]$^+$=330.

Intermediate A3: tert-Butyl 4-(4-(1-isopropyl-7-oxo-1,4,6,7-tetrahydrospiro[indazole-5,4'-piperidine]-1'-carbonyl)-6-methoxypyridin-2-yl)benzoate

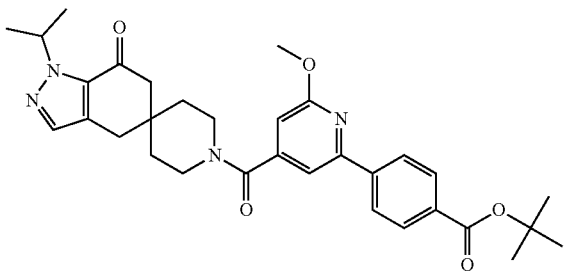 [SMILES: COc1cc(C(=O)N2CCC3(CC2)CC(=O)c2c(cnn2C(C)C)C3)cc(-c2ccc(C(=O)OC(C)(C)C)cc2)n1]

A round bottomed flask was charged with 2-(4-(tert-butoxycarbonyl)phenyl)-6-methoxyisonicotinic acid (Intermediate A2, 15.2 g, 46.2 mmol) and ethyl acetate (140 mL). 1,1'-Carbonyldiimidazole (8.98 g, 55.4 mmol) was added in one portion and stirred for 1 h at rt. 1-isopropyl-4,6-dihydrospiro[indazole-5,4'-piperidin]-7(1H)-one hydrochloride (Intermediate A1, 14.8 g, 52.2 mmol) was added followed by N,N-diisopropylethylamine (9.1 mL, 52.2 mL) and the reaction stirred for 18 h at rt. Aqueous 2 M HCl (40 mL) was added, followed by 1 M potassium hydrogensulfate (40 mL) and 50 mL of heptane. The obtained mixture was stirred for 1 h at rt. The mixture was transferred to separation funnel. The organic phase was separated, washed successively with water (20 mL), saturated sodium bicarbonate (30 mL), water (20 mL), brine (20 mL), dried over 20 g of magnesium sulfate and 10 g of silica gel, filtered, and concentrated in vacuo. Solid began to form towards the end of concentration. The residue was stirred in 40 mL of ethyl acetate at 80° C. and heptane (120 mL) was added slowly dropwise. The mixture was stirred at 80° C. for 1 h, then slowly cooled to room temperature with stirring over 1 h and stirred for 18 h at rt. The solid was collected via filtration, washed with water and ethyl acetate-heptane (1:3), and dried under vacuum at 50° C. for 18 h to obtain Intermediate A3 (19.64 g, 76% yield).

Alternative Preparation of Intermediate A3

A clean and dry reactor was charged with acetonitrile (219 Kg) and 2-(4-(tert-butoxycarbonyl)phenyl)-6-methoxyisonicotinic acid (Intermediate A2, 34.8 Kg) at 20-25° C. The mixture was stirred for 5 min, then 1,1-carbodiimidazole (18.9 Kg) was charged in three successive portions. The slurry was further stirred at 20-25° C. for at least 1 h, then 1-isopropyl-4,6-dihydrospiro[indazole-5,4'-piperidin]-7(1H)-one hydrochloride salt (Intermediate A1, 33.0 Kg) was charged into the reactor, followed by N,N-diisopropylethylamine (20.5 Kg) via pump. The reagent pump as well as the walls of the reactor were washed with acetonitrile (13.7 Kg), and stirring was pursued at 20-25° C. for at least 2 h. Upon completion, the mixture was seeded with tert-butyl 4-(4-(1-isopropyl-7-oxo-1,4,6,7-tetrahydrospiro[indazole-5,4'-piperidine]-1'-carbonyl)-6-methoxypyridin-2-yl)benzoate (Intermediate A3, 209 g) and stirred for at least 30 min. After confirmation of crystallization start, a solution of citric acid monohydrate (58.5 Kg) in water (257 L) was charged over 1 h. The resulting slurry was further stirred at 20-25° C. for at least 2 h, then filtered and the cake was washed with a mixture of acetonitrile (68.4 Kg) and water (87 L). This wash was used to rinse the reactor as well. The solids were dried under reduced pressure at below 55° C., affording Intermediate A3 (43.44 Kg, 73% yield).

Compound A (as the Free Acid): 4-(4-(1-isopropyl-7-oxo-1,4,6,7-tetrahydrospiro[indazole-5,4'-piperidine]-1'-carbonyl)-6-methoxypyridin-2-yl)benzoic Acid

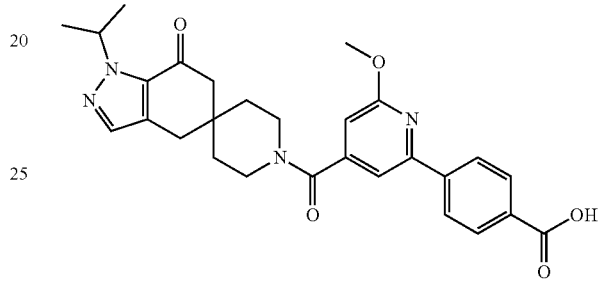

A round bottomed flask was charged with tert-butyl 4-(4-(1-isopropyl-7-oxo-1,4,6,7-tetrahydrospiro[indazole-5,4'-piperidine]-1'-carbonyl)-6-methoxypyridin-2-yl)benzoate (3.7 g, 6.6 mmol) and toluene (25 mL). 85% Phosphoric acid (3.0 mL) was added dropwise with stirring and the reaction was heated to 60° C. for 4 hours. A colorless thick gum formed. The reaction was cooled to rt and water was added. White solids were observed. The toluene organic layer was discarded, reserving the aqueous layer and solids. Ethyl acetate was added (60 mL) and 4N NaOH solution was added to adjust pH to ~7. The layers were separated and the aqueous was extracted with ethyl acetate (50 mL). The combined ethyl acetate organic layers were dried over sodium sulfate, filtered, and concentrated in vacuo to provide white solids. These were dissolved in ethyl acetate (80 mL) at 50° C. and heptane (90 mL) was added slowly. The heat was removed and the mixture was cooled to rt and stirred for 16 h. The resultant solids were collected via filtration, rinsed with the mother liquor, and dried to provide the title compound (Compound A free form, 2.15 g, 65% yield) as a white solid.

Alternative Preparation of Compound A (as the Free Acid)

A clean a dry reactor was charged with acetonitrile (130.4 Kg) and tert-butyl 4-(4-(1-isopropyl-7-oxo-1,4,6,7-tetrahydrospiro[indazole-5,4'-piperidine]-1'-carbonyl)-6-methoxypyridin-2-yl)benzoate (Intermediate A3, 20.72 Kg) at 20-25° C. The mixture was stirred for 5 min, then p-toluenesulfonic acid (8.5 Kg) was charged under a gentle nitrogen sweep. The reaction mixture was warmed up to 70° C. and maintained at this temperature for at least 6.5 h. Upon completion, the mixture was cooled down to 40° C., seeded with Compound A (104 g) and water (83 L) was slowly charged over at least 1 h. the mixture was further stirred at 40° C. for a minimum of 4 h, then cooled down to 20-25° C. over 2 h.

Further stirring for at least 2 h was followed by filtration, and the cake was rinsed with a solution of acetonitrile (33 Kg) and water (41 L). This wash was used to rinse the reactor as well. The resulting solids were dried under reduced pressure at below 55° C. to afford Compound A (16.5 Kg, 89% yield).

Preparation of Form 1 of Compound
A—Anhydrous Mono-Tris of Compound A

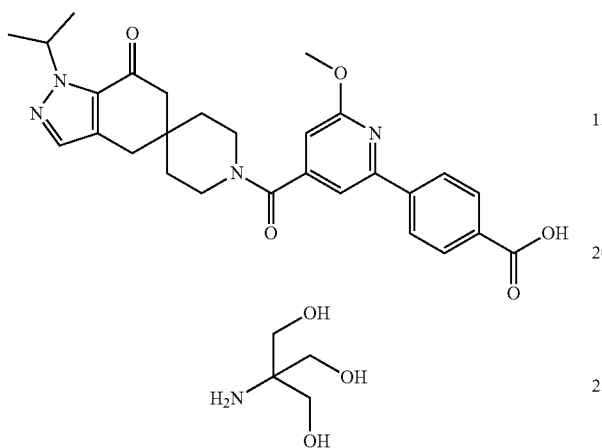

A vial was charged with 4-(4-(1-isopropyl-7-oxo-1,4,6,7-tetrahydrospiro[indazole-5,4'-piperidine]-1'-carbonyl)-6-methoxypyridin-2-yl)benzoic acid (151 mg, 0.300 mmol) and 3 mL of ethanol. The mixture was heated to 80° C. for 5 minutes to dissolve the solid and then cooled to rt. Tris(hydroxymethyl)aminomethane (39 mg, 0.32 mmol) was added, and the mixture was stirred overnight at rt. Heptane (2.25 mL) was added dropwise to produce a slurry that was heated to 50° C. to produce a clear solution. The mixture was cooled to rt overnight with stirring. White solids were observed, and the mixture was stirred for an additional 3 days. The material was filtered and dried in a vacuum oven at 50° C. overnight to produce Form 1 (151 mg, 0.242 mmol, 81% yield).

Alternative Preparation of Form 1 of Compound A: Anhydrous Mono-Tris of Compound A To a clean and dry reactor was charged ethanol (83 L), followed by the addition of Compound A (9.43 Kg) and tris (2.55 kg) while the mixture was maintained at a temperature of 20-25° C. The tank walls were rinsed with ethanol (2 L), and the resulting mixture was heated at 65-70° C., maintained at this temperature for at least 30 min until all solids dissolved, then cooled down to 45-50° C. A warm filtration through a 10 μm in-line polypropylene filter was performed, and the reactor as well as the filter were washed with ethanol (9 L). n-Heptane (24 L) was charged into the warm solution through the same in-line filter, and the mixture was seeded with 4-(4-(1-isopropyl-7-oxo-1,4,6,7-tetrahydrospiro[indazole-5,4'-piperidine]-1'-carbonyl)-6-methoxypyridin-2-yl) benzoic acid anhydrous tris salt (100 g) in ethanol (0.5 L) at 45-50° C. The temperature was held for at least 2 h before cooling down to 20-25° C. over at least 2 h. Stirring was pursued for at least 5 days. The slurry was then filtered, and the cake was washed with a mixture of ethanol (13 L) and n-heptane (6 L). The solids were dried under reduced pressure at below 45° C. for at least 12 h, affording example 1 (11.7 Kg, 77%).

Preparation of Form 2 of Compound A—Trihydrate of the Mono-Tris Salt of Compound A

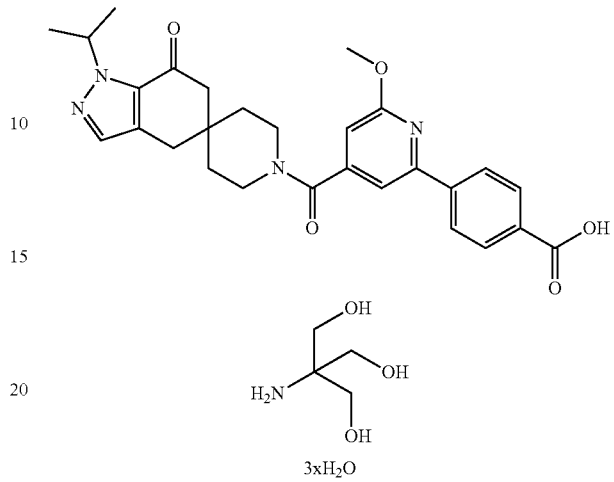

Form 2 of Compound A was obtained from conversion from Form 1 of Compound A. Into a 50 mL EasyMax reactor was added Form 1 (1.7214 g, 2.760 mmol), Isopropanol (16.50 mL, 215.8 mmol), and Water (688 μL, 38.190 mmol). The mixture was stirred (300 rpm) for about 72 hr with a reactor jacket temperature of 25° C. The reaction mixture was then warmed to 40° C. over 15 min and held at 40° C. for about 24 hours, cooling once to 20° C. to remove a sample for testing. A mixture of forms was seen by PXRD; therefore, additional water Water (688 μL, 38.190 mmol) was added. The stir rate was increased to 400 rpm and the slurry was allowed to stir for 6 hours and was then cooled to 15° C. The solids were isolated on a 60 mL/40 M filter and washed with 96/4 isopropanol/water. The resulting material was consistent with Form 2 of Compound A by PXRD.

Alternative Preparation of Form 2 of Compound A—Trihydrate of the Mono-Tris Salt of Compound A A clean and dry reactor was charged with isopropanol (60.4 Kg), and Compound A (16.68 Kg) and tris (4.42 kg) were added while the mixture was maintained at a temperature of 20-25° C. The mixture was stirred for 5 min, then water (6.7 Kg) was charged and the slurry was warmed up to 55° C. The now clear solution was filtered into a pre-warmed clean and dry reactor (50-55° C.) through an in-line 10 μm polypropylene filter. The solution was then seeded with the mono-tris salt of Compound A as a trihydrate (167 g). After verification that the seed persisted, the mixture was cooled down to 15° C. over at least 2 h, then maintained at 15° C. for a minimum of 16 h. The slurry was filtered and the cake washed with chilled isopropanol (13.1 Kg). The solids were then dried under reduced pressure at below 25° C. to afford only Form 2 of Compound A (22.1 Kg, 98% yield).

Figure 3:
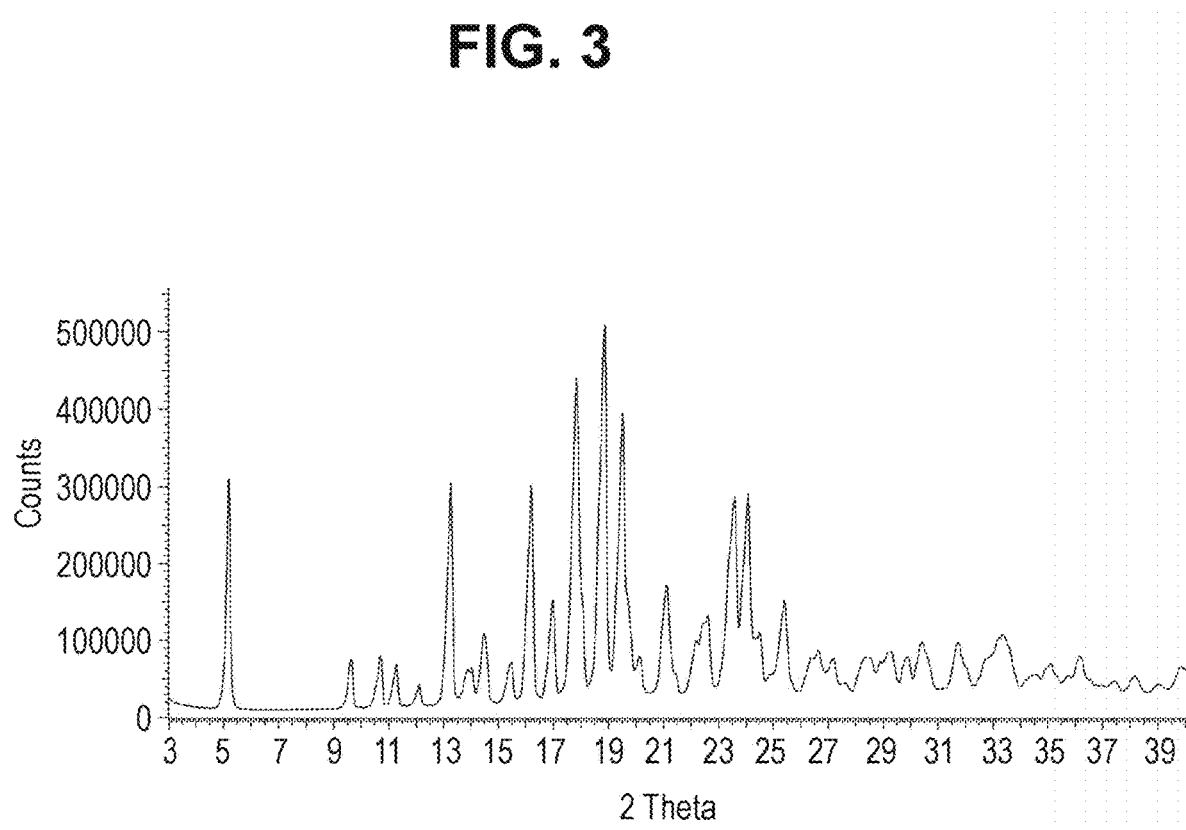
FIG. 3 shows an illustrative PXRD pattern of Form 1 of Compound A carried out on a Bruker AXS D4 Endeavor diffractometer equipped with a Cu radiation source.

Form 1 of Compound A is anhydrous and is thermodynamically stable below a water activity of about 0.2 (20% RH) at ambient temperature. Form 1 of Compound A has a PXRD pattern substantially the same as that shown in FIG. 3 of Compound A. Characteristic PXRD peaks of Form 1 of Compound A, expressed as 2Θ±0.2° 2Θ are at 9.6, 10.7, and 11.3. Peak locations and intensities for the PXRD pattern in FIG. 3 are provided in Table 2.

TABLE 2

PXRD Peaks and Relative Intensities of Form 1 of Compound A

| Degrees 2Θ ± 0.2° 2Θ | Relative Intensity (%) |
|---|---|
| 5.2 | 62 |
| 9.6 | 13 |
| 10.7 | 14 |
| 11.3 | 11 |
| 12.1 | 6 |
| 13.3 | 60 |
| 13.9 | 9 |
| 14.0 | 10 |
| 15.5 | 11 |
| 16.2 | 58 |
| 17.0 | 27 |
| 17.8 | 86 |
| 18.9 | 100 |
| 19.5 | 77 |
| 20.1 | 11 |
| 21.1 | 29 |
| 22.2 | 15 |
| 22.4 | 19 |
| 22.6 | 21 |
| 23.6 | 53 |
| 24.1 | 54 |
| 24.5 | 16 |
| 25.4 | 25 |
| 26.4 | 9 |
| 26.6 | 11 |
| 27.2 | 9 |
| 28.3 | 9 |
| 29.3 | 10 |
| 29.9 | 9 |
| 30.4 | 13 |
| 31.7 | 13 |
| 33.4 | 15 |

Figure 4:
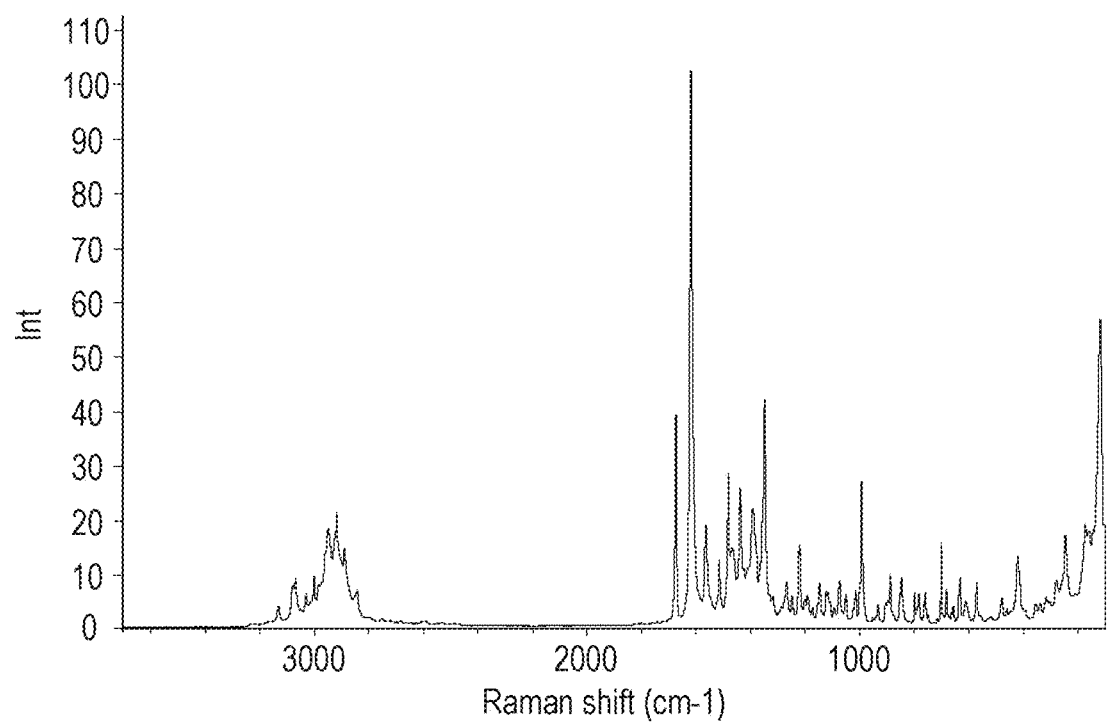
FIG. 4 shows an illustrative Raman spectra of Form 1 of Compound A collected using a Nicolet NXR FT-Raman accessory attached to the FT-IR bench.

Form 1 of Compound A has a Raman spectrum substantially the same as that shown in FIG. 4. Form 1 of Compound A has characteristic Raman peak shifts, expressed as cm$^{-1}$, at 568, 698, 989, 1218, 1511, 1561, and 1615, ±2 cm$^{-1}$. Peak positions (±2 cm$^{-1}$) and normalized intensity (W=weak, M=medium, S=strong) of Form 1 of Compound A in FIG. 4 are listed in Table 3.

TABLE 3

Raman Peaks and Normalized Intensity of Form 1 of Compound A

| Raman Peak Position (cm$^{-1}$) | Normalized Intensity |
|---|---|
| 115 | M |
| 156 | W |
| 170 | W |
| 241 | W |
| 274 | W |
| 311 | W |
| 334 | W |
| 350 | W |
| 417 | W |
| 456 | W |
| 476 | W |
| 568 | W |
| 608 | W |
| 628 | W |
| 653 | W |
| 678 | W |
| 698 | W |
| 755 | W |
| 779 | W |
| 794 | W |
| 842 | W |
| 885 | W |
| 929 | W |
| 989 | W |
| 1011 | W |
| 1047 | W |
| 1071 | W |
| 1090 | W |
| 1119 | W |
| 1143 | W |
| 1169 | W |
| 1187 | W |
| 1196 | W |
| 1218 | W |
| 1244 | W |
| 1265 | W |
| 1315 | W |
| 1345 | M |
| 1363 | W |
| 1388 | W |
| 1435 | W |
| 1466 | W |
| 1478 | W |
| 1511 | W |
| 1561 | W |
| 1615 | S |
| 1671 | M |
| 2840 | W |
| 2885 | W |
| 2914 | W |
| 2945 | W |
| 2998 | W |
| 3027 | W |
| 3066 | W |
| 3129 | W |

Figure 5:
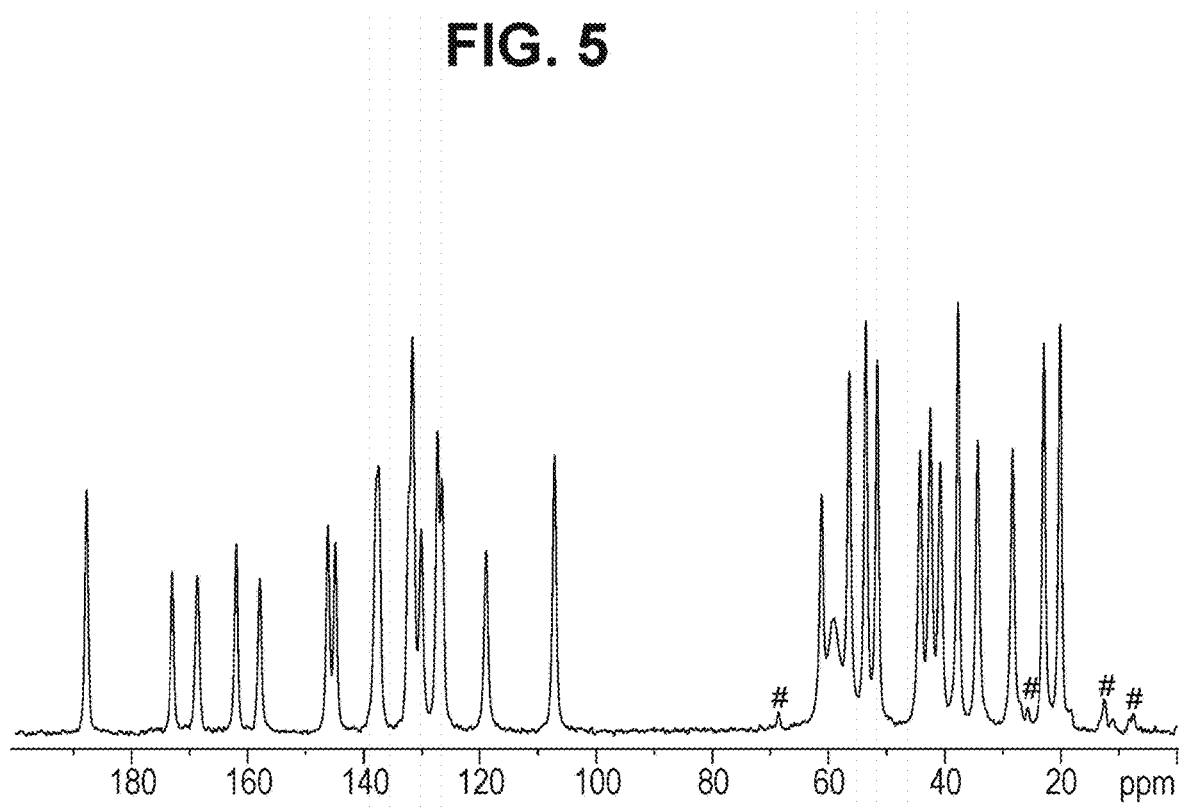
FIG. 5 shows an illustrative $^{13}$C ssNMR pattern of Form 1 of Compound A conducted on a Bruker-BioSpin CPMAS probe positioned into a Bruker-BioSpin Avance III 500 MHz ($^{1}$H frequency) NMR spectrometer.

Form 1 of Compound A has a $^{13}$C ssNMR spectrum substantially the same as that shown in FIG. 5. Form 1 of Compound A has characteristic $^{13}$C ssNMR chemical shifts, expressed as ppm, at 22.9, 146.2, 157.9, 161.9, and 172.9, ±0.2 ppm. $^{13}$C chemical shifts (±0.2 ppm) of Form 1 of Compound A as shown in FIG. 5 are listed in Table 4.

TABLE 4

$^{13}$C chemical shifts and Intensity of Form 1 of Compound A

| $^{13}$C chemical shifts (ppm) | Intensity |
|---|---|
| 20.1 | 95 |
| 22.9 | 90 |
| 28.4 | 66 |
| 34.3 | 68 |
| 37.7 | 100 |
| 40.8 | 63 |
| 42.5 | 76 |
| 44.3 | 66 |
| 51.6 | 87 |
| 53.6 | 96 |
| 56.4 | 84 |
| 59.1 | 27 |
| 61.2 | 55 |
| 107.1 | 65 |
| 118.9 | 42 |
| 126.6 | 59 |
| 127.3 | 70 |
| 130.2 | 47 |
| 131.7 | 92 |
| 132.3 | 56 |
| 137.5 | 62 |
| 137.9 | 59 |

TABLE 4-continued 13C chemical shifts and Intensity of Form 1 of Compound A

| 13C chemical shifts (ppm) | Intensity |
|---|---|
| 144.9 | 44 |
| 146.2 | 48 |
| 157.9 | 36 |
| 161.9 | 44 |
| 168.6 | 36 |
| 172.9 | 38 |
| 187.7 | 56 |

Figure 6:
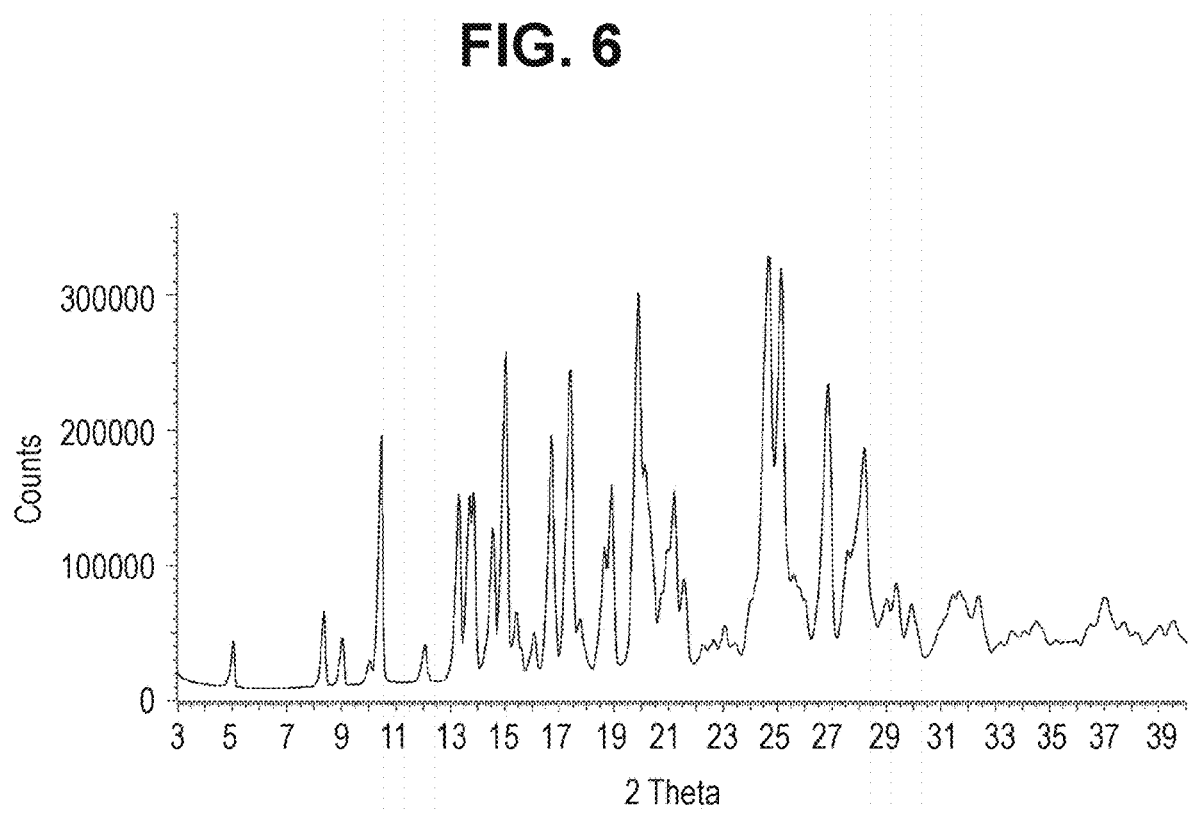
FIG. 6 shows an illustrative PXRD pattern of Form 2 of Compound A carried out on a Bruker AXS D4 Endeavor diffractometer equipped with a Cu radiation source.

Form 2 of Compound A is a trihydrate and is thermodynamically stable above a water activity of about 0.2 at ambient temperature and 20% RH. Form 2 of Compound A has a PXRD pattern substantially the same as that shown in FIG. 6. Characteristic PXRD peaks of Form 2 of Compound A, expressed as 2Θ±0.2° 2Θ are at 8.4, 9.0, 10.5, 15.0, and 24.7. Peak locations and intensities for the PXRD pattern in FIG. 6 are provided in Table 5.

TABLE 5

PXRD Peaks and Relative Intensities of Form 2 of Compound A

| Degrees 2Θ ± 0.2° 2Θ | Relative Intensity (%) |
|---|---|
| 5.0 | 11 |
| 8.4 | 18 |
| 9.0 | 12 |
| 10.0 | 6 |
| 10.5 | 62 |
| 12.1 | 9 |
| 13.3 | 46 |
| 13.7 | 45 |
| 13.9 | 46 |
| 14.6 | 37 |
| 15.0 | 80 |
| 15.4 | 15 |
| 16.1 | 10 |
| 16.7 | 59 |
| 17.4 | 74 |
| 17.8 | 13 |
| 18.6 | 30 |
| 18.9 | 45 |
| 19.9 | 93 |
| 20.1 | 50 |
| 21.2 | 46 |
| 21.5 | 21 |
| 24.7 | 100 |
| 25.2 | 97 |
| 26.9 | 71 |
| 28.2 | 52 |
| 29.0 | 15 |
| 29.4 | 18 |
| 29.9 | 13 |
| 31.4 | 15 |
| 31.7 | 16 |
| 32.4 | 14 |
| 33.6 | 5 |
| 34.5 | 7 |
| 37.0 | 12 |

Figure 7:
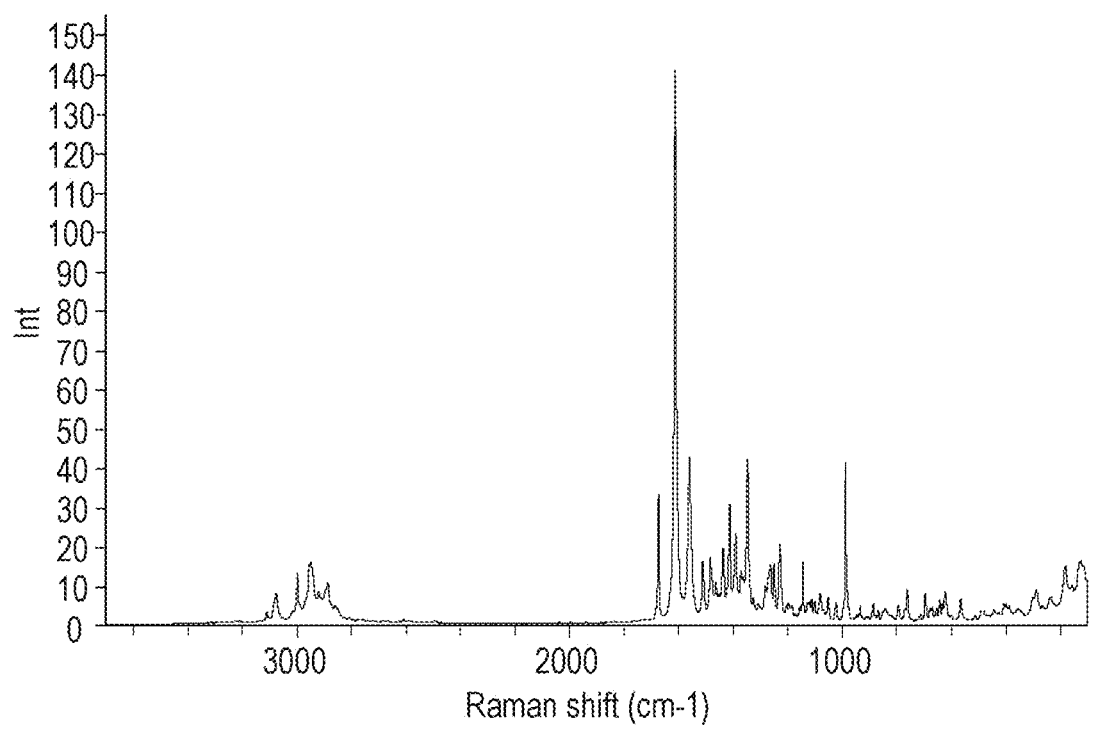
FIG. 7 shows an illustrative Raman spectra of Form 2 of Compound A collected using a Nicolet NXR FT-Raman accessory attached to the FT-IR bench.

Form 2 of Compound A has a Raman spectrum substantially the same as that shown in FIG. 7. Form 2 of Compound A has characteristic Raman peak shift, expressed as $cm^{-1}$, at 562, 692, 984, 1225, 1507, 1557, and 1610±2 $cm^{-1}$. Peak positions (±2 $cm^{-1}$) and normalized intensity (W=weak, M=medium, S=strong) of Form 2 of Compound A in FIG. 7 are listed in Table 6.

TABLE 6

Raman Peaks and Normalized Intensity of Form 2 of Compound A

| Raman Peak Position ($cm^{-1}$) | Normalized Intensity |
|---|---|
| 123 | W |
| 179 | W |
| 232 | W |
| 284 | W |
| 405 | W |
| 441 | W |
| 481 | W |
| 562 | W |
| 620 | W |
| 628 | W |
| 639 | W |
| 650 | W |
| 667 | W |
| 692 | W |
| 710 | W |
| 758 | W |
| 790 | W |
| 839 | W |
| 864 | W |
| 884 | W |
| 931 | W |
| 984 | W |
| 1019 | W |
| 1048 | W |
| 1077 | W |
| 1097 | W |
| 1109 | W |
| 1118 | W |
| 1140 | W |
| 1194 | W |
| 1225 | W |
| 1246 | W |
| 1261 | W |
| 1277 | W |
| 1305 | W |
| 1321 | W |
| 1344 | W |
| 1369 | W |
| 1387 | W |
| 1410 | W |
| 1433 | W |
| 1460 | W |
| 1480 | W |
| 1507 | W |
| 1557 | M |
| 1610 | S |
| 1670 | W |
| 2884 | W |
| 2916 | W |
| 2946 | W |
| 2995 | W |
| 3073 | W |
| 3108 | W |

Figure 8:
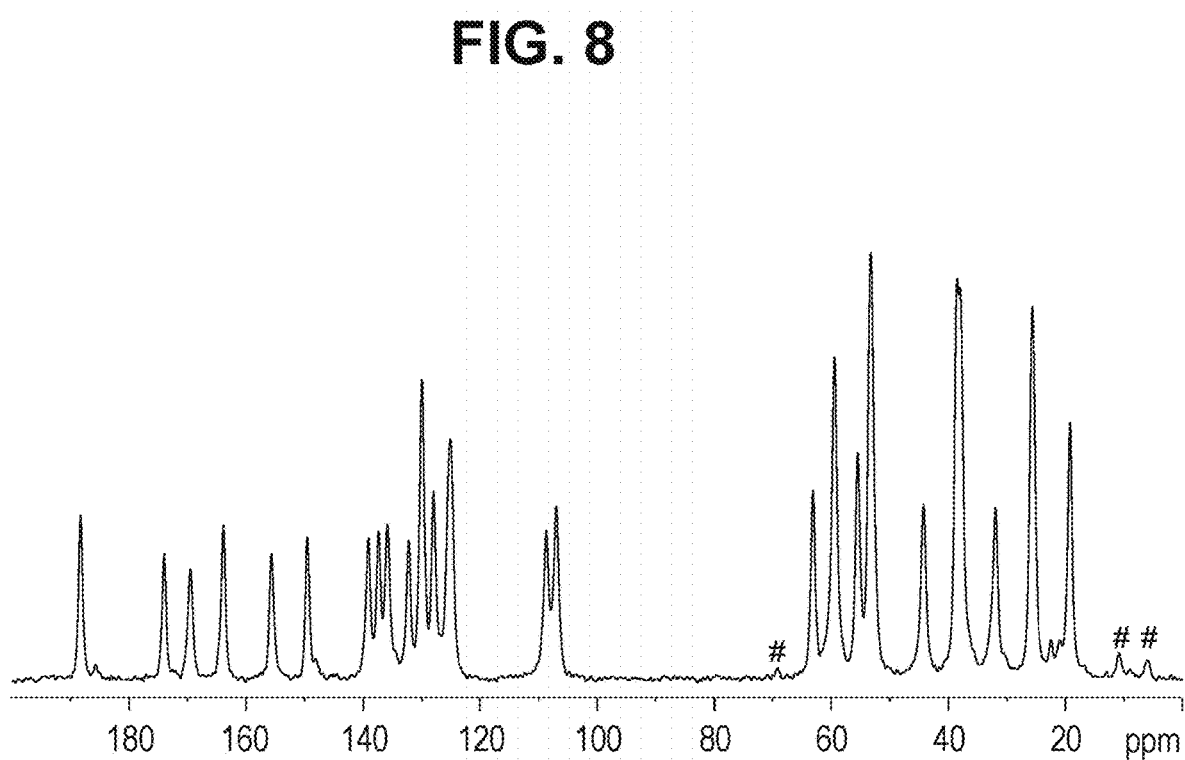
FIG. 8 shows an illustrative $^{13}$C ssNMR pattern of Form 2 of Compound A conducted on a Bruker-BioSpin CPMAS probe positioned into a Bruker-BioSpin Avance III 500 MHz ($^{1}$H frequency) NMR spectrometer.

Form 2 of Compound A has a 13C ssNMR spectrum substantially the same as that shown in FIG. 8. Form 2 of Compound A has characteristic 13C ssNMR chemical shifts, expressed as ppm, at 19.2, 149.5, 155.6, 163.8, and 188.3, ±0.2 ppm. 13C chemical shifts (±0.2 ppm) of Form 2 of Compound A as shown in FIG. 8 are listed in Table 7.

TABLE 7

13C chemical shifts and Intensity of Form 2 of Compound A

| 13C chemical shifts (ppm) | Intensity |
|---|---|
| 19.2 | 60 |
| 25.7 | 87 |
| 32.0 | 40 |
| 38.0 | 92 |

TABLE 7-continued

13C chemical shifts and Intensity of Form 2 of Compound A

| 13C chemical shifts (ppm) | Intensity |
|---|---|
| 38.5 | 94 |
| 44.2 | 41 |
| 53.2 | 100 |
| 55.5 | 53 |
| 59.4 | 76 |
| 63.1 | 44 |
| 107.0 | 40 |
| 108.7 | 35 |
| 125.1 | 56 |
| 128.0 | 44 |
| 130.0 | 70 |
| 132.3 | 33 |
| 135.9 | 37 |
| 137.4 | 35 |
| 139.1 | 33 |
| 149.5 | 33 |
| 155.6 | 30 |
| 163.8 | 36 |
| 169.5 | 26 |
| 174.0 | 29 |
| 188.3 | 39 |

Based on the disclosure provided herein, one of ordinary skill in the art would appreciate that each Form 1 and Form 2 of Compound A can be uniquely identified by several different spectral peaks or patterns in varying combinations. Described below are exemplary combinations of characteristic peak values that can be used to separately identify Form 1 and Form 2 of Compound A but in no way should these exemplary combinations be viewed as limiting other peak value combinations disclosed herein.

Figure 9:
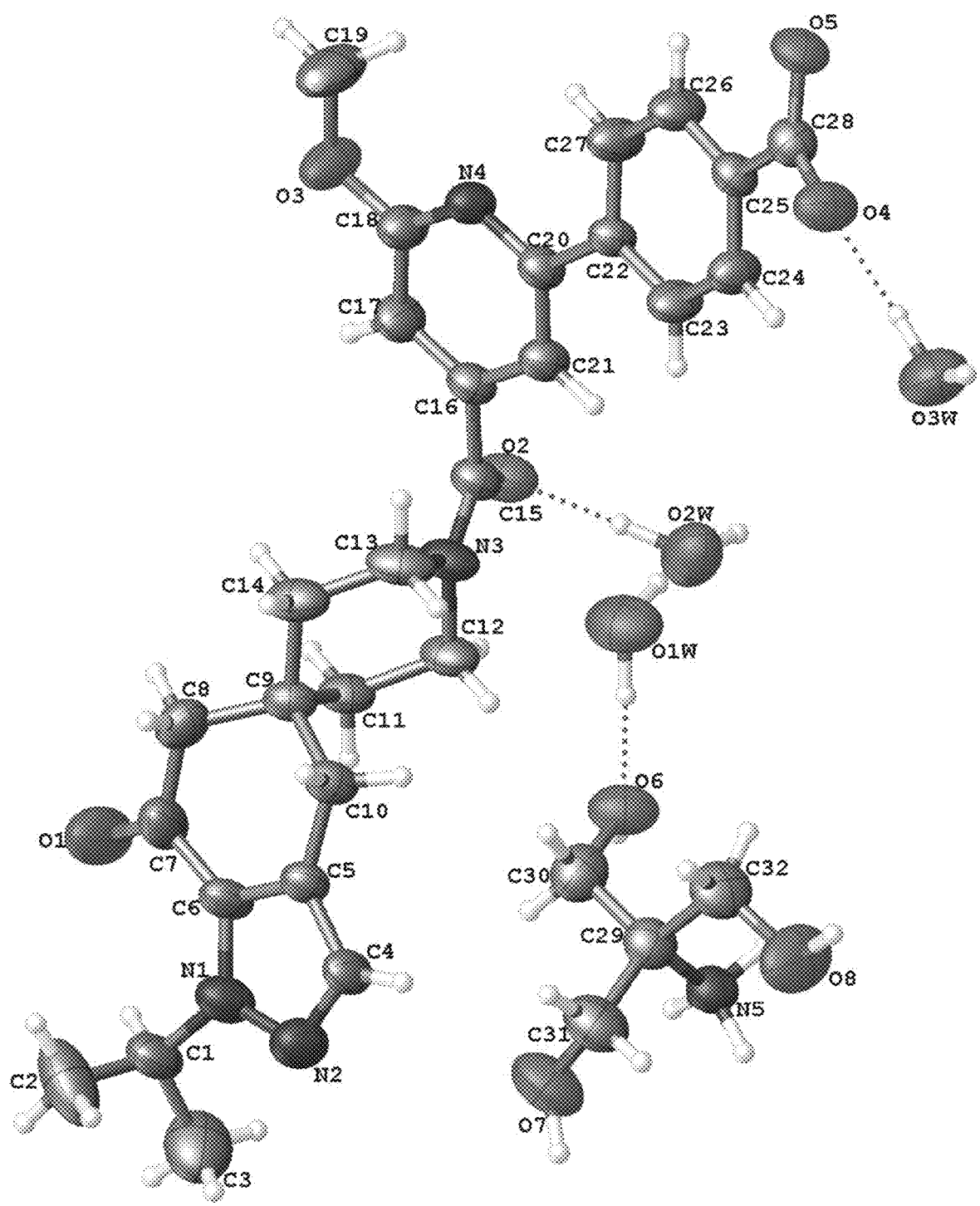
FIG. 9 shows an illustrative single crystal structure of Form 2 of Compound A.

To confirm the presence of three water molecules in Form 2 of Compound A, data was collected using a Bruker D8 Venture diffractometer at room temperature. See FIG. 9. The structure was solved by intrinsic phasing using SHELX software suite in the Monoclinic class space group $P2_1/c$ (Version 5.1, Bruker AXS, 1997). The structure was subsequently refined by the full-matrix least squares method. All non-hydrogen atoms were found and refined using anisotropic displacement parameters.

The hydrogen atoms located on nitrogen and oxygen were found from the Fourier difference map and refined with distances restrained. The remaining hydrogen atoms were placed in calculated positions and were allowed to ride on their carrier atoms.

The final R-index was 7.2%. A final difference Fourier revealed no missing or misplaced electron density.

Table 8 provides data collected with regard to Form 2 of Compound A:

TABLE 8

| | |
|---|---|
| Empirical formula | $C_{28}H_{30}N_4O_5 \cdot C_4H_{11}NO_3 \cdot 3H_2O$ |
| Formula weight | 677.74 |
| Temperature | RT |
| Wavelength | 1.54178 Å |
| Crystal system | Monoclinic |
| Space group | $P2_1/c$ |
| Unit cell dimensions | a = 17.6927(9) Å α = 90°. |
| | b = 13.2753(7) Å β = 92.451(3)°. |
| | c = 14.6480(8) Å α = 90°. |
| Volume | 3437.3(3) Å$^3$ |
| Z | 4 |
| Density (calculated) | 1.310 Mg/m$^3$ |
| Goodness-of-fit on F$^2$ | 1.053 |
| Final R indices [I > 2sigma(I)] | R1 = 0.0723, wR2 = 0.1835 |
| R indices (all data) | R1 = 0.1244, wR2 = 0.2110 |

A crystalline 2-amino-2-(hydroxymethyl)propane-1,3-diol salt of is 4-(4-(1-isopropyl-7-oxo-1,4,6,7-tetrahydrospiro[indazole-5,4'-piperidine]-1'-carbonyl)-6-methoxypyridin-2-yl)benzoic acid. This crystalline salt is generally referred to as the tris salt of Compound A.

The crystalline tris salt of Compound A, wherein the ratio of 4-(4-(1-isopropyl-7-oxo-1,4,6,7-tetrahydrospiro[indazole-5,4'-piperidine]-1'-carbonyl)-6-methoxypyridin-2-yl) benzoic acid and the salt is 1:1.

The crystalline tris salt of Compound A, wherein the crystalline salt is an anhydrous crystalline salt.

The anhydrous crystalline tris salt of Compound A, wherein said anhydrous crystalline salt has a PXRD pattern comprising peaks at diffraction angles of 9.6, 10.7, and 11.3 2Θ, ±0.2° 2Θ.

The anhydrous crystalline tris salt of Compound A, wherein said anhydrous crystalline salt has a Raman spectrum comprising peak shifts at 1511, 1561, and 1615 cm$^{-1}$, ±2 cm$^{-1}$.

The anhydrous crystalline tris salt of Compound A, wherein said anhydrous crystalline salt has a $^{13}$C ssNMR spectrum comprising chemical shifts at 22.9, 146.2, and 161.9 ppm, ±0.2 ppm.

The anhydrous crystalline tris salt of Compound A, wherein said anhydrous crystalline salt has an analytical parameter selected from the group consisting of a Raman spectrum comprising peak shifts at 1511 and 1615 cm$^{-1}$, ±2 cm$^{-1}$, and a $^{13}$C ssNMR spectrum comprising at least one chemical shift at 22.9, 146.2, or 161.9 ppm, ±0.2 ppm.

The anhydrous crystalline tris salt of Compound A, where said anhydrous crystalline salt is substantially pure.

The crystalline tris salt of Compound A, wherein the crystalline salt is a trihydrate crystalline salt.

The trihydrate crystalline tris salt of Compound A, wherein said trihydrate crystalline salt has a PXRD pattern comprising peaks at diffraction angles of 8.4, 9.0, and 10.5 2Θ, ±0.2° 2Θ.

The trihydrate crystalline tris salt of Compound A, wherein said trihydrate crystalline salt has a Raman spectrum comprising peak shifts at 1507, 1557, and 1610 cm$^{-1}$, ±2 cm$^{-1}$.

The trihydrate crystalline tris salt of Compound A, wherein said trihydrate crystalline salt has a $^{13}$C ssNMR spectrum comprising chemical shifts at 19.2, 149.5, and 163.8 ppm, ±0.2 ppm.

The trihydrate crystalline tris salt of Compound A, wherein said trihydrate crystalline salt has an analytical parameter selected from the group consisting of a PXRD pattern comprising peaks at diffraction angles of 8.4 and 9.0 2Θ, ±0.2° 2Θ, a Raman spectrum comprising peak shifts at 1557 and 1610 cm$^{-1}$, ±2 cm$^{-1}$, and a $^{13}$C ssNMR spectrum comprising at least one chemical shift at 19.2, 149.5, or 163.8 ppm, ±0.2 ppm.

The trihydrate crystalline tris salt of Compound A, wherein said trihydrate crystalline salt has an analytical parameter selected from the group consisting of a PXRD pattern comprising peaks at diffraction angles of 8.4 and 9.0 2Θ, ±0.2° 2Θ, and a Raman spectrum comprising at least one peak shift at 1507, 1557, or 1610 cm$^{-1}$, ±2 cm$^{-1}$.

The trihydrate crystalline tris salt of Compound A, wherein said trihydrate crystalline salt has an analytical parameter selected from the group consisting of a PXRD pattern comprising peaks at diffraction angles of 8.4 and 9.0 2Θ, ±0.2° 2Θ, and a $^{13}$C ssNMR spectrum comprising at least one chemical shift at 19.2, 149.5, or 163.8 ppm, ±0.2 ppm.

Pharmacological Data

The following protocols may of course be varied by those skilled in the art.

A randomized, vehicle-controlled, 8-parallel arm study was conducted in male Sprague-Dawley rats (Charles River (Boston, Mass.)) to obtain circulating and hepatic TG levels. Standard laboratory conditions were used to house 96 rats (~200 g); they were double housed and kept under 12:12-hour reverse light-dark schedule (lights off at 8:00 AM). Rats were randomized into chow or Western diet groups and dose groups upon arrival and were given a 14-day lead-in period on either standard rat chow or Western diet prior to the start of the study. Standard Laboratory Rodent chow diet, 5053, was from LabDiet (PMI, St Louis, Mo.). Western Diet, D12079Bi, was from Research Diets (New Brunswick, N.J.).

For these studies, vehicle was prepared to make a 0.5% (wt/volume) of methyl cellulose (MC, Sigma Aldrich; 274429) in deionized water. The stock solutions with either Compound A (prepared from the tris salt) or Compound D were prepared with the respective compound to provide a concentration such that 10 ml of the solution would deliver the desired mg/kg dosage amount, where the average weight of the rats used was about 200 g.

Starting on Day 1 of the study, rats were dosed orally (10 mL/kg) with either vehicle control (0.5% MC (wt/volume %) in dionized water), low or high doses of Compound A (1 mg/kg or 10 mg/kg QD, respectively), low or high doses of Compound D (5 mg/kg or 30 mg/kg BID respectively), or co-administration of low doses (Compound A at 1 mg/kg QD and Compound D at 5 mg/kg BID), or co-administration of high doses (Compound A at 10 mg/kg QD and Compound D at 30 mg/kg BID)

Fed plasma analytes: Blood for determining fed plasma TG concentrations was collected 2 hours post dose (2 hours into the dark cycle) via lateral tail vein, transferred to BD Microtainer tubes coated with dipotassium ethylenediaminetetraacetic acid ($K_2$EDTA) (PN365974), and centrifuged at 4° C. The resulting plasma samples were then analyzed on a Siemens Chemistry XPT clinical analyzer (Malven, Pa.) using Siemens triglycerides_2 assay reagents (ref 10335892).

Fasted plasma analytes: Blood for determining fasted plasma TG was collected after a 4 hour fast, 2 hours post-dose (2 hours into the dark cycle) via lateral tail vein, transferred to BD Microtainer tubes coated with $K_2$EDTA (PN365974), and centrifuged at 4° C. The resulting plasma samples were then analyzed on a Siemens Chemistry XPT clinical analyzer (Malven, Pa.) using Siemens triglycerides 2 assay reagents (ref 10335892).

On the last day of the study (Day 28), rats were sacrificed for tissue collection after a 4 hour fast, 2 hours post-dose: two hours post-dose, blood for determining plasma analytes was collected via lateral tail vein and then the animals were sacrificed by $CO_2$ asphyxiation. Blood was transferred to BD Microtainer tubes coated with $K_2$EDTA (PN365974), centrifuged at 4° C. and the plasma transferred to a 96-well microtitre plate and stored at −20° C. Livers were rapidly removed, freeze-clamped in a Wollenberg clamp pre-cooled in liquid $N_2$ individually wrapped in aluminum foil and subsequently stored at −80° C.

Tissue pulverization: Frozen livers were rapidly pulverized on an aluminum block cooled in liquid $N_2$, ensuring the tissue remained frozen throughout the pulverization. The pulverized tissues were transferred and stored in 7 mL polypropylene conical tubes at −80° C. until analysis.

Extraction for hepatic triglyceride: Approximately 50 to 100 mg of pulverized tissue was added to a 2 mL lysing matrix D tube (MP Bio) containing 800 µL ice cold 1:1 $CHCl_3$:MEOH. Samples were immediately extracted at 4° C. using Qiagen Tissue Lyser II (Qiagen Cat No. 85300) for 4 minutes at 30 Hz. The homogenate was then transferred to 13×100 mm glass tubes and placed on ice. The lysis tubes were then rinsed with 800 µL of 1:1 $CHCl_3$:MeOH, vortexed for 30 seconds and added to the 13×100 mm glass tubes. While on ice, 2.4 ml of 100% $CHCl_3$ was added to all glass vials to bring the ratio of $CHCl_3$:MeOH to 4:2. Samples were then placed in the −20° C. freezer overnight. On the following day, 1.75 mL 1M KCl $H_2O$ was added to bring the ratio to 4:2:1.75 ratio $CHCl_3$:MeOH:$H_2O$. Samples were then vortexed for 30 seconds and centrifuged at 1500 rpm×15 min., at 4° C. After centrifugation, the organic phase was transferred to a fresh 13×100 mm extraction tube, dried down at 37° C. under $N_2$ and re-suspended in 750 µL $CHCl_3$. Aminopropyl solid phase extraction (SPE) cartridges (Waters Cat No. 054560, 6 mL, 500 mg) were wetted and washed with 5 mL hexane. After the wash, 200 µL of sample extract in $CHCl_3$ was applied to the cartridge and removed by vacuum without drying the column. The neutral lipids were then eluted with 5 ml 2:1 $CHCl_3$:isopropanol/50 µM butylated hydroxytoluene. Samples were then dried down at 37° C. under $N_2$ and re-suspended with 1.75 ml of 98:2 Isooctane:Isopropanol. Samples were filtered through 0.2 µM syringe filter, before injection onto an HPLC Cyanopropy column (3.5 µM particle size-4.6×150 mm column Agilent Zorbax Eclipse XBD-CN). Running method was a 4 µL injection with a 27 minutes run time using solvent A (1000:1:2, isooctane:isopropanol:acetic acid) and solvent B (50:50 isopropanol:methyl tert-butyl ether). From minute 0-3, solvent composition was held at 100% solvent A. From minute 3-8, solvent composition was changed from 100% solvent A to 95% solvent A and 5% solvent B. From minute 8-18, solvent composition was changed to a 50:50 ratio. From minute 18-19, solvent composition was changed back to 100% solvent A and held at that composition from minutes 19-27.

Nuclear and Membrane fractions were prepared by ultracentrifugation using standard methods from a portion of the pulverized liver samples, that were pooled per treatment group. Samples from the nuclear extract and the membrane fractions were analyzed by Western blotting for SREBP1. Western blots for Calnexin was used as a marker for the membrane fraction, actin as a marker for total sample loading, and Histone 2B as a marker for the nuclear fraction. Nuclear SREBP1 levels were quantified using relative units and normalized to Histone 2B to control for sample loss during the nuclear fractionation and gel loading.

Another portion of the pulverized liver was processed and analyzed for lipogenic gene expression. Rat taqman probes against ACC1, FASN, SCD1, PCSK9 and SREBP-1c were all assessed using Actb as housekeeping gene on qPCR.

Administration of (S)-2-(5-((3-ethoxypyridin-2-yl)oxy)pyridin-3-yl)-N-(tetrahydrofuran-3-yl)pyrimidine-5-carboxamide (Compound D), or pharmaceutically acceptable salt thereof, in combination with 4-(4-(1-isopropyl-7-oxo-1,4,6, 7-tetrahydrospiro[indazole-5,4'-piperidine]-1'-carbonyl)-6-methoxypyridin-2-yl)benzoic acid (Compound A), or pharmaceutically acceptable salt thereof, has resulted in significantly decreased plasma (FIG. 10, 11) and liver TG (FIG. 18) levels compared to the plasma and liver TG levels when administering with Compound A as monotherapy.

Figure 10:
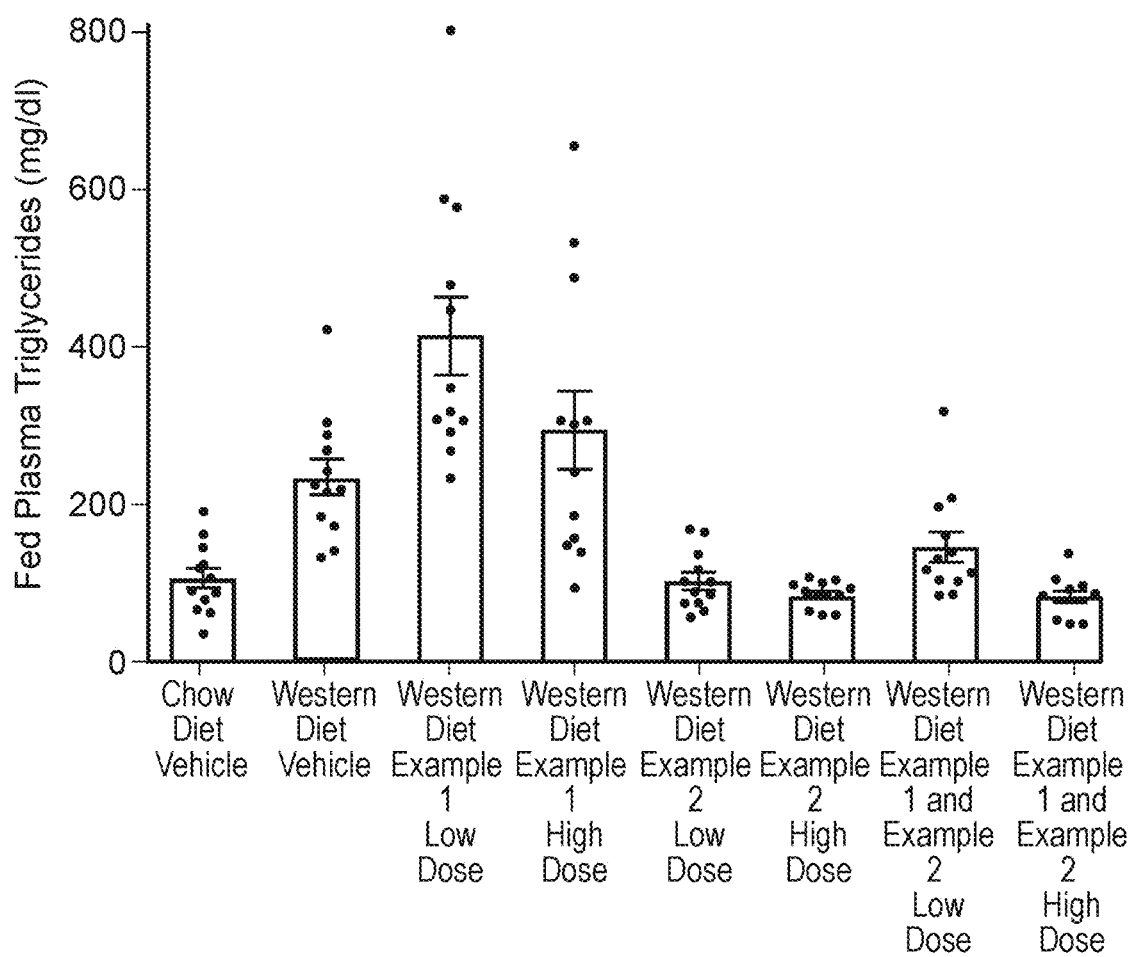
FIG. 10 summarizes the effects of oral administration as monotherapy and in combination of Compound A and Compound D on plasma triglyceride levels in Western diet fed Sprague Dawley rats, measured at the fed state.

Western diet feeding resulted in a 2.2 fold increase in fed-state plasma TG, relative to chow fed rats (FIG. 10). Oral administration of either the low dose (1 mg/kg QD) or the high dose (10 mg/kg QD) of only Compound A (monotherapy) resulted in a 1.7 fold and 1.3 fold increase, respectively, in plasma TG in the fed state, relative to vehicle-administered Western diet fed rats. Conversely, oral administration of either the low dose (5 mg/kg BID) or the high dose (30 mg/kg BID) of only Compound D (monotherapy) reduced plasma TG in the fed state by 55% and 63%, respectively, relative to vehicle-administered Western diet fed rats. Co-administration of Compound A and Compound D resulted in complete blockade of the Compound A mediated increases plasma TG in the fed state. Oral co-administration of Compound A and Compound D at either both at the low dose or both at the high dose reduced fed-state plasma TG levels by 37% and 64%, relative to vehicle-administered Western diet fed rats.

Figure 11:
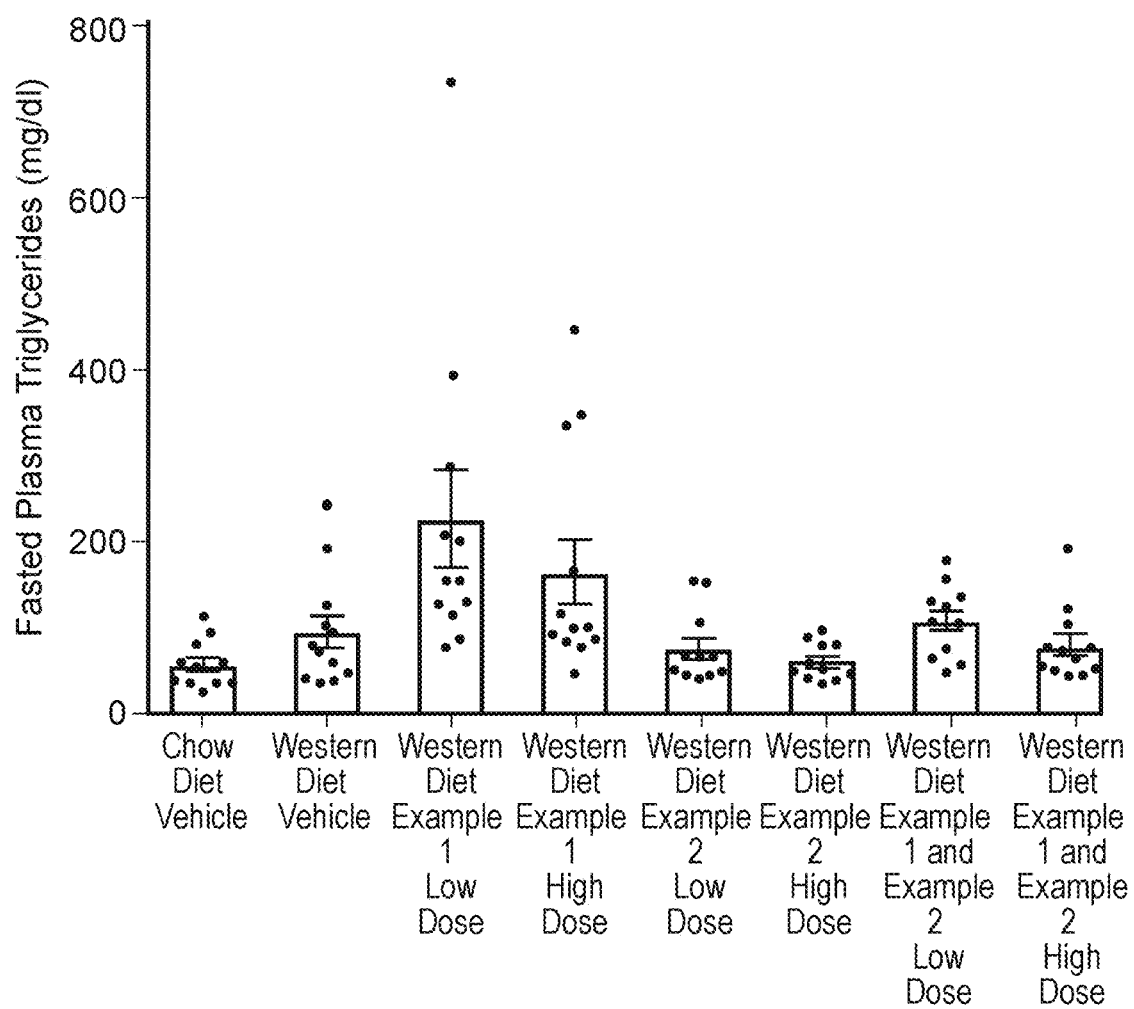
FIG. 11 summarizes the effects of oral administration as monotherapy and in combination Compound A and Compound D on plasma triglyceride levels in Western diet fed Sprague Dawley rats measured at the fasted state.

Western diet feeding resulted in a 1.6 fold increase in fasted plasma TG, relative to chow fed rats (FIG. 11). Oral administration of the low and high doses of Compound A as a monotherapy resulted in a 2.4 fold and 1.7 fold increase, respectively, in fasted plasma TG, relative to vehicle administered Western diet fed rats. Conversely, oral administration of the low and high doses of Compound D as a monotherapy reduced fasted plasma TG by 20% and 35%, respectively, relative to vehicle administered Western diet fed rats. Oral co-administration of Compound A and Compound D at both the low dose of each or the high dose of each fully mitigated the Compound A mediated increase in fasted plasma TG observed when administering only Compound A. Fasted plasma TG levels for both the low dose group (109 mg/dl) and high dose group (81 mg/dl) of the co-administered Compound A and Compound D were similar to vehicle administered Western diet fed rats (96 mg/dl).

Nuclear SREBP-1 localization was compared in samples from Western diet fed rats administered vehicle, high dose Compound A monotherapy, high dose Compound D monotherapy, or co-administered high dose Compound A and high dose Compound D (FIG. 12). Relative to vehicle treated Western diet fed rats, administration of Compound A produced increased nuclear localization of SREBP-1 indicative of increased SREBP-1 activation. Conversely, administration of Compound D reduced SREBP-1 nuclear localization and SREBP-1 activation. Co-administration of Compound A and Compound D blocked the Compound A mediated increase in nuclear SREBP-1 localization producing a 50% decrease compared with monotherapy of only Compound A.

Figure 13:
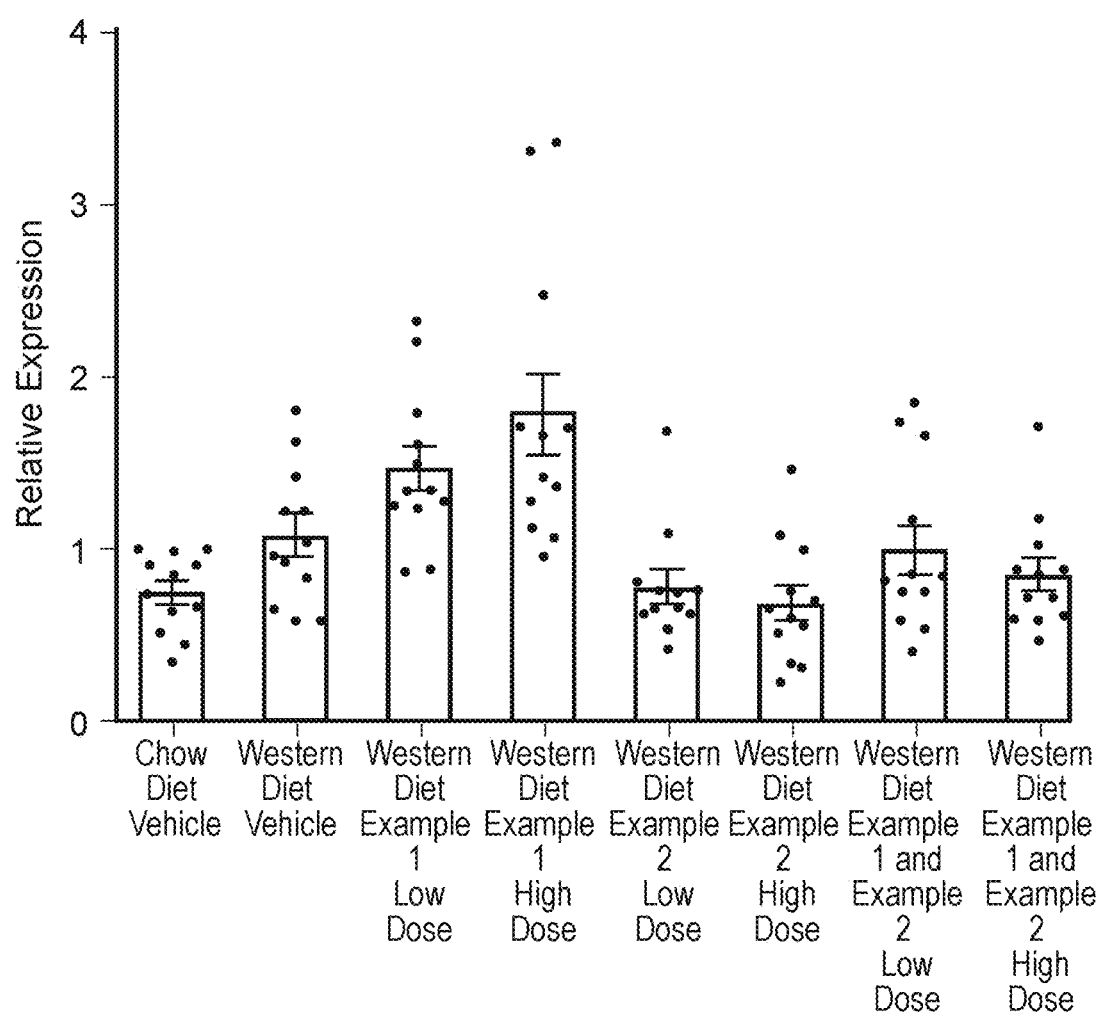
FIG. 13 summarizes the effect of administration of Compound A and Compound D as monotherapy and in combination on hepatic lipogenic gene expression in Western diet fed rats, specifically acetyl-CoA carboxylase (ACC1).
Figure 14:
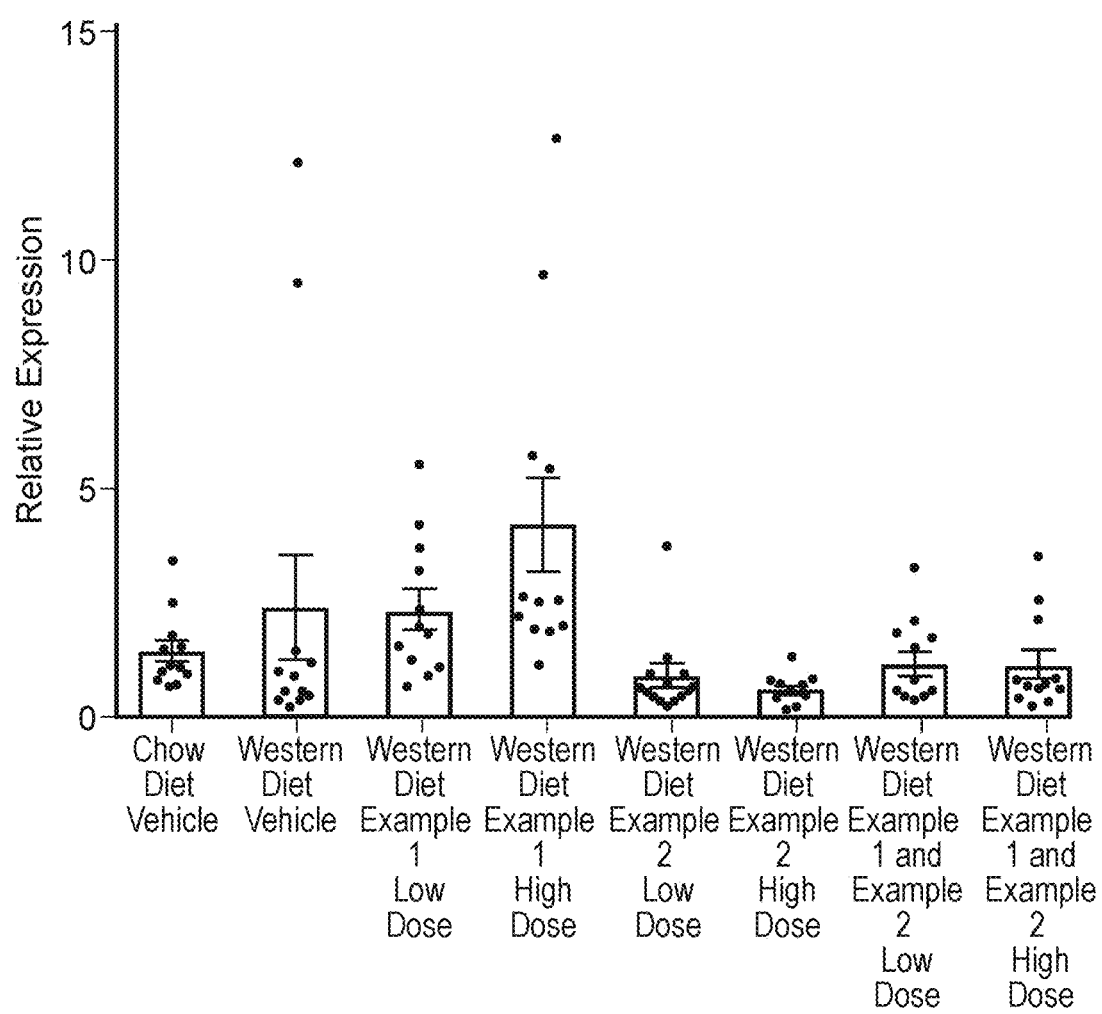
FIG. 14 summarizes the effect of administration of Compound A and Compound D as monotherapy and in combination on hepatic lipogenic gene expression in Western diet fed rats, specifically fatty acid synthase (FASN).
Figure 15:
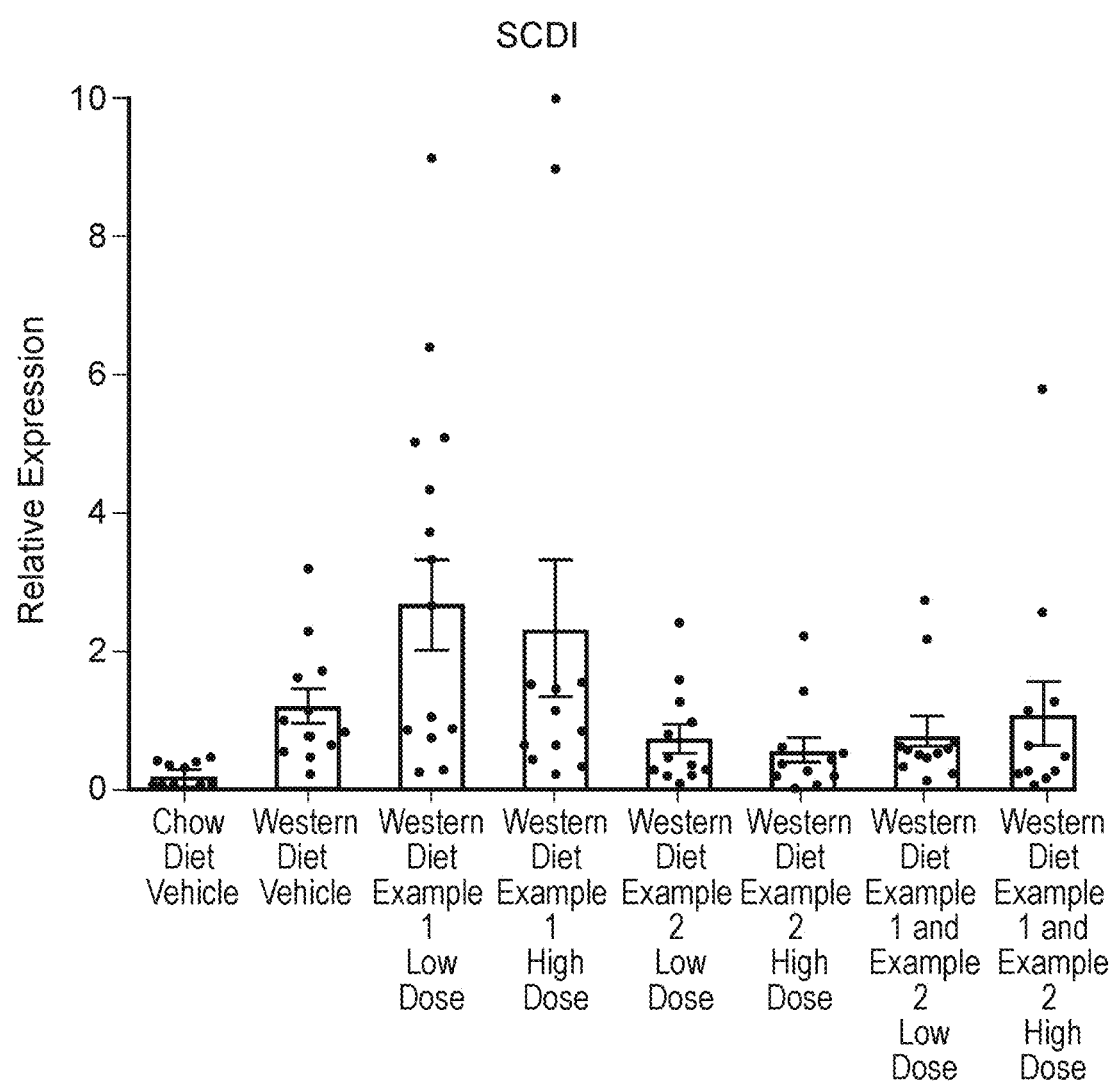
FIG. 15 summarizes the effect of administration of Compound A and Compound D as monotherapy and in combination on hepatic lipogenic gene expression in Western diet fed rats, specifically sterol-CoA desaturase (SCD1).
Figure 16:
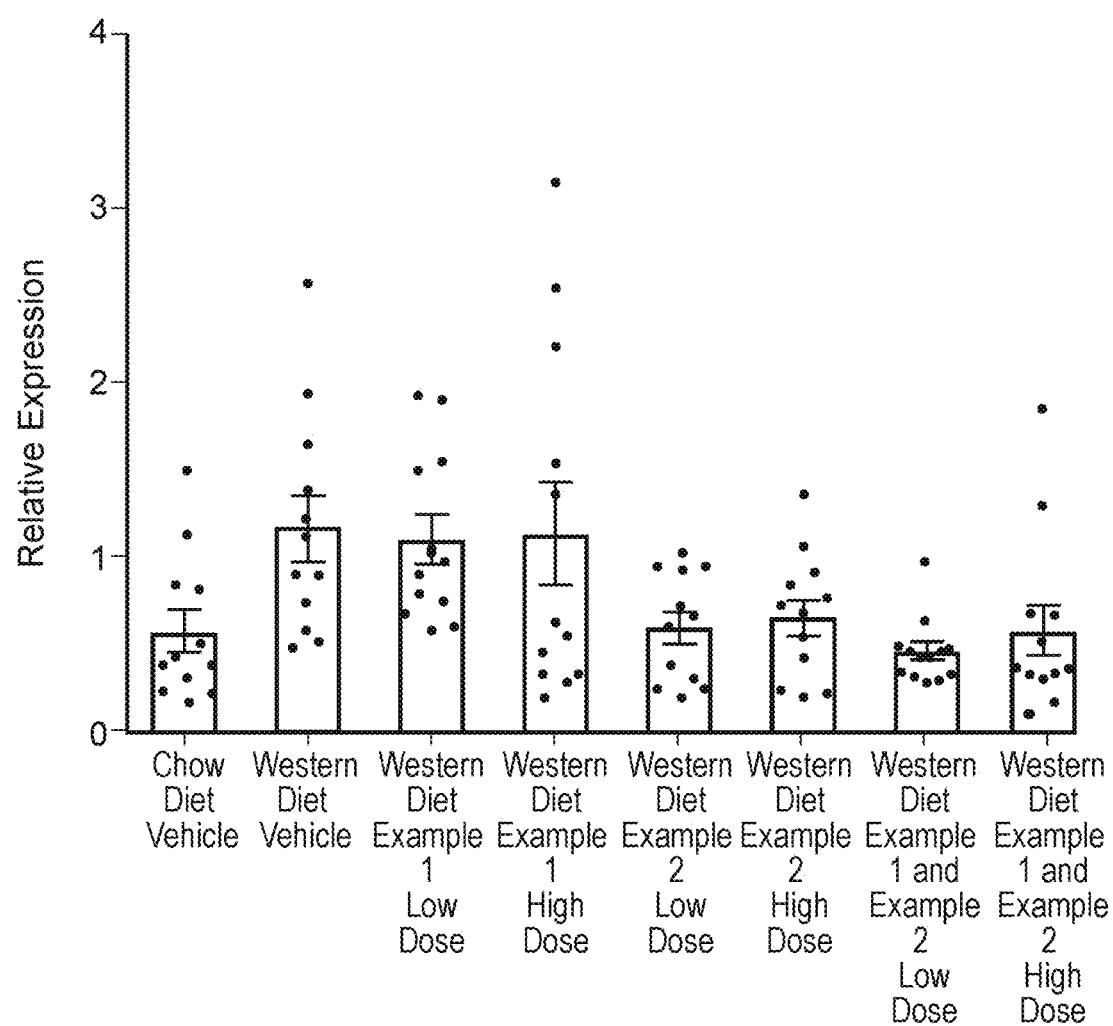
FIG. 16 summarizes the effect of administration of Compound A and Compound D as monotherapy and in combination on hepatic lipogenic gene expression in Western diet fed rats, specifically sterol regulatory element-binding protein 1c (SREBP-1c).
Figure 17:
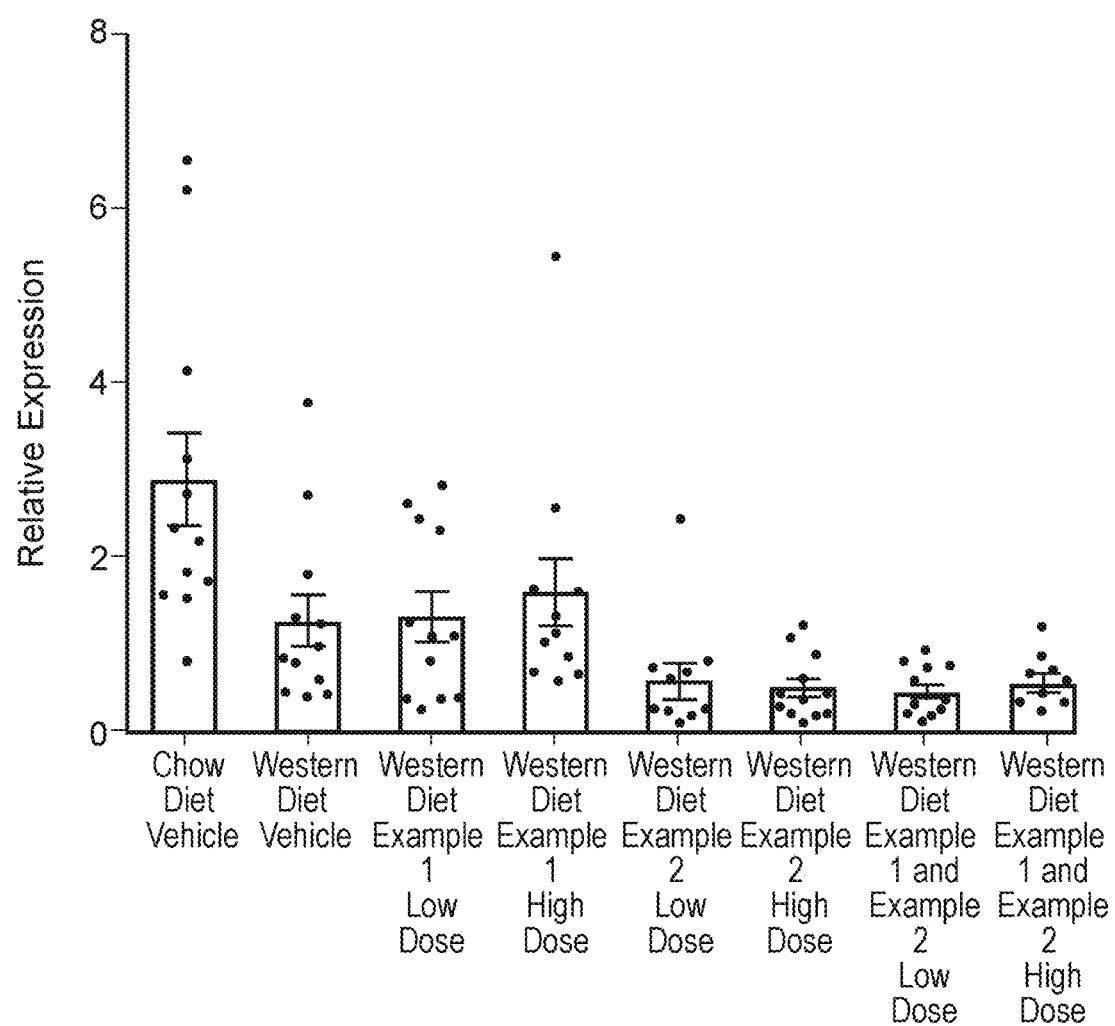
FIG. 17 summarizes the effect of administration of Compound A and Compound D as monotherapy and in combination on hepatic lipogenic gene expression in Western diet fed rats, specifically proprotein convertase subtilisin/kexin type 9 (PCSK9).

Relative to chow fed vehicle treated rats, animals fed a Western diet and treated with vehicle trended to show increased expression of the lipogenic genes: ACC1 (FIG. 13), FASN (FIG. 14), SCD1 (FIG. 15) and SREBP1 (FIG. 16), but not PCSK9 (FIG. 17), which was lower in the Western diet fed rats. Administration of Compound A trended to further increase relative to Western Diet fed and vehicle treated animals, the expression of ACC1, FASN (Compound A high dose only), SCD, but not PCSK9 and SREBP1. Conversely, administration of Compound D decreased expression of all of the lipogenic genes. Co-administration of Compound A and Compound D resulted in expression levels being comparable or lower than those observed in vehicle treated Western diet fed rats.

Figure 18:
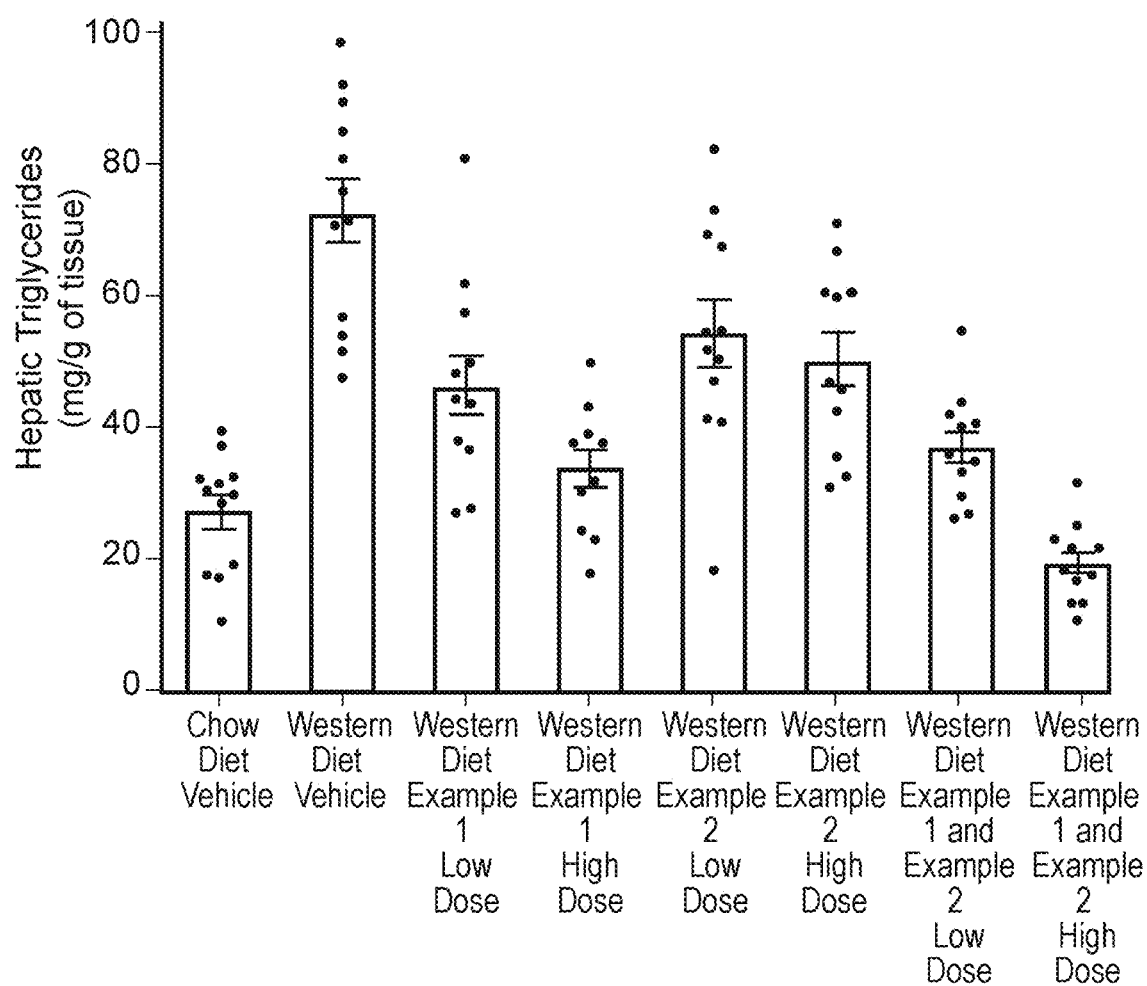
FIG. 18 summarizes the effects of oral administration as monotherapy and in combination of Compound A and Compound D on hepatic triglyceride levels in Western diet fed Sprague Dawley rats.

Relative to chow fed rats, vehicle administered Western diet fed rats showed about a 2.7-fold increase in hepatic triglyceride accumulation (FIG. 18). Oral administration of the low dose and high dose of Compound A produced a 36% and 53% reduction, respectively, in steatosis, relative to vehicle administered Western diet fed rats. Similarly, oral administration of the low dose and high dose of Compound D reduced steatosis by 25% and 30%, respectively, relative to vehicle administered Western diet fed rats. Oral co-administration of either the low or high dose of both Compound A and Compound D reduced steatosis by 50% and 73%, respectively, relative to vehicle administered Western diet fed rats. Oral administration of either the low dose or high dose combination of Compound A and Compound D produced greater reductions in steatosis than that observed with administration of either Compound A or Compound D as monotherapy at the same dose levels.

A randomized, vehicle-controlled, 5-parallel arm study was conducted in male Wistar-Han rats (Charles River (Boston, Mass.)) fed a choline-deficient and high fat diet (CDAHFD) (Research diets; A16092003) to identify differences in improvements in markers of hepatic inflammation and fibrosis when administering either Compound A or Compound D alone as monotherapy or in combination. Standard laboratory conditions were used to house 60 rats (~200 g); they were double housed and kept under 12:12-hour reverse light-dark schedule (lights off at 8:00 AM). Rats were fed choline deficient and high fat diet (CDAHFD) beginning 6-weeks prior to initiation of the study. Rats, randomized into 4 dosing groups (n=12/group), received twice daily administration of vehicle, Compound A (5 mg/kg) monotherapy, Compound D (30 mg/kg) monotherapy, or co-administration Compound A (5 mg/kg) and Compound D (30 mg/kg) for a period of 6-weeks. Animals (n=12) remaining on normal chow throughout the study and administered twice-daily vehicle were used as a control group. Blood samples were collected prior to starting compound administration and 3- and 6-week post compound administration for the assessment of circulating markers. Shearwave elastography (Aixplorer Ultimate imager, Supersoinc imagine) measurements were made at Week −3, Week 0 (prior to $1^{st}$ dose), Week 3 and Week 6 to assess inflammation and fibrosis progression over time. Histology was assessed following 6-weeks of drug administration which corresponded to 12 weeks on the CDAHFD. Results are provided as an average of animals per each dosing group.

Following the 12-weeks on CDAHFD, the animals were sacrificed by $CO_2$ asphyxiation. The right lateral, medial and left lateral lobes of the liver were harvested. Sections were taken from the left lateral, right medial and right lateral lobes and fixed in formalin and processed to paraffin blocks per animal. One section of left lateral lobe per animal was cryopreserved in optimal cutting temperature (OCT) compound. The remainder of the liver from each animal was frozen and rapidly pulverized on an aluminum block cooled in liquid $N_2$, ensuring the tissue remained frozen throughout the pulverization. The pulverized tissue was transferred and stored at −80° C. until analysis. A portion of the pulverized liver sample from each animal was processed and analyzed for gene expression markers of fibrogenesis. Rat taqman probes against □SMA and COL1A1 were all assessed using Actb as housekeeping gene on qPCR.

The following endpoints were evaluated by qualitative histologic evaluation by a board certified veterinary pathologist and quantitative histomorphometry: hepatic stellate cell activation and differentiation into myofibroblasts by αSMA immunohistochemistry (IHC); Collagen as a correlate of fibrosis by Picrosirius Red stain. Images were analyzed using Visiopharm software. Visiopharm applications with threshold parameters were applied uniformly to identify tissue sections and to quantify the targets on each IHC (DAB (3,3'-diaminobenzidine) positive) or histochemically stained slides as percent area: stain area of interest/Total tissue ROI−whitespace)×100%. Non-parametric statistics were used to analyze data from this study. Group values were reported as mean+/−the standard error of the mean.

Figure 19:
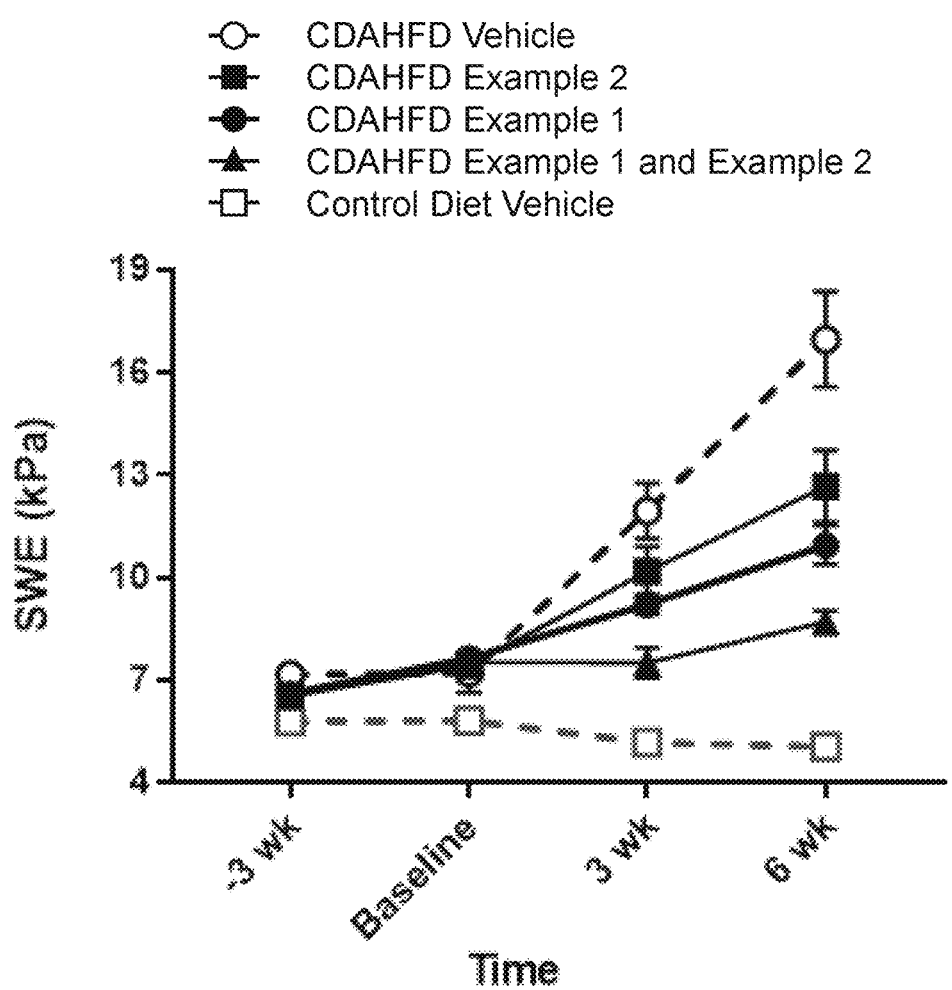
FIG. 19 summarizes the effects of oral administration as monotherapy and in combination of Compound A and Compound D on elasticity of the liver, a marker of hepatic inflammation and fibrosis, in choline deficient and high fat diet (CDAHFD) fed Male Wistar Hann rats.

Relative to control animals fed a chow diet and administered vehicle, animals that received CDAHFD and administered vehicle showed a marked increase in liver stiffness (assessed using shearwave elastography (SWE), measured in kilopascals (kPa)) over the duration of the study, indicative of progressive hepatic inflammation and fibrosis (FIG. 19). Administration of Compound A or Compound D as monotherapy each reduced liver stiffness suggestive of reduced hepatic inflammation and/or fibrosis. Co-administration of Compound A and Compound D produced greater reductions in liver stiffness than either agent as monotherapy (FIG. 19).

Figure 20:
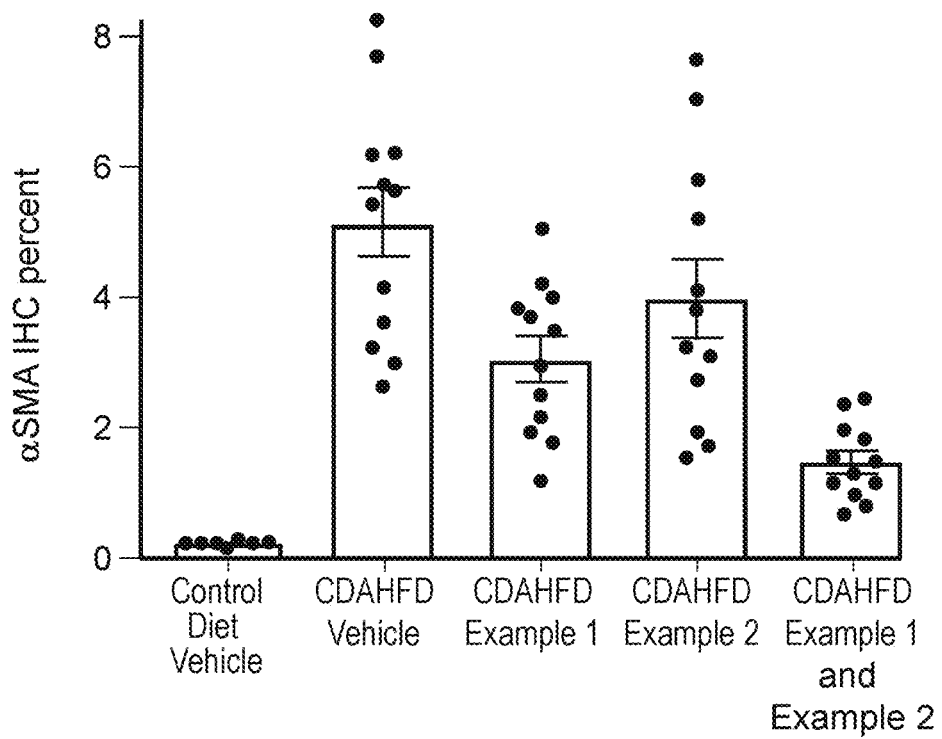
FIG. 20 summarizes the effects of oral administration as monotherapy and in combination of Compound A and Compound D on hepatic alpha smooth actin (αSMA) immunohistochemistry, a marker of myofibroblast activation and fibrogenesis, in CDAHFD fed Male Wistar Hann rats.

Relative to control animals fed a chow diet and administered vehicle, animals that received CDAHFD and administered vehicle showed a marked increase in liver alpha smooth muscle actin (αSMA) staining, indicative of myofibroblast activation and fibrogenesis (FIG. 20). Administration of Compound A or Compound D as monotherapy each reduced αSMA staining by 41% and 23%, respectively, suggestive of reduced hepatic myofibroblast activation and fibrogenesis. Co-administration of Compound A and Compound D produced greater reductions in ☐SMA staining than either agent as monotherapy, reducing staining by 72% (FIG. 20).

Figure 21:
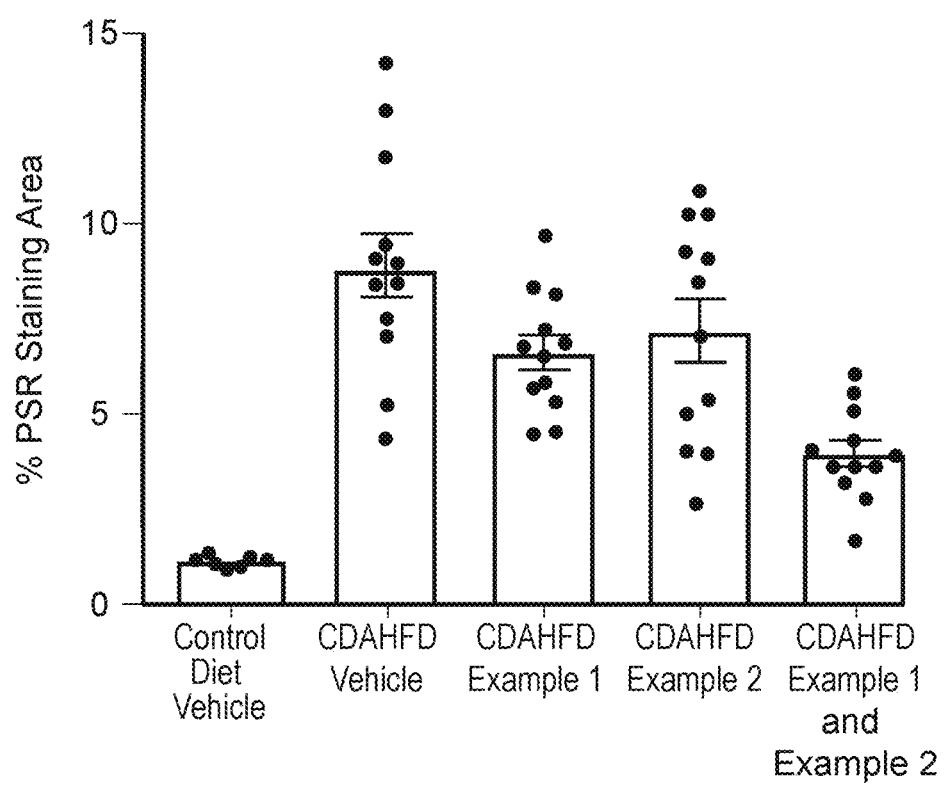
FIG. 21 summarizes the effects of oral administration as monotherapy and in combination of Compound A and Compound D on hepatic Picosirius red staining in CDAHFD fed Male Wistar Hann rats.

Relative to control, animals fed a chow diet and administered vehicle showed a marked increase in Picosrius red (PSR) staining, indicative of collagen deposition and fibrosis (FIG. 21). Administration of Compound A or Compound D as monotherapy each reduced PSR staining by 26% and 20%, respectively, suggestive of reduced collagen deposition and fibrosis. Co-administration of Compound A and Compound D produced greater reductions in PSR staining than either agent as monotherapy, reducing staining by 56% (FIG. 21).

Figure 24:
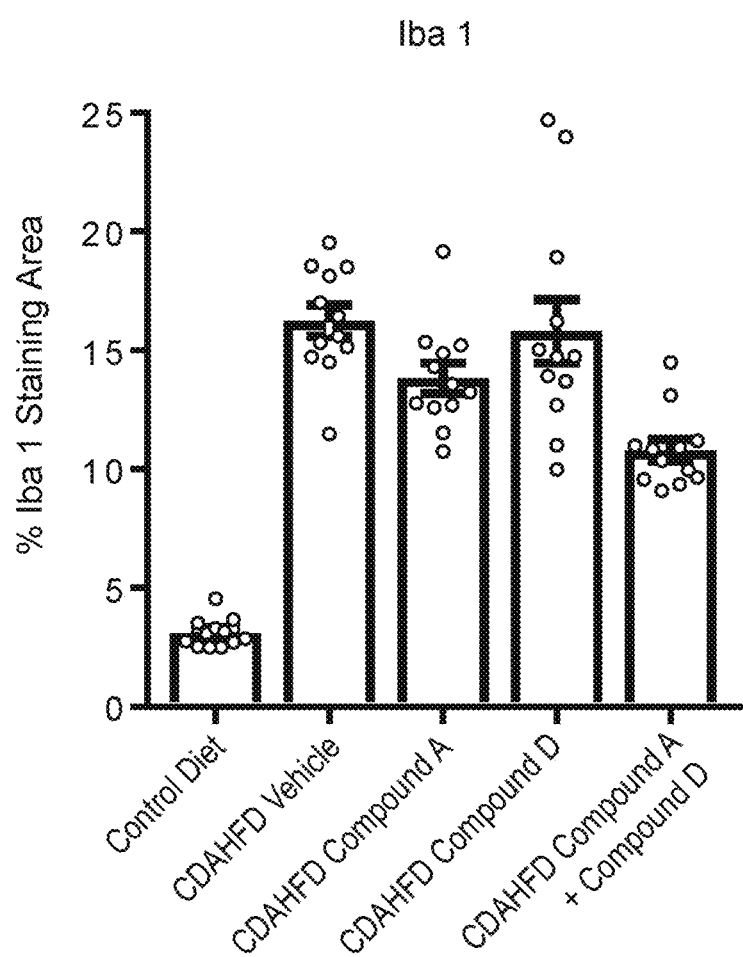
FIG. 24 summarizes the effects of oral administration as monotherapy and in combination of Compound A and Compound D on Ionized Calcium-Binding Adapter Molecule 1 Staining in CDAHFD fed Male Wistar Hann rats.

Relative to control, animals fed a chow diet and administered vehicle showed a marked increase in Ionized calcium binding adaptor molecule 1 (Iba1) staining, indicative of hepatic macrophage activation (FIG. 24). Administration of Compound A as monotherapy reduced Iba1 staining by 15%, suggestive of reduced hepatic inflammatory tone. While administration of D as monotherapy did not alter Iba1 staining, co-administration of A and D produced greater reductions in Iba1 staining than Compound A administered as monotherapy, decreasing staining by 33% (FIG. 24)

Figure 22:
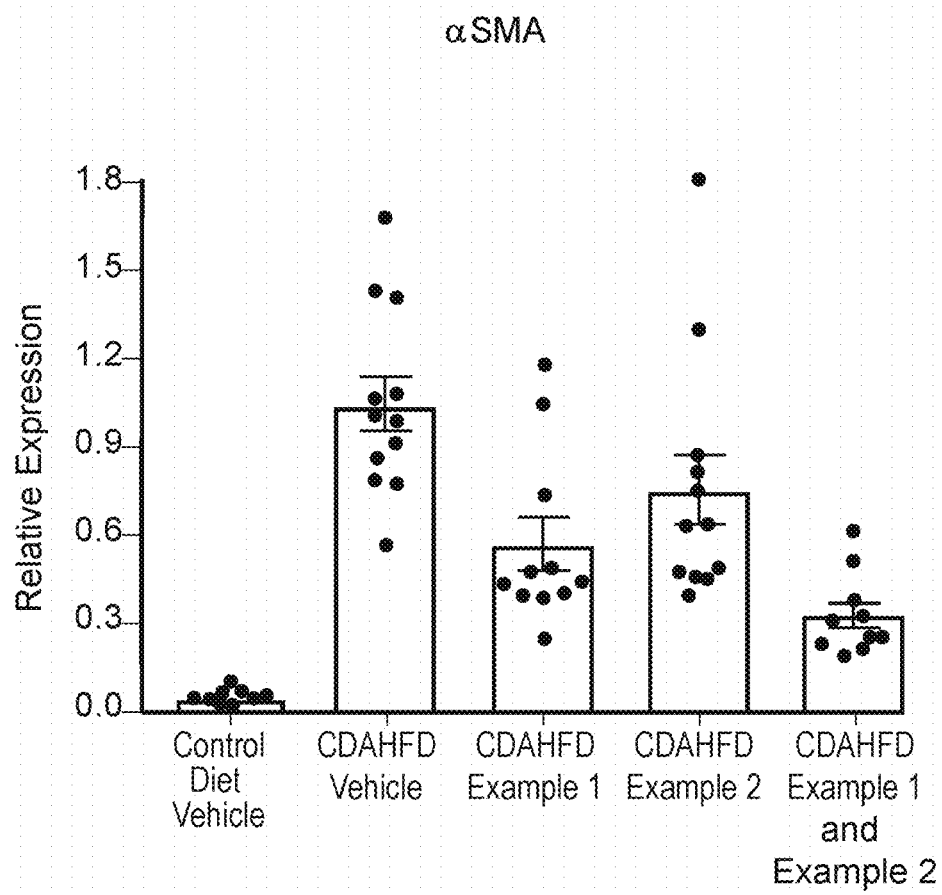
FIG. 22 summarizes the effects of oral administration as monotherapy and in combination of Compound A and Compound D on hepatic alpha smooth actin (αSMA) gene expression in CDAHFD fed Male Wistar Hann rats.
Figure 23:
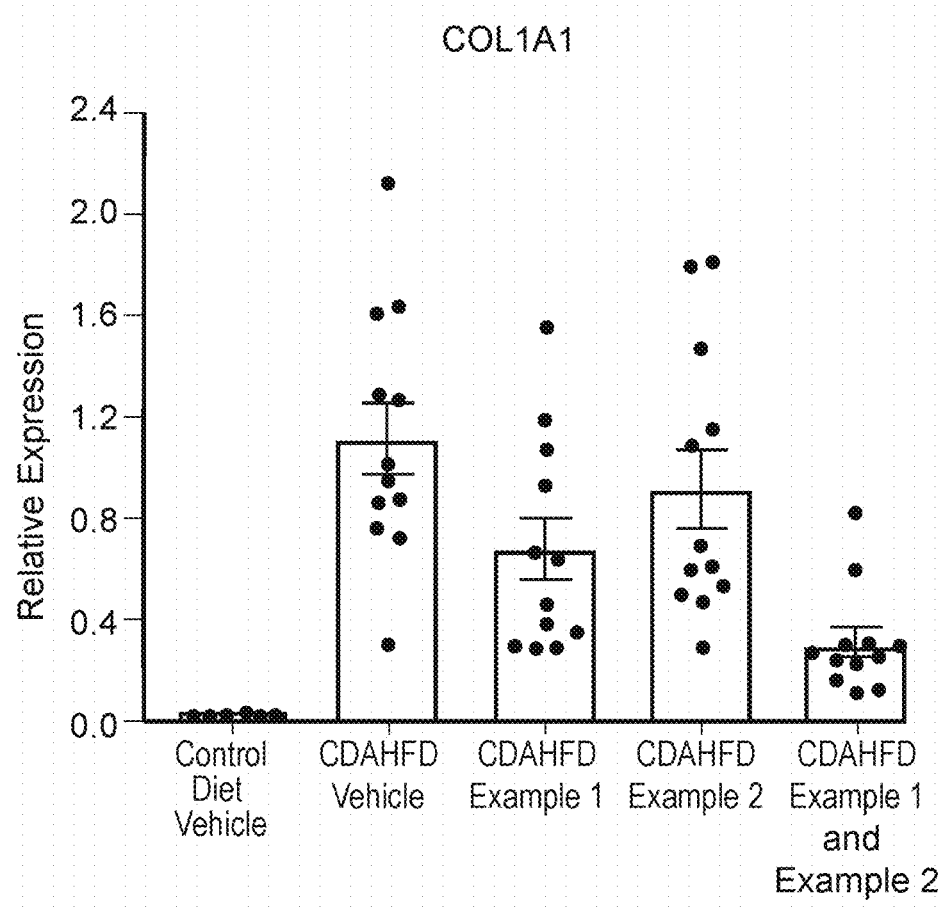
FIG. 23 summarizes the effects of oral administration as monotherapy and in combination of Compound A and Compound D on hepatic collagen 1A1 gene expression in CDAHFD fed Male Wistar Hann rats.

Relative to control animals fed a chow diet and administered vehicle, animals that received CDAHFD and administered vehicle showed a marked increase in liver alpha smooth muscle actin (αSMA) (FIG. 22) and collagen A1A (COL1A1) (FIG. 23) gene expression, indicative of myofibroblast activation and fibrogenesis. Administration of Compound A or Compound D as monotherapy each reduced hepatic αSMA and COL1A1 gene expression, suggestive of reduced hepatic myofibroblast activation and fibrogenesis. Co-administration of Compound A and Compound D produced greater reductions in hepatic αSMA (FIG. 22) and COL1A1 (FIG. 23) gene expression than either agent as monotherapy.

Throughout this application, various publications are referenced. The disclosures of these publications in their entireties are hereby incorporated by reference into this application for all purposes.

It will be apparent to those skilled in the art that various modifications and variations can be made in the invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pharmaceutical composition comprising (S)-2-(5-((3-ethoxypyridin-2-yl)oxy)pyridin-3-yl)-N-(tetrahydrofuran-3-yl)pyrimidine-5-carboxamide, or a pharmaceutically acceptable salt thereof, in combination with at least 4-(4-(1-Isopropyl-7-oxo-1,4,6,7-tetrahydrospiro[indazole-5,4'-piperidine]-t-carbonyl)-6-methoxpyridin-2-yl)benzoic acid, or a pharmaceutically acceptable salt thereof, each present in therapeutically effective amounts, in admixture with a pharmaceutically acceptable excipient.

2. A pharmaceutical composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, 4-(4-(1-Isopropyl-7-oxo-1,4,6,7-tetrahydrospiro[indazole-5,4'-piperidine]-1'-carbonyl)-6-methoxpyridin-2-yl)benzoic acid or a pharmaceutically acceptable salt thereof, and a pharmaceutically acceptable excipient.

3. The composition of claim 2, further comprising at least one additional pharmaceutical agent selected from the group consisting of an anti-inflammatory agent, an anti-diabetic agent, and a cholesterol/lipid modulating agent.

4. A method for alleviating a disease or condition selected from nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma, the method comprising administering to a patient in need of such treatment a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, in combination with at least a therapeutically effective amount of 4-(4-(1-Isopropyl-7-oxo-1,4,6,7-tetrahydrospiro[indazole-5,4'-piperidine]-1'-carbonyl)-6-methoxpyridin-2-yl)benzoic acid or a pharmaceutically acceptable salt thereof.

5. A method for alleviating a disease or condition selected from nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma, the method comprising administering to a human in need of such treatment a therapeutically effective amount of (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, and 4-(4-(1-Isopropyl-7-oxo-1,4,6,7-tetrahydrospiro[indazole-5,4'-piperidine]-t-carbonyl)-6-methoxpyridin-2-yl)benzoic acid or a pharmaceutically acceptable salt thereof.

6. The method of claim 5, wherein the disease or condition is fatty liver.

7. The method of claim 5, wherein the disease or condition is nonalcoholic fatty liver disease.

8. The method of claim 5, wherein the disease or condition is nonalcoholic steatohepatitis.

9. The method of claim 5, wherein the disease or condition is nonalcoholic steatohepatitis with liver fibrosis.

10. The method of claim 5, wherein the disease or condition is nonalcoholic steatohepatitis with cirrhosis.

11. The method of claim 10, wherein the disease or condition is nonalcoholic steatohepatitis with cirrhosis and with hepatocellular carcinoma.

12. The method of claim 5, wherein the method comprises further administering a therapeutically effective amount of at least one other pharmaceutical agent selected from the group consisting of an acetyl-CoA carboxylase- (ACC) inhibitor, a diacylglycerol O-acyltransferase 1 (DGAT-1) inhibitor, monoacylglycerol O-acyltransferase inhibitors, a phosphodiesterase (PDE)-10 inhibitor, an AMPK activator, a sulfonylurea, a meglitinide, an α-amylase inhibitor, an α-glucoside hydrolase inhibitor, an α-glucosidase inhibitor, a PPARγ agonist, a PPAR α/γ agonist, a biguanide, a glucagon-like peptide 1 (GLP-1) modulator, liraglutide, albiglutide, exenatide, albiglutide, lixisenatide, dulaglutide, semaglutide, a protein tyrosine phosphatase-1B (PTP-1B) inhibitor, SIRT-1 activator, a dipeptidyl peptidase IV (DPP-IV) inhibitor, an insulin secreatagogue, a fatty acid oxidation inhibitor, an A2 antagonist, a c-jun amino-terminal kinase (JNK) inhibitor, glucokinase activators (GKa), insulin, an insulin mimetic, a glycogen phosphorylase inhibitor, a VPAC2 receptor agonist, SGLT2 inhibitors, a glucagon receptor modulator, GPR119 modulators, FGF21 derivatives or analogs, TGR5 receptor modulators, GPBAR1 receptor modulators, GPR40 agonists, GPR120 modulators, high affinity nicotinic acid receptor (HM74A) activators, SGLT1 inhibitors, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms PKCα, PKCβ, and PKCγ, inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors, inhibitors or modulators of PDHK2 or PDHK4, inhibitors of MAP4K4, modulators of IL1 family, HMG-CoA reductase inhibitors, squalene synthetase inhibitors, fibrates, bile acid sequestrants, ACAT inhibitors, MTP inhibitors, lipooxygenase inhibitors, cholesterol absorption inhibitors, PCSK9 modulators, cholesteryl ester transfer protein inhibitors and modulators of RXRalpha.

13. A method for alleviating nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and with hepatocellular carcinoma in humans comprising the step of administering to a human in need of such treatment a therapeutically effective amount of a first and second agent, and optionally a third agent wherein:
   i. the first agent comprises (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof;
   ii. the second agent comprises 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof; and
   iii. the third agent comprises a pharmaceutical agent selected from the group consisting of an anti-inflammatory agent, an anti-diabetic agent, an anti-fibrotic agent, an anti-steatiotic agent, a cholesterol/lipid modulating agent and an anti-diabetic agent.

14. A method according to claim 5, wherein (S)-2-(5-((3-ethoxypyridin-2-yl)oxy)pyridin-3-yl)-N-(tetrahydrofuran-3-yl)pyrimidine-5-carboxamide is a crystalline solid of structure:

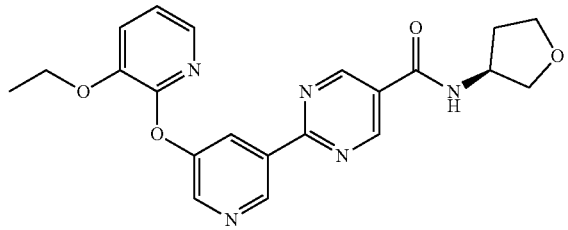 [SMILES: CCOc1cccnc1Oc1cncc(-c2ncc(C(=O)N[C@H]3CCOC3)cn2)c1]

or a pharmaceutically acceptable salt thereof.

15. The method of claim 14, wherein the crystalline solid has a powder x-ray diffraction pattern comprising 2-theta values of (CuKα radiation, wavelength of 1.54056 Å) 5.3±0.2, 7.7±0.2, and 15.4±0.2.

16. The method of claim 14, wherein the crystalline solid has a powder x-ray diffraction pattern comprising 2-theta values of (CuKα radiation, wavelength of 1.54056 Å) 6.5±0.2, 9.3±0.2, and 13.6±0.2.

17. A method according to claim 5, wherein 4-(4-(1-Isopropyl-7-oxo-1,4,6,7-tetrahydrospiro[indazole-5,4'-piperidine]-1'-carbonyl)-6-methoxypyridin-2-yl)benzoic acid is a crystalline solid of structure:

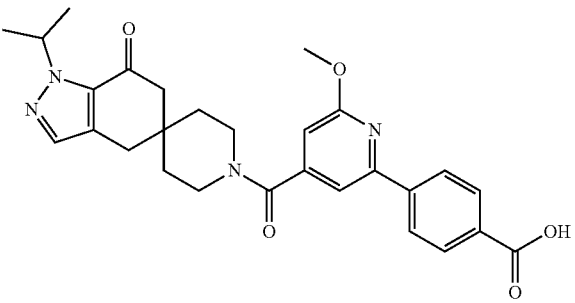 [SMILES: COc1cc(C(=O)N2CCC3(CC2)CC(=O)c2c(cnn2C(C)C)C3)cc(-c2ccc(C(=O)O)cc2)n1]

or a pharmaceutically acceptable salt thereof.

18. The method of claim 17, wherein the crystalline solid is 2-amino-2-(hydroxymethyl)propane-1,3-diol salt of 4-(4-(1-isopropyl-7-oxo-1,4,6,7-tetrahydrospiro[indazole-5,4'-piperidine]-1'-carbonyl)-6-methoxypyridin-2-yl)benzoic acid.

19. The pharmaceutical composition as recited in claim 2, wherein (S)-2-(5-((3-ethoxypyridin-2-yl)oxy)pyridin-3-yl)-N-(tetrahydrofuran-3-yl)pyrimidine-5-carboxamide is a crystalline solid of structure:

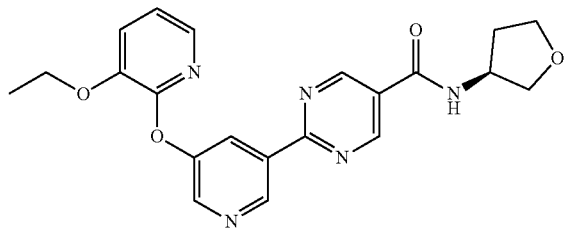 [SMILES: CCOc1cccnc1Oc1cncc(-c2ncc(C(=O)N[C@H]3CCOC3)cn2)c1]

or a pharmaceutically acceptable salt thereof.

20. The pharmaceutical composition as recited in claim 19, wherein the crystalline solid has a powder x-ray diffraction pattern comprising 2-theta values of (CuKα radiation, wavelength of 1.54056 Å) 5.3±0.2, 7.7±0.2, and 15.4±0.2.

21. The pharmaceutical composition as recited in claim 19, wherein the crystalline solid has a powder x-ray diffraction pattern comprising 2-theta values of (CuKα radiation, wavelength of 1.54056 Å) 6.5±0.2, 9.3±0.2, and 13.6±0.2.

22. The pharmaceutical composition as recited claim 2, wherein 4-(4-(1-Isopropyl-7-oxo-1,4,6,7-tetrahydrospiro[indazole-5,4'-piperidine]-1'-carbonyl)-6-methoxypyridin-2-yl)benzoic acid is a crystalline solid of structure:

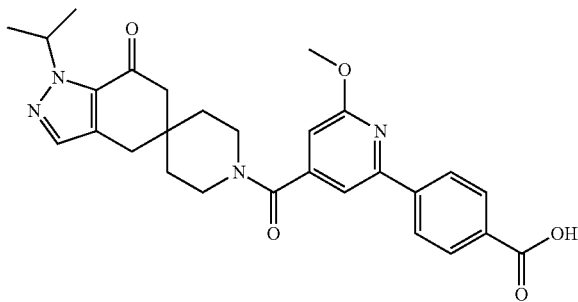 [SMILES: COc1cc(C(=O)N2CCC3(CC2)CC(=O)c2c(cnn2C(C)C)C3)cc(-c2ccc(C(=O)O)cc2)n1]

or a pharmaceutically acceptable salt thereof.

23. The pharmaceutical composition as recited in claim 22, wherein the crystalline solid is 2-amino-2-(hydroxymethyl)propane-1,3-diol salt of 4-(4-(1-isopropyl-7-oxo-1,4,6,7-tetrahydrospiro[indazole-5,4'-piperidine]-1'-carbonyl)-6-methoxypyridin-2-yl)benzoic acid.

24. The method as recited in claim 2, wherein at least one other pharmaceutical agent is used and is selected from the group consisting of [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid; 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid; or 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

25. A method for alleviating a disease or condition selected from nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma, the method comprising administering to a human in need of such treatment a composition comprising (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof, 4-(4-(1-Isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, and a pharmaceutically acceptable excipient.

\* \* \* \* \*